United States Patent
Toscano et al.

(10) Patent No.: US 11,001,786 B2
(45) Date of Patent: *May 11, 2021

(54) PROTEASE VARIANTS AND POLYNUCLEOTIDES ENCODING SAME

(71) Applicant: NOVOZYMES A/S, Bagsvaerd (DK)

(72) Inventors: Miguel Duarte Guilherme Pereira Toscano, Greve (DK); Esben Peter Friis, Herlev (DK); Bena-Marie Lue, Holte (DK)

(73) Assignee: NOVOZYMES A/S, Bagsvaerd (DK)

( * ) Notice: Subject to any disclaimer, the term of this patent is extended or adjusted under 35 U.S.C. 154(b) by 0 days.

This patent is subject to a terminal disclaimer.

(21) Appl. No.: 16/776,740

(22) Filed: Jan. 30, 2020

(65) Prior Publication Data

US 2020/0157473 A1    May 21, 2020

Related U.S. Application Data

(62) Division of application No. 15/536,908, filed as application No. PCT/EP2015/080615 on Dec. 18, 2015, now Pat. No. 10,590,367.

(30) Foreign Application Priority Data

Dec. 19, 2014   (EP) ..................................... 14199407

(51) Int. Cl.
    *C11D 3/386*   (2006.01)
    *C12N 9/54*    (2006.01)

(52) U.S. Cl.
    CPC ............. *C11D 3/386* (2013.01); *C12N 9/54* (2013.01); *C12Y 304/21* (2013.01)

(58) Field of Classification Search
    CPC .......... C12Y 304/21; C11D 3/386; C12N 9/54
    See application file for complete search history.

(56) References Cited

U.S. PATENT DOCUMENTS

| | | | |
|---|---|---|---|
| 9,719,077 B2 | 8/2017 | Rasmussen | |
| 10,400,230 B2 * | 9/2019 | Rasmussen | C11D 3/38663 |
| 10,590,367 B2 * | 3/2020 | Toscano | C11D 3/386 |
| 2002/0103100 A1 | 8/2002 | Outtrup | |
| 2003/0032162 A1 | 2/2003 | Schnorr | |
| 2012/0088288 A1 | 4/2012 | Svendsen | |

FOREIGN PATENT DOCUMENTS

| | | |
|---|---|---|
| DE | 10 2007 032 111 A | 1/2009 |
| EP | 2 832 853 A1 | 2/2015 |
| WO | 91/000345 A1 | 1/1991 |
| WO | 92/17577 A1 | 10/1992 |
| WO | 01/44452 A1 | 6/2001 |
| WO | 2004/067737 A2 | 8/2004 |
| WO | 2004/083362 A2 | 9/2004 |
| WO | 2009/019157 A1 | 2/2009 |
| WO | 2015/014804 A1 | 2/2015 |
| WO | 2016/066757 A2 | 5/2016 |
| WO | 2016/097350 A1 | 6/2016 |
| WO | 2016-097357 A1 | 6/2016 |

OTHER PUBLICATIONS

Davail et al, 1994, The J of Biological Chem 269(26), 17448-17453.
Narinx et al, 1997, Protein Engineering 10(11), 1271-1279.
Siezen et al, 1997, Protein Sci 6, 501-523.
Mykytczuk et al, 2013, UniProt No. M3FAL1.
Peng et al, 2014, UniProt accession No. W7LCX0.
Lucas et al, 2010, UniProt accession No. D2PQL0.
Lucas et al, 2013, UniProt accession No. K6Q0H4.
Morohoshi et al, 2011, UniProt accession No. F2F8D9.
Sakai et al, 2010, Uniprot accession No. D1Z2F2.
Salwan et al, 2014, UniProt No. W3AHK2.
Shivaji et al, 2012, UniProt No. K1LPU3.
Wahl et al, 1987, Methods Enzymol 152, 399-407.
Col et al, 2014, UniProt No. V6SXF8.
Col et al, 2014, UniProt No. V6T5D0.
Edwards et al, 2007, UniProt No. A3I3T6.
Fomenkov et al, 2014, EBI Accession No. A0A077J6A6.
Wu et al, 2003, FEMS Microbiol Lett 230(2), 251-258.

* cited by examiner

*Primary Examiner* — Ganapathirama Raghu
(74) *Attorney, Agent, or Firm* — Kelly Reynolds

(57) ABSTRACT

The present invention relates to protease variants and methods for obtaining protease variants. The present invention also relates to polynucleotides encoding the variants; nucleic acid constructs, vectors, and host cells comprising the polynucleotides; and methods of using the variants.

7 Claims, No Drawings

Specification includes a Sequence Listing.

US 11,001,786 B2

PROTEASE VARIANTS AND POLYNUCLEOTIDES ENCODING SAME

CROSS-REFERENCE TO RELATED APPLICATIONS

This application is a divisional of U.S. application Ser. No. 15/536,908 filed Jun. 16, 2017, now U.S. Pat. No. 10,590,367, which is a 35 U.S.C. 371 national application of PCT/EP2015/080615 filed Dec. 18, 2015, which claims priority or the benefit under 35 U.S.C. 119 of European application no. 14199407.9 filed Dec. 19, 2014, the contents of which are fully incorporated herein by reference.

REFERENCE TO A SEQUENCE LISTING

This application contains a Sequence Listing in computer readable form, which is incorporated herein by reference.

BACKGROUND OF THE INVENTION

Field of the Invention

The present invention relates to novel protease variants exhibiting alterations relative to the parent protease in one or more properties including: wash performance, detergent stability and/or storage stability. The variants of the invention are suitable for use in cleaning processes and detergent compositions, such as laundry compositions and dish wash compositions, including hand wash and automatic dish wash compositions. The present invention also relates to isolated DNA sequences encoding the variants, expression vectors, host cells, and methods for producing and using the protease variants of the invention.

Description of the Related Art

Enzymes have been used within the detergent industry as part of washing formulations for many decades. Proteases are from a commercial perspective the most relevant enzyme in such formulations, but other enzymes including lipases, amylases, cellulases, hemicellulases or mixtures of enzymes are also often used. To improve the cost and/or the performance of proteases there is an ongoing search for proteases with altered properties, such as increased activity at low temperatures, increased stability, increased specific activity at a given pH, altered $Ca^{2+}$ dependency, increased stability in the presence of other detergent ingredients (e.g. bleach, surfactants etc.) etc. One family of proteases, which are widely used in detergents, are the subtilases. This family has previously been further grouped into 6 different sub-groups by Siezen R J and Leunissen J A M, 1997, Protein Science, 6, 501-523. One of these sub-groups is the Subtilisin family which includes subtilases such as BPN', subtilisin 309 (SAVINASE®, Novozymes NS), subtilisin Carlsberg (AL-CALASE®, Novozymes A/S), subtilisin S41 (a subtilase from the psychrophilic Antarctic *Bacillus* TA41, Davail S et al. 1994, The Journal of Biological Chemistry, 269(26), 99. 17448-17453) and subtilisin S39 (a subtilase from the psychrophilic Antarctic *Bacillus* TA39, Narinx E et al. 1997, Protein Engineering, 10 (11), pp. 1271-1279). The TY-145 protease is a subtilase from *Bacillus* sp. TY-145, NCIMB 40339, which was first described in WO 92/17577 (Novozymes A/S) and in the later application WO2004/067737 (Novozymes A/S) disclosing the three-dimensional structure and the use of protein engineering to alter functionality of a TY-145 subtilase.

SUMMARY OF THE INVENTION

The invention relates to protease variants comprising one or more alterations selected from the group consisting of A1L, A1*, V2I, P3*, S4*, S4C, Q6C, Q18A, L43I, E50Q, N59L, L61K, V62G, G64A, G64S, S65F, Q70T, Q70L, Q70N Q70Y, Q70F, Q70M, Q70A, Q70V, Q97K, G107N, *108aA, N109T, *109aA, N109A, S111I, S111R, Y113S, S114V, S114A, S114F, D126G, D126K, E127R, E127Q, S133H, I137N, M139L, S143R, S144P, S144R, A145E, L149R, L149T, I150L, I150T, I150S, I150V, V162S, V162E, V162Q, V162G, V162F, V162T, V162Y, I164M, S171D, G182A, G182S, Q198E, Q198D, G200C, G200S, A233S, T246M, A267S, S274V, Q275Y, L276I and T297P, wherein the positions corresponds to the positions of SEQ ID NO: 3 and wherein the protease variant has a sequence identity to SEQ ID NO: 3 of at least 60% and the variant has protease activity.

The present invention also relates to isolated polynucleotides encoding the variants; nucleic acid constructs, vectors, and host cells comprising the polynucleotides; and methods of producing the variants.

Overview of Sequences Listed

SEQ ID NO: 1=is the DNA sequence of the TY-145 protease isolated from *Bacillus* sp.

SEQ ID NO: 2=is the amino acid sequence as deduced from SEQ ID NO: 1.

SEQ ID NO: 3=is the amino acid sequence of the mature TY-145 protease.

SEQ ID NO: 4: =is the amino acid sequence of the TY-145 protease+S173P+S175P

SEQ ID NO: 5: =is the amino acid sequence of the TY-145 protease+S173P+S175P+F180Y

Definitions

The term "protease" is defined herein as an enzyme that hydrolyses peptide bonds. It includes any enzyme belonging to the EC 3.4 enzyme group (including each of the thirteen subclasses thereof http://en.wikipedia.org/wiki/Category:EC_3.4). The EC number refers to Enzyme Nomenclature 1992 from NC-IUBMB, Academic Press, San Diego, Calif., including supplements 1-5 published in Eur. J. Biochem. 1994, 223, 1-5; Eur. J. Biochem. 1995, 232, 1-6; Eur. J. Biochem. 1996, 237, 1-5; Eur. J. Biochem. 1997, 250, 1-6; and Eur. J. Biochem. 1999, 264, 610-650; respectively. The term "subtilases" refer to a sub-group of serine protease according to Siezen et al., Protein Engng. 4 (1991) 719-737 and Siezen et al. Protein Science 6 (1997) 501-523. Serine proteases or serine peptidases is a subgroup of proteases characterized by having a serine in the active site, which forms a covalent adduct with the substrate. Further, the subtilases (and the serine proteases) are characterized by having two active site amino acid residues apart from the serine, namely a histidine and an aspartic acid residue. The subtilases may be divided into 6 sub-divisions, i.e. the Subtilisin family, the Thermitase family, the Proteinase K family, the Lantibiotic peptidase family, the Kexin family and the Pyrolysin family. The term "protease activity" means a proteolytic activity (EC 3.4). Proteases of the invention are endopeptidases (EC 3.4.21). For purposes of the present invention, protease activity is determined according to the procedure described in "Materials and Methods" below. The protease variants of the present invention have at least 20%, e.g., at least 40%, at least 50%, at least 60%, at least 70%, at least 80%, at least 90%, at least 95%, or at least 100% of the protease activity of the polypeptide with SEQ ID NO: 3.

The terms "parent", "protease parent" or "precursor protease" mean a protease to which an alteration is made to produce the enzyme variants of the present invention. Thus the parent is a protease having the identical amino acid sequence of said variant but not having the alterations at one or more of said specified positions. It will be understood, that in the present context the expression "having identical amino acid sequence" relates to 100% sequence identity. The parent may be a naturally occurring (wild-type) polypeptide. In a particular embodiment the parent is a protease with at least 60%, at least 61%, at least 62%, at least 63%, at least 64%, at least 65%, at least 70%, at least 72%, at least 73%, at least 74%, at least 75%, at least 80%, at least 81%, at least 82%, at least 83%, at least 84%, at least 85%, at least 90%, at least 91%, at least 92%, at least 93%, at least 94%, at least 95%, at least 96%, at least 97%, at least 98%, at least 99% or 100% identity to the polypeptide shown in SEQ ID NO: 3.

The term "protease variant" means a protease having protease activity comprising an alteration, i.e., a substitution, insertion, and/or deletion, preferably substitution, at one or more (or one or several) positions compared to its parent which is a protease having the identical amino acid sequence of said variant but not having the alterations at one or more of said specified positions. A substitution means a replacement of an amino acid occupying a position with a different amino acid; a deletion means removal of an amino acid occupying a position; and an insertion means adding amino acids e.g. 1 to 10 amino acids, preferably 1-3 amino acids adjacent to an amino acid occupying a position. Preferably the variant is modified by the hand of man. In one aspect, the variant is at least 1% pure, e.g., at least 5% pure, at least 10% pure, at least 20% pure, at least 40% pure, at least 60% pure, at least 80% pure, and at least 90% pure, as determined by SDS PAGE.

The term "isolated polynucleotide" means a polynucleotide that is modified by the hand of man. In one aspect, the isolated polynucleotide is at least 1% pure, e.g., at least 5% pure, at least 10% pure, at least 20% pure, at least 40% pure, at least 60% pure, at least 80% pure, at least 90% pure, and at least 95% pure, as determined by agarose electrophoresis. The polynucleotides may be of genomic, cDNA, RNA, semisynthetic, synthetic origin, or any combinations thereof.

The term "allelic variant" means any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

The term "substantially pure variant" means a preparation that contains at most 10%, at most 8%, at most 6%, at most 5%, at most 4%, at most 3%, at most 2%, at most 1%, and at most 0.5% by weight of other polypeptide material with which it is natively or recombinantly associated. Preferably, the variant is at least 92% pure, e.g., at least 94% pure, at least 95% pure, at least 96% pure, at least 97% pure, at least 98% pure, at least 99%, at least 99.5% pure, and 100% pure by weight of the total polypeptide material present in the preparation. The variants of the present invention are preferably in a substantially pure form. This can be accomplished, for example, by preparing the variant by well-known recombinant methods or by classical purification methods.

The term "wild-type protease" means a protease expressed by a naturally occurring organism, such as a bacterium, archaea, yeast, fungus, plant or animal found in nature. An example of a wild-type protease is the TY-145 protease.

The term "mature polypeptide" means a polypeptide in its final form following translation and any post-translational modifications, such as N-terminal processing, C-terminal truncation, glycosylation, phosphorylation, etc. In one aspect, the mature polypeptide corresponds to the amino acid sequence SEQ ID NO: 3.

The term "mature polypeptide coding sequence" means a polynucleotide that encodes a mature polypeptide having protease activity. In one aspect, the mature polypeptide coding sequence is nucleotides 331 to 1263 of SEQ ID NO: 1 based on the SignalP (Nielsen et al., 1997, Protein Engineering 10: 1-6)] that predicts nucleotides 1 to 81 of SEQ ID NO: 1 is the signal peptide.

The term "cDNA" means a DNA molecule that can be prepared by reverse transcription from a mature, spliced, mRNA molecule obtained from a prokaryotic or eukaryotic cell. A cDNA lacks intron sequences that may be present in the corresponding genomic DNA. The initial, primary RNA transcript is a precursor to mRNA that is processed through a series of steps, including splicing, before appearing as mature spliced mRNA.

The term "coding sequence" means a polynucleotide, which directly specifies the amino acid sequence of its polypeptide product. The boundaries of the coding sequence are generally determined by an open reading frame, which usually begins with the ATG start codon or alternative start codons such as GTG and TTG and ends with a stop codon such as TAA, TAG, and TGA. The coding sequence may be a DNA, cDNA, synthetic, or recombinant polynucleotide.

The term "nucleic acid construct" means a nucleic acid molecule, either single- or double-stranded, which is isolated from a naturally occurring gene or is modified to contain segments of nucleic acids in a manner that would not otherwise exist in nature or which is synthetic. The term nucleic acid construct is synonymous with the term "expression cassette" when the nucleic acid construct contains the control sequences required for expression of a coding sequence of the present invention.

The term "operably linked" means a configuration in which a control sequence is placed at an appropriate position relative to the coding sequence of a polynucleotide such that the control sequence directs the expression of the coding sequence.

The term "control sequences" means all components necessary for the expression of a polynucleotide encoding a variant of the present invention. Each control sequence may be native or foreign to the polynucleotide encoding the variant or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a variant.

The term "expression" includes any step involved in the production of the variant including, but not limited to, transcription, post-transcriptional modification, translation, post-translational modification, and secretion.

The term "expression vector" means a linear or circular DNA molecule that comprises a polynucleotide encoding a variant and is operably linked to additional nucleotides that provide for its expression.

The term "transcription promoter" is used for a promoter which is a region of DNA that facilitates the transcription of a particular gene. Transcription promoters are typically located near the genes they regulate, on the same strand and upstream (towards the 5' region of the sense strand).

The term "transcription terminator" is used for a section of the genetic sequence that marks the end of gene or operon on genomic DNA for transcription.

The term "host cell" means any cell type that is susceptible to transformation, transfection, transduction, and the like with a nucleic acid construct or expression vector comprising a polynucleotide of the present invention. The term "host cell" encompasses any progeny of a parent cell that is not identical to the parent cell due to mutations that occur during replication.

The relatedness between two amino acid sequences or between two nucleotide sequences is described by the parameter "sequence identity". For purposes of the present invention, the degree of sequence identity between two amino acid sequences is determined using the Needleman-Wunsch algorithm (Needleman and Wunsch, 1970, J. Mol. Biol. 48: 443-453) as implemented in the Needle program of the EMBOSS package (EMBOSS: The European Molecular Biology Open Software Suite, Rice et al., 2000, Trends Genet. 16: 276-277), preferably version 3.0.0 or later. The optional parameters used are gap open penalty of 10, gap extension penalty of 0.5, and the EBLOSUM62 (EMBOSS version of BLOSUM62) substitution matrix. The output of Needle labeled "longest identity" (obtained using the -nobrief option) is used as the percent identity and is calculated as follows:

(Identical Residues×100)/(Length of Alignment–
Total Number of Gaps in Alignment)

The term "high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 2×SSC, 0.2% SDS at 65° C.

The term "very high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 2×SSC, 0.2% SDS at 70° C.

The term "medium stringency conditions" means for probes of at least 100 nucleotides in length, prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 2×SSC, 0.2% SDS at 55° C.

The term "medium-high stringency conditions" means for probes of at least 100 nucleotides in length, prehybridization and hybridization at 42° C. in 5×SSPE, 0.3% SDS, 200 micrograms/ml sheared and denatured salmon sperm DNA, and either 35% formamide, following standard Southern blotting procedures for 12 to 24 hours. The carrier material is finally washed three times each for 15 minutes using 2×SSC, 0.2% SDS at 60° C.

The term "low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 2×SSC, 0.2% SDS at 50° C.

The term "very low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 2×SSC, 0.2% SDS at 45° C.

The term "improved property" means a characteristic associated with a variant that is improved compared to the parent or compared to a protease with SEQ ID NO: 3, or compared to a protease having the identical amino acid sequence of said variant but not having the alterations at one or more of said specified positions. Such improved properties include, but are not limited to, wash performance, protease activity, thermal activity profile, thermostability, pH activity profile, pH stability, substrate/cofactor specificity, improved surface properties, substrate specificity, product specificity, increased stability, improved stability under storage conditions, and chemical stability. The term "improved protease activity" is defined herein as an altered protease activity (as defined above) e.g. by increased protein conversion of a protease variant displaying an alteration of the activity relative (or compared) to the activity of the parent protease, or compared to a protease with SEQ ID NO: 3, or relative to a protease having the identical amino acid sequence of said variant but not having the alterations at one or more of said specified positions.

The term "stability" includes storage stability and stability during use, e.g. during a wash process and reflects the stability of the protease variant according to the invention as a function of time e.g. how much activity is retained when the protease variant is kept in solution in particular in a detergent solution. The stability is influenced by many factors e.g. pH, temperature, detergent composition e.g. amount of builder, surfactants etc. The protease stability may be measured using the assay described in example 3. The term "improved stability" or "increased stability" is defined herein as a variant protease displaying an increased stability in solutions, relative to the stability of the parent protease, relative to a protease having the identical amino acid sequence of said variant but not having the alterations at one or more of said specified positions or relative to SEQ ID NO: 3. The terms "improved stability" and "increased stability" includes "improved chemical stability", "detergent stability" or "improved detergent stability.

The term "improved chemical stability" is defined herein as a variant enzyme displaying retention of enzymatic activity after a period of incubation in the presence of a chemical or chemicals, either naturally occurring or synthetic, which reduces the enzymatic activity of the parent enzyme. Improved chemical stability may also result in variants being more able to catalyze a reaction in the presence of such chemicals. In a particular aspect of the invention the improved chemical stability is an improved stability in a detergent, in particular in a liquid detergent.

The term "detergent stability" or "improved detergent stability is in particular an improved stability of the protease activity when a protease variant of the present invention is mixed into a liquid detergent formulation, especially into a liquid detergent formulation according to table 1 and then stored at temperatures between 15 and 50° C., e. g. 20° C., 30° C. or 40° C.

The term "improved thermal activity" means a variant displaying an altered temperature-dependent activity profile at a specific temperature relative to the temperature-dependent activity profile of the parent or relative to a protease with SEQ ID NO: 3. The thermal activity value provides a measure of the variant's efficiency in enhancing catalysis of a hydrolysis reaction over a range of temperatures.

The term "improved wash performance" is defined herein as a protease variant according to the invention displaying an improved wash performance relative to the wash performance of the parent protease, relative to a protease with SEQ ID NO: 3 or relative to a protease having the identical amino acid sequence of said variant but not having the alterations at one or more of said specified positions e.g. by increased stain removal. The term "wash performance" includes wash performance in laundry but also e.g. in dish wash. The wash performance may be quantified as described under the definition of "wash performance" herein. The term "detergent composition", includes unless otherwise indicated, granular or powder-form all-purpose or heavy-duty washing agents, especially cleaning detergents; liquid, gel or paste-form all-purpose washing agents, especially the so-called heavy-duty liquid (HDL) types; liquid fine-fabric detergents; hand dishwashing agents or light duty dishwashing agents, especially those of the high-foaming type; machine dishwashing agents, including the various tablet, granular, liquid and rinse-aid types for household and institutional use; liquid cleaning and disinfecting agents, including antibacterial hand-wash types, cleaning bars, soap bars, mouthwashes, denture cleaners, car or carpet shampoos, bathroom cleaners; hair shampoos and hair-rinses; shower gels, foam baths; metal cleaners; as well as cleaning auxiliaries such as bleach additives and "stain-stick" or pre-treat types. The terms "detergent composition" and "detergent formulation" are used in reference to mixtures which are intended for use in a wash medium for the cleaning of soiled objects. In some embodiments, the term is used in reference to laundering fabrics and/or garments (e.g., "laundry detergents"). In alternative embodiments, the term refers to other detergents, such as those used to clean dishes, cutlery, etc. (e.g., "dishwashing detergents"). It is not intended that the present invention be limited to any particular detergent formulation or composition. The term "detergent composition" is not intended to be limited to compositions that contain surfactants. It is intended that in addition to the variants according to the invention, the term encompasses detergents that may contain, e.g., surfactants, builders, chelators or chelating agents, bleach system or bleach components, polymers, fabric conditioners, foam boosters, suds suppressors, dyes, perfume, tannish inhibitors, optical brighteners, bactericides, fungicides, soil suspending agents, anti corrosion agents, enzyme inhibitors or stabilizers, enzyme activators, transferase(s), hydrolytic enzymes, oxido reductases, bluing agents and fluorescent dyes, antioxidants, and solubilizers.

The term "fabric" encompasses any textile material. Thus, it is intended that the term encompass garments, as well as fabrics, yarns, fibers, non-woven materials, natural materials, synthetic materials, and any other textile material.

The term "textile" refers to woven fabrics, as well as staple fibers and filaments suitable for conversion to or use as yarns, woven, knit, and non-woven fabrics. The term encompasses yarns made from natural, as well as synthetic (e.g., manufactured) fibers. The term, "textile materials" is a general term for fibers, yarn intermediates, yarn, fabrics, and products made from fabrics (e.g., garments and other articles).

The term "non-fabric detergent compositions" includes non-textile surface detergent compositions, including but not limited to compositions for hard surface cleaning, such as dishwashing detergent compositions including manual dish wash compositions, oral detergent compositions, denture detergent compositions, and personal cleansing compositions.

The term "effective amount of enzyme" refers to the quantity of enzyme necessary to achieve the enzymatic activity required in the specific application, e.g., in a defined detergent composition. Such effective amounts are readily ascertained by one of ordinary skill in the art and are based on many factors, such as the particular enzyme used, the cleaning application, the specific composition of the detergent composition, and whether a liquid or dry (e.g., granular, bar) composition is required, and the like. The term "effective amount" of a protease variant refers to the quantity of protease variant described hereinbefore that achieves a desired level of enzymatic activity, e.g., in a defined detergent composition.

The terms "water hardness" or "degree of hardness" or "dH" or "° dH" as used herein refer to German degrees of hardness. One degree is defined as 10 milligrams of calcium oxide per liter of water.

The term "relevant washing conditions" is used herein to indicate the conditions, particularly washing temperature, time, washing mechanics, detergent concentration, type of detergent and water hardness, actually used in households in a detergent market segment.

The term "adjunct materials" means any liquid, solid or gaseous material selected for the particular type of detergent composition desired and the form of the product (e.g., liquid, granule, powder, bar, paste, spray, tablet, gel, or foam composition), which materials are also preferably compatible with the protease variant enzyme used in the composition. In some embodiments, granular compositions are in "compact" form, while in other embodiments, the liquid compositions are in a "concentrated" form.

The term "stain removing enzyme" as used herein, describes an enzyme that aids the removal of a stain or soil from a fabric or a hard surface. Stain removing enzymes act on specific substrates, e.g., protease on protein, amylase on starch, lipase and cutinase on lipids (fats and oils), pectinase on pectin and hemicellulases on hemicellulose. Stains are often depositions of complex mixtures of different components which either results in a local discolouration of the material by itself or which leaves a sticky surface on the object which may attract soils dissolved in the washing liquor thereby resulting in discolouration of the stained area. When an enzyme acts on its specific substrate present in a stain the enzyme degrades or partially degrades its substrate thereby aiding the removal of soils and stain components associated with the substrate during the washing process. For example, when a protease acts on a blood stain it degrades the protein components in the blood.

The term "reduced amount" means in this context that the amount of the component is smaller than the amount which would be used in a reference process under otherwise the same conditions.

The term "low detergent concentration" system includes detergents where less than about 800 ppm of detergent components is present in the wash water. Asian, e.g., Japanese detergents are typically considered low detergent concentration systems.

The term "medium detergent concentration" system includes detergents wherein between about 800 ppm and about 2000 ppm of detergent components is present in the wash water. North American detergents are generally considered to be medium detergent concentration systems.

The term "high detergent concentration" system includes detergents wherein greater than about 2000 ppm of detergent components is present in the wash water. European detergents are generally considered to be high detergent concentration systems.

Conventions for Designation of Variants

For purposes of the present invention, the mature polypeptide disclosed in SEQ ID NO: 3 is used to determine the corresponding amino acid residue in another protease. The amino acid sequence of another protease is aligned with the mature polypeptide disclosed in SEQ ID NO: 3, and based on the alignment, the amino acid position number corresponding to any amino acid residue in the mature polypeptide disclosed in SEQ ID NO: 3 is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used are gap open penalty of 10, gap extension penalty of 0.5, and the EBLOSUM62 (EMBOSS version of BLOSUM62) substitution matrix.

Identification of the corresponding amino acid residue in another protease can be determined by an alignment of multiple polypeptide sequences using several computer programs including, but not limited to, MUSCLE (multiple sequence comparison by log-expectation; version 3.5 or later; Edgar, 2004, *Nucleic Acids Research* 32: 1792-1797), MAFFT (version 6.857 or later; Katoh and Kuma, 2002, *Nucleic Acids Research* 30: 3059-3066; Katoh et al., 2005, *Nucleic Acids Research* 33: 511-518; Katoh and Toh, 2007, *Bioinformatics* 23: 372-374; Katoh et al., 2009, *Methods in Molecular Biology* 537: 39-64; Katoh and Toh, 2010, *Bioinformatics* 26: 1899-1900), and EMBOSS EMMA employing ClustalW (1.83 or later; Thompson et al., 1994, *Nucleic Acids Research* 22: 4673-4680), using their respective default parameters.

When the other enzyme has diverged from the mature polypeptide of SEQ ID NO: 3 such that traditional sequence-based comparison fails to detect their relationship (Lindahl and Elofsson, 2000, *J. Mol. Biol.* 295: 613-615), other pairwise sequence comparison algorithms can be used. Greater sensitivity in sequence-based searching can be attained using search programs that utilize probabilistic representations of polypeptide families (profiles) to search databases. For example, the PSI-BLAST program generates profiles through an iterative database search process and is capable of detecting remote homologs (Atschul et al., 1997, *Nucleic Acids Res.* 25: 3389-3402). Even greater sensitivity can be achieved if the family or superfamily for the polypeptide has one or more representatives in the protein structure databases. Programs such as GenTHREADER (Jones, 1999, *J. Mol. Biol.* 287: 797-815; McGuffin and Jones, 2003, *Bioinformatics* 19: 874-881) utilize information from a variety of sources (PSI-BLAST, secondary structure prediction, structural alignment profiles, and solvation potentials) as input to a neural network that predicts the structural fold for a query sequence. Similarly, the method of Gough et al., 2000, *J. Mol. Biol.* 313: 903-919, can be used to align a sequence of unknown structure with the superfamily models present in the SCOP database. These alignments can in turn be used to generate homology models for the polypeptide, and such models can be assessed for accuracy using a variety of tools developed for that purpose.

For proteins of known structure, several tools and resources are available for retrieving and generating structural alignments. For example the SCOP super families of proteins have been structurally aligned, and those alignments are accessible and downloadable. Two or more protein structures can be aligned using a variety of algorithms such as the distance alignment matrix (Holm and Sander, 1998, *Proteins* 33: 88-96) or combinatorial extension (Shindyalov and Bourne, 1998, *Protein Engineering* 11: 739-747), and implementation of these algorithms can additionally be utilized to query structure databases with a structure of interest in order to discover possible structural homologs (e.g., Holm and Park, 2000, *Bioinformatics* 16: 566-567).

In describing the variants of the present invention, the nomenclature described below is adapted for ease of reference. The accepted IUPAC single letter or three letters amino acid abbreviations are employed. Amino acid positions are indicated with $\#_1$, $\#_2$, etc.

Substitutions: For an amino acid substitution, the following nomenclature is used: Original amino acid, position, substituted amino acid. Accordingly, the substitution of serine at position $\#_1$ with tryptophan is designated as "Ser $\#_1$Trp" or "S $\#_1$W". Multiple mutations are separated by addition marks ("+") or by commas (,), e.g., "Ser $\#_1$Trp+Ser $\#_2$Pro" or S $\#_1$W, S $\#_2$P, representing substitutions at positions $\#_1$ and $\#_2$ of serine (S) with tryptophan (W) and proline (P), respectively. If more than one amino acid may be substituted in a given position these are listed in brackets, such as [X] or {X}. Thus if both Trp and Lys according to the invention may be substituted instead of the amino acid occupying at position $\#_1$ this is indicated as X $\#_1$ {W, K} or X $\#_2$ [W, K] where the X indicate the amino acid residues of different proteases which according to the invention may be parent e.g. a protease with SEQ ID NO 3. Thus in some cases the variants are represented as $\#_1$ {W, K} or X $\#_2$P indicating that the amino acids to be substituted vary depending on the parent. As SEQ ID NO 3 is used for numbering the substitutions according to the present application may be indicated with the amino acid present in the corresponding position in SEQ ID NO 3.

Deletions: For an amino acid deletion, the following nomenclature is used: Original amino acid, position, *. Accordingly, the deletion of serine at position $\#_1$ is designated as "Ser $\#_1$*" or "S $\#_1$*". Multiple deletions are separated by addition marks ("+") or commas, e.g., "Ser $\#_1$*+Ser $\#_2$*" or "S $\#_1$*, S $\#_2$*".

Insertions: The insertion of an additional amino acid residue such as e.g. a lysine after G $\#_1$ may be indicated by: Gly $\#_1$GlyLys or G $\#_1$GK. Alternatively insertion of an additional amino acid residue such as lysine after G #1 may be indicated by: *$\#_1$aL. When more than one amino acid residue is inserted, such as e.g. a Lys, and Ala after #1 this may be indicated as: Gly $\#_1$GlyLysAla or G $\#_1$GKA. In such cases, the inserted amino acid residue(s) may also be numbered by the addition of lower case letters to the position number of the amino acid residue preceding the inserted amino acid residue(s), in this example: *$\#_1$aK *$\#_1$bA.

Multiple alterations: Variants comprising multiple alterations are separated by addition marks ("+") or by commas (,), e.g., "Ser $\#_1$Trp+Ser $\#_2$Pro" or "S $\#_1$W, S $\#_2$P" representing a substitution of serine at positions $\#_1$ and $\#_2$ with tryptophan and proline, respectively as described above.

Different alterations: Where different alterations can be introduced at a position, the different alterations are separated by a comma, e.g., "Ser #₁Trp, Lys" or S #₁W, K represents a substitution of serine at position #₁ with tryptophan or lysine. Thus, "Ser #₁Trp, Lys+Ser #₂Asp" designates the following variants: "Ser #₁Trp+Ser #₂Pro", "Ser #₁Lys+Ser #₂Pro" or S #₁W, K+S #₂D.

DETAILED DESCRIPTION OF THE INVENTION

The present invention provides novel protease variants obtained from Bacillus sp., in particular, Bacillus sp. TY-145. The protease variants of the invention have at least 60%, at least 70%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95% identity, at least 96%, at least 97%, at least 98%, or at least 99%, e. g. at least 99.1%, at least 99.2%, at least 99.3%, at least 99.4%, at least 99.5%, at least 99.6, but less than 100% sequence identity to SEQ ID NO 3 and comprise a substitution of at least one amino acid position compared to the protease with SEQ ID NO: 3, wherein the at least one amino acid position selected from the group consisting of 1, 2, 3, 4, 6, 18, 43, 50, 59, 61, 62, 64, 65, 70, 107, 108, 109, 111, 113, 114, 126, 127, 133, 137, 139, 143, 144, 145, 149, 150, 162, 164, 171, 182, 198, 200, 233, 246, 267, 274, 275 and 276. One embodiment of the invention relates to protease variants having at least 60% identity to SEQ ID NO 3, having proteolytic activity and comprising one or more alterations selected from the group consisting of A1L, A1*, V2I, P3*, S4*, S4C, Q6C, Q18A, L43I, E50Q, N59L, L61K, V62G, G64A, G64S, S65F, Q70T, Q70L, Q70N Q70Y, Q70F, Q70M, Q70A, Q70V, Q97K, G107N, *108aA, N109T, *109aA, N109A, S111I, S111R, Y113S, S114V, S114A, S114F, D126G, D126K, E127R, E127Q, S133H, I137N, M139L, S143R, S144P, S144R, A145E, L149R, L149T, I150L, I150T, I150S, I150V, V162S, V162E, V162Q, V162G, V162F, V162T, V162Y, I164M, S171D, G182A, G182S, Q198E, Q198D, G200C, G200S, A233S, T246M, A267S, S274V, Q275Y, L276I and T297P, wherein each position corresponds to the position of the polypeptide of SEQ ID NO: 3. In a preferred embodiment the protease variant comprises one or more alterations selected from the group consisting of A1L, A1*, V2I, P3*, S4*, S4C, Q6C, Q18A, L43I, E50Q, N59L, L61K, V62G, G64A, G64S, S65F, Q70T, Q70L, Q70N Q70Y, Q70F, Q70M, Q70A, Q70V, Q97K, G107N, *108aA, N109T, *109aA, N109A, S111I, S111R, Y113S, S114V, S114A, S114F, D126G, D126K, E127R, E127Q, S133H, I137N, M139L, S143R, S144P, S144R, A145E, L149R, L149T, I150L, I150T, I150S, I150V, V162S, V162E, V162Q, V162G, V162F, V162T, V162Y, I164M, S171D, G182A, G182S, Q198E, Q198D, G200C, G200S, A233S, T246M, A267S, S274V, Q275Y, L276I and T297P, wherein each position corresponds to the position of the polypeptide of SEQ ID NO: 3 and wherein the variant has at least 60%, at least 70%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95% identity, at least 96%, at least 97%, at least 98%, or at least 99%, e. g. at least 99.1%, at least 99.2%, at least 99.3%, at least 99.4%, at least 99.5%, at least 99.6, but less than 100%, sequence identity to SEQ ID NO: 3.

The protease variants according to the invention have improved properties compared to the parent protease e.g. a protease with SEQ ID NO 3. Preferably the protease variants according to the invention have improve stability such as improve stability in detergents, such as increased storage stability, in wash stability and/or chemical stability.

The protease variants comprising one or more alterations selected from the group consisting of A1L, A1*, V2I, P3*, S4*, S4C, Q6C, Q18A, L43I, E50Q, N59L, L61K, V62G, G64A, G64S, S65F, Q70T, Q70L, Q70N Q70Y, Q70F, Q70M, Q70A, Q70V, Q97K, G107N, *108aA, N109T, *109aA, N109A, S111I, S111R, Y113S, S114V, S114A, S114F, D126G, D126K, E127R, E127Q, S133H, I137N, M139L, S143R, S144P, S144R, A145E, L149R, L149T, I150L, I150T, I150S, I150V, V162S, V162E, V162Q, V162G, V162F, V162T, V162Y, I164M, S171D, G182A, G182S, Q198E, Q198D, G200C, G200S, A233S, T246M, A267S, S274V, Q275Y, L276I and T297P, were generated and tested for stability in detergent as described in "Material and Methods" example 3. The inventors show that one or more alterations of one or more amino acid at a position corresponding to positions 1, 2, 3, 4, 6, 18, 43, 59, 61, 62, 64, 65, 70, 108, 109, 150, 162, 164, 171, 182, 198, 200, 233, 246, 267, 274, 275 or 276 of the mature polypeptide SEQ ID NO: 3 significantly improved the detergent stability compared to a protease having the identical amino acid sequence of said variant but not having a substitution at one or more of said specified positions or compared to a protease with SEQ ID NO: 3.

Such a protease variant having improved stability is in a preferred embodiment a variant selected from the group consisting:

S27K, Q70A, I121V, E127Q, S173P, G174K, S175P, F180Y, G182A, L184F, Q197K, Q198E, T297P;
S27K, *108aA, N109S, V162T, S173P, G174K, S175A, F180Y, G182A, L184F, 0197K, Q198E, T297P;
S27K, I121V, S173P, G174R, S175A, F180Y, G182A, L184Y, Q197K, Q198E, S270V, T297;
S27K, N59L, T67V, I121V, S173P, G174K, S175P, F180Y, G182A, L184Y, Q197K, Q198E, T 297P;
S27K, N109R, S111E, V162T, S173P, G174K, S175A, F180Y, G182A, L184F, Q197K, Q198E, T297P;
S27K, N87K, S171D, S173P, G174R, S175P, G182A, L184F, Q198E, N199R, T297P;
S27K, Q70A, S171D, S173P, G174R, S175P, F180Y, G182A, L184F, Q198E, N199K, S274V, T297P;
S27K, *108aA, N109S, S171D, S173P, G174R, S175A, F180Y, G182A, L184F, Q198E, N199K, T297P;
S27K, S171E, S173P, G174K, S175P, F180Y, G182A, L184F, Q198E, N199K, T297P;
S27K, S173P, G174K, S175P, F180Y, G182A, L184F, Q198E, V286R, T297P;
S27K, N109R, S111E, S171E, S173P, G174K, S175P, F180Y, G182A, L184F, Q198E, N199K, T297P;
S27K, Q70N, I121V, S173P, G174K, S175P, G182A, L184F, Q198E, T297P; S27K, N109K, S111E, S171E, S173P, G174K, S175P, F180Y, G182A, L184F, Q198E, N199K, T297P;
S27K, V162T, S171D, S173P, G174R, S175A, F180Y, G182A, L184F, Q197K, Q198E, T297P and
S27K, S171D, S173P, G174R, S175A, F180Y, G182A, L184F, Q198E, N199K, T297P.

Surprisingly the protease variants according to the invention may in addition to improved stability also have improved wash performance. Thus in a preferred embodiment the protease variants according to the invention have improved the detergent stability and/or improved wash performance compared to a protease having the identical amino acid sequence of said variant but not having a substitution at one or more of said specified positions or compared to a protease with SEQ ID NO:3. The present invention provides proteases stabilized by introducing specific alterations selected from the group consisting of A1L, A1*, V2I, P3*, 84*, S4C, Q6C, Q18A, L43I, E50Q, N59L, L61K, V62G, G64A, G64S, S65F, Q70T, Q70L, Q70N Q70Y, Q70F, Q70M, Q70A, Q70V, Q97K, G107N, *108aA, N109T, *109aA, N109A, S111I, S111R, Y113S, S114V, S114A, S114F, D126G, D126K, E127R, E127Q, S133H, I137N, M139L, S143R, S144P, S144R, A145E, L149R, L149T, I150L, I150T, I150S, I150V, V162S, V162E, V162Q, V162G, V162F, V162T, V162Y, I164M, S171D, G182A, G182S, Q198E, Q198D, G200C, G200S, A233S, T246M, A267S, S274V, Q275Y, L276I and T297P, wherein each position corresponds to the position of the polypeptide of SEQ ID NO: 3. The stability of the protease variants of the invention is measured as described in example 3 herein. An embodiment of the invention relates to protease variants having at least 60% identity to SEQ ID NO 3, having proteolytic activity and comprising one or more alterations selected from the group consisting of A1L, A1*, V2I, P3*, S4*, S4C, Q6C, Q18A, L43I, E50Q, N59L, L61K, V62G, G64A, G64S, S65F, Q70T, Q70L, Q70N Q70Y, Q70F, Q70M, Q70A, Q70V, Q97K, G107N, *108aA, N109T, *109aA, N109A, S111I, S111R, Y113S, S114V, S114A, S114F, D126G, D126K, E127R, E127Q, S133H, I137N, M139L, S143R, S144P, S144R, A145E, L149R, L149T, I150L, I150T, I150S, I150V, V162S, V162E, V162Q, V162G, V162F, V162T, V162Y, I164M, S171D, G182A, G182S, Q198E, Q198D, G200C, G200S, A233S, T246M, A267S, S274V, Q275Y, L276I and T297P, wherein each position corresponds to the position of the polypeptide of SEQ ID NO: 3 and wherein the protease variants have at least 10% more, such as at least 20%, at least 25%, at least 30%, at least 35%, at least 40%, at least 45%, at least 50%, at least 55% at least 60%, at least 65%, at least 70%, at least 75%, at least 80%, at least 85%, at least 90% or at least 95% residual activity compared to the parent or compared to SEQ ID NO 3. The residual activity or t½ is described in example 3 herein.

In some further embodiments, the present invention relates to protease variants having at least 60% sequence identity to SEQ ID NO 3, wherein when said variant having at least one improved property compared to SEQ ID NO 3 when tested in a relevant assay. In one embodiment, the property is stability, such as storage stability in detergent in another embodiment the property is wash performance.

In one embodiment, the protease variants according to the invention have one or more improved property relative to the parent measured as an Improvement Factor (IF) that is greater than 1.0, wherein the improved property is stability such as stability in detergent.

In one embodiment, the variants according to the invention have an Improvement Factor (IF) which is greater than 1.0 when tested in a relevant assay as described in example 2.

In some aspects, the variants according to the invention have an Improvement Factor (IF) which is at least 1.1; 1.2; 1.3; 1.4; 1.5; 1.6; 1.7; 1.8; 1.9; 2.0; 2.1; 2.2; 2.3; 2.4; 2.5; 2.6; 2.7; 2.8; 2.9; 3.0; 3.1; 3.2; 3.3; 3.4; 3.5; 3.6; 3.7; 3.8; 3.9; 4.0; 4.1; 4.2; 4.3; 4.4; 4.5; 4.6; 4.7; 4.8; 4.9; 5.0; 5.1; 5.2; 5.3; 5.4; 5.5, 5.6, 5.7, 5.8, 5.9 or 6.0.

A particular embodiment of the invention relates to protease variants having at least 60% identity to SEQ ID NO 3, having proteolytic activity and comprising one or more alterations selected from the group consisting A1L, A1*, V2I, P3*, S4*, S4C, Q6C, Q18A, L43I, E50Q, N59L, L61K, V62G, G64A, G64S, S65F, Q70T, Q70L, Q70N Q70Y, Q70F, Q70M, Q70A, Q70V, Q97K, G107N, *108aA, N109T, *109aA, N109A, S111I, S111R, Y113S, S114V, S114A, S114F, D126G, D126K, E127R, E127Q, S133H, I137N, M139L, S143R, S144P, S144R, A145E, L149R, L149T, I150L, I150T, I150S, I150V, V162S, V162E, V162Q, V162G, V162F, V162T, V162Y, I164M, S171D, G182A, G182S, Q198E, Q198D, G200C, G200S, A233S, T246M, A267S, S274V, Q275Y, L276I and T297P, wherein each position corresponds to the position of the polypeptide of SEQ ID NO: 3 and wherein the protease variants have at least 10% more, such as at least 20%, at least 25%, at least 30%, at least 35%, at least 40%, at least 45%, at least 50%, at least 55% at least 60%, at least 65%, at least 70%, at least 75%, at least 80%, at least 85%, at least 90% or at least 95% residual activity compared to the proteases with SEQ ID NO 4 or SEQ ID NO 5.

In another aspect, the protease variant according to the invention comprises an alteration at one or more (e.g., several) positions corresponding to positions, wherein the at least one amino acid position selected from the group consisting of 1, 2, 3, 4, 6, 18, 43, 50, 59, 61, 62, 64, 65, 70, 107, 108, 109, 111, 113, 114, 126, 127, 133, 137, 139, 143, 144, 145, 149, 150, 162, 164, 171, 182, 198, 200, 233, 246, 267, 274, 275 or 276. In another aspect, a variant comprises an alteration at two positions corresponding to any of positions 1, 2, 3, 4, 6, 18, 43, 50, 59, 61, 62, 64, 65, 70, 107, 108, 109, 111, 113, 114, 126, 127, 133, 137, 139, 143, 144, 145, 149, 150, 162, 164, 171, 182, 198, 200, 233, 246, 267, 274, 275 or 276. In another aspect, a variant comprises an alteration at three positions corresponding to any of positions 1, 2, 3, 4, 6, 18, 43, 50, 59, 61, 62, 64, 65, 70, 107, 108, 109, 111, 113, 114, 126, 127, 133, 137, 139, 143, 144, 145, 149, 150, 162, 164, 171, 182, 198, 200, 233, 246, 267, 274, 275 or 276. In another aspect, a variant comprises an alteration at each position corresponding to positions 1, 2, 3, 4, 6, 18, 43, 50, 59, 61, 62, 64, 65, 70, 107, 108, 109, 111, 113, 114, 126, 127, 133, 137, 139, 143, 144, 145, 149, 150, 162, 164, 171, 182, 198, 200, 233, 246, 267, 274, 275 or 276.

One aspect of the invention relates to a protease variant of a protease parent wherein parent protease is a polypeptide with SEQ ID NO: 3, SEQ ID NO 4 or SEQ ID NO 5, wherein the protease variant comprises or consists of the substitution A1L compared to the parent protease and wherein the protease variant has at least 60% identity to the polypeptide with SEQ ID NO: 3.

One aspect of the invention relates to a protease variant of a protease parent wherein parent protease is a polypeptide with SEQ ID NO: 3, SEQ ID NO 4 or SEQ ID NO 5, wherein the protease variant comprises or consists of the deletion A1* compared to the parent protease and wherein the protease variant has at least 60% identity to the polypeptide with SEQ ID NO: 3.

One aspect of the invention relates to a protease variant of a protease parent wherein parent protease is a polypeptide with SEQ ID NO: 3, SEQ ID NO 4 or SEQ ID NO 5, wherein the protease variant comprises or consists of the substitution V2I compared to the parent protease and wherein the protease variant has at least 60% identity to the polypeptide with SEQ ID NO: 3.

One aspect of the invention relates to a protease variant of a protease parent wherein parent protease is a polypeptide with SEQ ID NO: 3, SEQ ID NO 4 or SEQ ID NO 5, wherein the protease variant comprises or consists of the deletion P3* compared to the parent protease and wherein the protease variant has at least 60% identity to the polypeptide with SEQ ID NO: 3.

One aspect of the invention relates to a protease variant of a protease parent wherein parent protease is a polypeptide with SEQ ID NO: 3, SEQ ID NO 4 or SEQ ID NO 5, wherein the protease variant comprises or consists of the deletion S4* compared to the parent protease and wherein the protease variant has at least 60% identity to the polypeptide with SEQ ID NO: 3.

One aspect of the invention relates to a protease variant of a protease parent wherein parent protease is a polypeptide with SEQ ID NO: 3, SEQ ID NO 4 or SEQ ID NO 5, wherein the protease variant comprises or consists of the substitution S4C compared to the parent protease and wherein the protease variant has at least 60% identity to the polypeptide with SEQ ID NO: 3.

One aspect of the invention relates to a protease variant of a protease parent wherein parent protease is a polypeptide with SEQ ID NO: 3, SEQ ID NO 4 or SEQ ID NO 5, wherein the protease variant comprises or consists of the substitution Q6C compared to the parent protease and wherein the protease variant has at least 60% identity to the polypeptide with SEQ ID NO: 3.

One aspect of the invention relates to a protease variant of a protease parent wherein parent protease is a polypeptide with SEQ ID NO: 3, SEQ ID NO 4 or SEQ ID NO 5, wherein the protease variant comprises or consists of the substitution Q18A compared to the parent protease and wherein the protease variant has at least 60% identity to the polypeptide with SEQ ID NO: 3.

One aspect of the invention relates to a protease variant of a protease parent wherein parent protease is a polypeptide with SEQ ID NO: 3, SEQ ID NO 4 or SEQ ID NO 5, wherein the protease variant comprises or consists of the substitution L43I compared to the parent protease and wherein the protease variant has at least 60% identity to the polypeptide with SEQ ID NO: 3.

One aspect of the invention relates to a protease variant of a protease parent wherein parent protease is a polypeptide with SEQ ID NO: 3, SEQ ID NO 4 or SEQ ID NO 5, wherein the protease variant comprises or consists of the substitution N59L compared to the parent protease and wherein the protease variant has at least 60% identity to the polypeptide with SEQ ID NO: 3.

One aspect of the invention relates to a protease variant of a protease parent wherein parent protease is a polypeptide with SEQ ID NO: 3, SEQ ID NO 4 or SEQ ID NO 5, wherein the protease variant comprises or consists of the substitution L61K compared to the parent protease and wherein the protease variant has at least 60% identity to the polypeptide with SEQ ID NO: 3.

One aspect of the invention relates to a protease variant of a protease parent wherein parent protease is a polypeptide with SEQ ID NO: 3, SEQ ID NO 4 or SEQ ID NO 5, wherein the protease variant comprises or consists of the substitution V62G compared to the parent protease and wherein the protease variant has at least 60%, identity to the polypeptide with SEQ ID NO: 3.

One aspect of the invention relates to a protease variant of a protease parent wherein parent protease is a polypeptide with SEQ ID NO: 3, SEQ ID NO 4 or SEQ ID NO 5, wherein the protease variant comprises or consists of the substitution G64A compared to the parent protease and wherein the protease variant has at least 60% identity to the polypeptide with SEQ ID NO: 3.

One aspect of the invention relates to a protease variant of a protease parent wherein parent protease is a polypeptide with SEQ ID NO: 3, SEQ ID NO 4 or SEQ ID NO 5, wherein the protease variant comprises or consists of the substitution S65F compared to the parent protease and wherein the protease variant has at least 60% identity to the polypeptide with SEQ ID NO: 3.

One aspect of the invention relates to a protease variant of a protease parent wherein parent protease is a polypeptide with SEQ ID NO: 3, SEQ ID NO 4 or SEQ ID NO 5, wherein the protease variant comprises or consists of the substitution Q70T compared to the parent protease and wherein the protease variant has at least 60% identity to the polypeptide with SEQ ID NO: 3.

One aspect of the invention relates to a protease variant of a protease parent wherein parent protease is a polypeptide with SEQ ID NO: 3, SEQ ID NO 4 or SEQ ID NO 5, wherein the protease variant comprises or consists of the substitution Q70L compared to the parent protease and wherein the protease variant has at least 60% identity to the polypeptide with SEQ ID NO: 3.

One aspect of the invention relates to a protease variant of a protease parent wherein parent protease is a polypeptide with SEQ ID NO: 3, SEQ ID NO 4 or SEQ ID NO 5, wherein the protease variant comprises or consists of the substitution Q70Y compared to the parent protease and wherein the protease variant has at least 60% identity to the polypeptide with SEQ ID NO: 3.

One aspect of the invention relates to a protease variant of a protease parent wherein parent protease is a polypeptide with SEQ ID NO: 3, SEQ ID NO 4 or SEQ ID NO 5, wherein the protease variant comprises or consists of the substitution Q70F compared to the parent protease and wherein the protease variant has at least 60% identity to the polypeptide with SEQ ID NO: 3.

One aspect of the invention relates to a protease variant of a protease parent wherein parent protease is a polypeptide with SEQ ID NO: 3, SEQ ID NO 4 or SEQ ID NO 5, wherein the protease variant comprises or consists of the substitution Q70M compared to the parent protease and wherein the protease variant has at least 60% identity to the polypeptide with SEQ ID NO: 3.

One aspect of the invention relates to a protease variant of a protease parent wherein parent protease is a polypeptide with SEQ ID NO: 3, SEQ ID NO 4 or SEQ ID NO 5, wherein the protease variant comprises or consists of the substitution Q70A compared to the parent protease and wherein the protease variant has at least 60% identity to the polypeptide with SEQ ID NO: 3.

One aspect of the invention relates to a protease variant of a protease parent wherein parent protease is a polypeptide with SEQ ID NO: 3, SEQ ID NO 4 or SEQ ID NO 5, wherein the protease variant comprises or consists of the substitution Q70V compared to the parent protease and wherein the protease variant has at least 60% identity to the polypeptide with SEQ ID NO: 3.

One aspect of the invention relates to a protease variant of a protease parent wherein parent protease is a polypeptide with SEQ ID NO: 3, SEQ ID NO 4 or SEQ ID NO 5, wherein the protease variant comprises or consists of the substitution G107N compared to the parent protease and wherein the protease variant has at least 60% identity to the polypeptide with SEQ ID NO: 3.

One aspect of the invention relates to a protease variant of a protease parent wherein parent protease is a polypeptide with SEQ ID NO: 3, SEQ ID NO 4 or SEQ ID NO 5, wherein the protease variant comprises or consists of the insertion *108aA compared to the parent protease and wherein the protease variant has at least 60% identity to the polypeptide with SEQ ID NO: 3.

One aspect of the invention relates to a protease variant of a protease parent wherein parent protease is a polypeptide with SEQ ID NO: 3, SEQ ID NO 4 or SEQ ID NO 5, wherein the protease variant comprises or consists of the substitution N109T compared to the parent protease and wherein the protease variant has at least 60% identity to the polypeptide with SEQ ID NO: 3.

One aspect of the invention relates to a protease variant of a protease parent wherein parent protease is a polypeptide with SEQ ID NO: 3, SEQ ID NO 4 or SEQ ID NO 5, wherein the protease variant comprises or consists of the substitution S111I compared to the parent protease and wherein the protease variant has at least 60% identity to the polypeptide with SEQ ID NO: 3.

One aspect of the invention relates to a protease variant of a protease parent wherein parent protease is a polypeptide with SEQ ID NO: 3, SEQ ID NO 4 or SEQ ID NO 5, wherein the protease variant comprises or consists of the substitution Y113S compared to the parent protease and wherein the protease variant has at least 60% identity to the polypeptide with SEQ ID NO: 3.

One aspect of the invention relates to a protease variant of a protease parent wherein parent protease is a polypeptide with SEQ ID NO: 3, SEQ ID NO 4 or SEQ ID NO 5, wherein the protease variant comprises or consists of the substitution S114V compared to the parent protease and wherein the protease variant has at least 60% identity to the polypeptide with SEQ ID NO: 3.

One aspect of the invention relates to a protease variant of a protease parent wherein parent protease is a polypeptide with SEQ ID NO: 3, SEQ ID NO 4 or SEQ ID NO 5, wherein the protease variant comprises or consists of the substitution S114A compared to the parent protease and wherein the protease variant has at least 60% identity to the polypeptide with SEQ ID NO: 3.

One aspect of the invention relates to a protease variant of a protease parent wherein parent protease is a polypeptide with SEQ ID NO: 3, SEQ ID NO 4 or SEQ ID NO 5, wherein the protease variant comprises or consists of the substitution S114F compared to the parent protease and wherein the protease variant has at least 60% identity to the polypeptide with SEQ ID NO: 3.

One aspect of the invention relates to a protease variant of a protease parent wherein parent protease is a polypeptide with SEQ ID NO: 3, SEQ ID NO 4 or SEQ ID NO 5, wherein the protease variant comprises or consists of the substitution S133H compared to the parent protease and wherein the protease variant has at least 60% identity to the polypeptide with SEQ ID NO: 3.

One aspect of the invention relates to a protease variant of a protease parent wherein parent protease is a polypeptide with SEQ ID NO: 3, SEQ ID NO 4 or SEQ ID NO 5, wherein the protease variant comprises or consists of the substitution I137N compared to the parent protease and wherein the protease variant has at least 60% identity to the polypeptide with SEQ ID NO: 3.

One aspect of the invention relates to a protease variant of a protease parent wherein parent protease is a polypeptide with SEQ ID NO: 3, SEQ ID NO 4 or SEQ ID NO 5, wherein the protease variant comprises or consists of the substitution M139L compared to the parent protease and wherein the protease variant has at least 60% identity to the polypeptide with SEQ ID NO: 3.

One aspect of the invention relates to a protease variant of a protease parent wherein parent protease is a polypeptide with SEQ ID NO: 3, SEQ ID NO 4 or SEQ ID NO 5, wherein the protease variant comprises or consists of the substitution S143R compared to the parent protease and wherein the protease variant has at least 60% identity to the polypeptide with SEQ ID NO: 3.

One aspect of the invention relates to a protease variant of a protease parent wherein parent protease is a polypeptide with SEQ ID NO: 3, SEQ ID NO 4 or SEQ ID NO 5, wherein the protease variant comprises or consists of the substitution S144P compared to the parent protease and wherein the protease variant has at least 60% identity to the polypeptide with SEQ ID NO: 3.

One aspect of the invention relates to a protease variant of a protease parent wherein parent protease is a polypeptide with SEQ ID NO: 3, SEQ ID NO 4 or SEQ ID NO 5, wherein the protease variant comprises or consists of the substitution L149T compared to the parent protease and wherein the protease variant has at least 60% identity to the polypeptide with SEQ ID NO: 3.

One aspect of the invention relates to a protease variant of a protease parent wherein parent protease is a polypeptide with SEQ ID NO: 3, SEQ ID NO 4 or SEQ ID NO 5, wherein the protease variant comprises or consists of the substitution I150L compared to the parent protease and wherein the protease variant has at least 60% identity to the polypeptide with SEQ ID NO: 3.

One aspect of the invention relates to a protease variant of a protease parent wherein parent protease is a polypeptide with SEQ ID NO: 3, SEQ ID NO 4 or SEQ ID NO 5, wherein the protease variant comprises or consists of the substitution I150T compared to the parent protease and wherein the protease variant has at least 60% identity to the polypeptide with SEQ ID NO: 3.

One aspect of the invention relates to a protease variant of a protease parent wherein parent protease is a polypeptide with SEQ ID NO: 3, SEQ ID NO 4 or SEQ ID NO 5, wherein the protease variant comprises or consists of the substitution I150S compared to the parent protease and wherein the protease variant has at least 60% identity to the polypeptide with SEQ ID NO: 3.

One aspect of the invention relates to a protease variant of a protease parent wherein parent protease is a polypeptide with SEQ ID NO: 3, SEQ ID NO 4 or SEQ ID NO 5, wherein the protease variant comprises or consists of the substitution I150V compared to the parent protease and wherein the protease variant has at least 60% identity to the polypeptide with SEQ ID NO: 3.

One aspect of the invention relates to a protease variant of a protease parent wherein parent protease is a polypeptide with SEQ ID NO: 3, SEQ ID NO 4 or SEQ ID NO 5, wherein the protease variant comprises or consists of the substitution V162S compared to the parent protease and wherein the protease variant has at least 60% identity to the polypeptide with SEQ ID NO: 3.

One aspect of the invention relates to a protease variant of a protease parent wherein parent protease is a polypeptide with SEQ ID NO: 3, SEQ ID NO 4 or SEQ ID NO 5, wherein the protease variant comprises or consists of the substitution V162E compared to the parent protease and wherein the protease variant has at least 60% identity to the polypeptide with SEQ ID NO: 3.

One aspect of the invention relates to a protease variant of a protease parent wherein parent protease is a polypeptide with SEQ ID NO: 3, SEQ ID NO 4 or SEQ ID NO 5, wherein the protease variant comprises or consists of the substitution V162Q compared to the parent protease and wherein the protease variant has at least 60% identity to the polypeptide with SEQ ID NO: 3.

One aspect of the invention relates to a protease variant of a protease parent wherein parent protease is a polypeptide with SEQ ID NO: 3, SEQ ID NO 4 or SEQ ID NO 5, wherein the protease variant comprises or consists of the substitution V162G compared to the parent protease and wherein the protease variant has at least 60% identity to the polypeptide with SEQ ID NO: 3.

One aspect of the invention relates to a protease variant of a protease parent wherein parent protease is a polypeptide with SEQ ID NO: 3, SEQ ID NO 4 or SEQ ID NO 5, wherein the protease variant comprises or consists of the substitution V162F compared to the parent protease and wherein the protease variant has at least 60% identity to the polypeptide with SEQ ID NO: 3.

One aspect of the invention relates to a protease variant of a protease parent wherein parent protease is a polypeptide with SEQ ID NO: 3, SEQ ID NO 4 or SEQ ID NO 5, wherein the protease variant comprises or consists of the substitution V162T compared to the parent protease and wherein the protease variant has at least 60% identity to the polypeptide with SEQ ID NO: 3.

One aspect of the invention relates to a protease variant of a protease parent wherein parent protease is a polypeptide with SEQ ID NO: 3, SEQ ID NO 4 or SEQ ID NO 5, wherein the protease variant comprises or consists of the substitution V162Y compared to the parent protease and wherein the protease variant has at least 60% identity to the polypeptide with SEQ ID NO: 3.

One aspect of the invention relates to a protease variant of a protease parent wherein parent protease is a polypeptide with SEQ ID NO: 3, SEQ ID NO 4 or SEQ ID NO 5, wherein the protease variant comprises or consists of the substitution I164M compared to the parent protease and wherein the protease variant has at least 60% identity to the polypeptide with SEQ ID NO: 3.

One aspect of the invention relates to a protease variant of a protease parent wherein parent protease is a polypeptide with SEQ ID NO: 3, SEQ ID NO 4 or SEQ ID NO 5, wherein the protease variant comprises or consists of the substitution S171D compared to the parent protease and wherein the protease variant has at least 60% identity to the polypeptide with SEQ ID NO: 3.

One aspect of the invention relates to a protease variant of a protease parent wherein parent protease is a polypeptide with SEQ ID NO: 3, SEQ ID NO 4 or SEQ ID NO 5, wherein the protease variant comprises or consists of the substitution G182A compared to the parent protease and wherein the protease variant has at least 60% identity to the polypeptide with SEQ ID NO: 3.

One aspect of the invention relates to a protease variant of a protease parent wherein parent protease is a polypeptide with SEQ ID NO: 3, SEQ ID NO 4 or SEQ ID NO 5, wherein the protease variant comprises or consists of the substitution G182S compared to the parent protease and wherein the protease variant has at least 60% identity to the polypeptide with SEQ ID NO: 3.

One aspect of the invention relates to a protease variant of a protease parent wherein parent protease is a polypeptide with SEQ ID NO: 3, SEQ ID NO 4 or SEQ ID NO 5, wherein the protease variant comprises or consists of the substitution Q198E compared to the parent protease and wherein the protease variant has at least 60% identity to the polypeptide with SEQ ID NO: 3.

One aspect of the invention relates to a protease variant of a protease parent wherein parent protease is a polypeptide with SEQ ID NO: 3, SEQ ID NO 4 or SEQ ID NO 5, wherein the protease variant comprises or consists of the substitution Q198D compared to the parent protease and wherein the protease variant has at least 60% identity to the polypeptide with SEQ ID NO: 3.

One aspect of the invention relates to a protease variant of a protease parent wherein parent protease is a polypeptide with SEQ ID NO: 3, SEQ ID NO 4 or SEQ ID NO 5, wherein the protease variant comprises or consists of the substitution G200C compared to the parent protease and wherein the protease variant has at least 60% identity to the polypeptide with SEQ ID NO: 3.

One aspect of the invention relates to a protease variant of a protease parent wherein parent protease is a polypeptide with SEQ ID NO: 3, SEQ ID NO 4 or SEQ ID NO 5, wherein the protease variant comprises or consists of the substitution G200S compared to the parent protease and wherein the protease variant has at least 60% identity to the polypeptide with SEQ ID NO: 3

One aspect of the invention relates to a protease variant of a protease parent wherein parent protease is a polypeptide with SEQ ID NO: 3, SEQ ID NO 4 or SEQ ID NO 5, wherein the protease variant comprises or consists of the substitution A233S compared to the parent protease and wherein the protease variant has at least 60% identity to the polypeptide with SEQ ID NO: 3

One aspect of the invention relates to a protease variant of a protease parent wherein parent protease is a polypeptide with SEQ ID NO: 3, SEQ ID NO 4 or SEQ ID NO 5, wherein the protease variant comprises or consists of the substitution T246M compared to the parent protease and wherein the protease variant has at least 60% identity to the polypeptide with SEQ ID NO: 3

One aspect of the invention relates to a protease variant of a protease parent wherein parent protease is a polypeptide with SEQ ID NO: 3, SEQ ID NO 4 or SEQ ID NO 5, wherein the protease variant comprises or consists of the substitution A267S compared to the parent protease and wherein the protease variant has at least 60% identity to the polypeptide with SEQ ID NO: 3

One aspect of the invention relates to a protease variant of a protease parent wherein parent protease is a polypeptide with SEQ ID NO: 3, SEQ ID NO 4 or SEQ ID NO 5, wherein the protease variant comprises or consists of the substitution S274V compared to the parent protease and wherein the protease variant has at least 60% identity to the polypeptide with SEQ ID NO: 3

One aspect of the invention relates to a protease variant of a protease parent wherein parent protease is a polypeptide with SEQ ID NO: 3, SEQ ID NO 4 or SEQ ID NO 5, wherein the protease variant comprises or consists of the substitution Q275Y compared to the parent protease and wherein the protease variant has at least 60% identity to the polypeptide with SEQ ID NO: 3

One aspect of the invention relates to a protease variant of a protease parent wherein parent protease is a polypeptide with SEQ ID NO: 3, SEQ ID NO 4 or SEQ ID NO 5, wherein the protease variant comprises or consists of the substitution L276I compared to the parent protease and wherein the protease variant has at least 60% identity to the polypeptide with SEQ ID NO: 3

The present invention also relates to cleaning compositions such as detergent compositions comprising a protease variant of the invention. In one embodiment the cleaning composition is a liquid or powder laundry detergent, suitable for e.g. washing at high temperature and/or pH, such as at or above 40° C. and/or at or above pH 8. In one embodiment the cleaning composition is a liquid or powder laundry detergent, suitable for e.g. washing at low temperature and/or pH, such as at or below 20° C. and/or pH 6. The detergent may also be formulated as a unit dose detergent and/or compact detergent optionally with minimum or no water. The detergent may also be a dish wash detergent which is preferably phosphate-free. The cleaning composition may further comprise at least one additional enzyme, such as carbohydrate-active enzymes like carbohydrase, pectinase, mannanase, amylase, cellulase, arabinase, galactanase, xylanase, or proteases such as metalloproteases, lipase, a, cutinase, oxidase, e.g., a laccase, and/or peroxidase.

In general positions within a protease useful for making variants are those positions wherein at least one substitution leads to a variant exhibiting an improved characteristic as compared to the unchanged protease The variants may further comprise one or more additional alterations at one or more (e.g., several) other positions. In a particular preferred embodiment the protease variants of the invention, further comprises a substitution at one or more positions corresponding to positions 171, 173, 175, 179 and 180 of SEQ ID NO: 3, wherein the variant has a sequence identity to SEQ ID NO: 3 of at least 60%, and the variant has protease activity. In an even more preferred embodiment the amino acid at the position corresponding to position 171 of SEQ ID NO: 3 is selected from the group consisting of Trp, Lys, Glu, Asn and/or the amino acid at the position corresponding to position 173 of SEQ ID NO: 3 is Pro, and/or the amino acid at the position corresponding to position 175 of SEQ ID NO: 3 is Ala, Val, Pro, and/or the amino acid at the position corresponding to position 179 of SEQ ID NO: 3 is selected from the group consisting of Cys, Val, Gln, Ser, Thr, Glu, His, Lys, Met, Asn, Tyr and Ala and/or the amino acid at the position corresponding to position 180 of SEQ ID NO 3 is Tyr. In another preferred embodiment the protease variants of the invention, further comprises a substitution at two or more positions corresponding to positions 171, 173, 175, 179 or 180 of SEQ ID NO: 3, wherein the variant has a sequence identity to SEQ ID NO: 3 of at least 60% and less than 100%, and the variant has protease activity at two positions corresponding to any of positions 171, 173, 175, 179, and 180. In a preferred embodiment of the invention the variants of the invention comprises the mutations S173P+S175P as shown in SEQ ID NO 4. In another preferred embodiment the protease variants of the invention comprises the mutations S173P+S175P+F180Y as shown in SEQ ID NO 5.

In a particular embodiment of the invention, the protease variants of the invention comprises the following alterations compared to SEQ ID NO 3: A1L, S173P, S175P, F180Y;
  A1*, S27K, S173P, S175P, F180Y, Q198E, T297P;
  V2I, S173P, S175P, F180Y;
  A1*, P3*, Q6C, S27K, S171N, S173P, G174R, S175P, F180Y, Q198E, T297P;
  A1*, P3*, S4C, S27K, S171N, S173P, G174R, S175P, F180Y, Q198E, T297P;
  A1*, P3*, S4C, S27K, S171N, S173P, G174R, S175P, F180Y, Q198E, E236C, T297P;
  A1*, V2*, P3*, S4*, S27K, S173P, S175P, F180Y, Q198E, T297P;
  S4C, S27K, S171N, S173P, G174R, S175P, F180Y, Q198E, E236C, T297P;
  Q6C, S27K, S171N, S173P, G174R, S175P, F180Y, Q198E, E236C, T297P;
  Q18A, S173P, S175P, F180Y;
  L431, G47K, R130K, G132R, S173P, S175P;
  S27K, N59L, T67V, Q70N, S171N, S173P, G174R, S175P, F180Y, Q198E, N199K, T297P;
  L61K, S173P, S175P;
  V62G, R69D, S173P, S175P;
  G64A, R69D, S173P, S175P;
  G64S, R69D, S173P, S175P;
  S65F, S173P, S175P, F180Y;
  Q70T, L149T, I150L, S173P, S175P;
  Q70T, I121L, S173P, S175P;
  Q70L, S173P, S175P, F180Y;
  Q70Y, S173P, S175P, F180Y;
  S27K, Q70Y, E127Q, S173P, S175P, F180Y, Q198E, T297P;
  Q70F, S173P, S175P, F180Y;
  S27K, Q70F, E127Q, S173P, S175P, F180Y, Q198E, T297P;
  S27K, Q70F, G 107N, I121V, E127Q, S173P, S175P, F180Y, Q198E, T297P;
  Q70M, S173P, S175P, F180Y;
  Q70A, S173P, S175P, F180Y;
  S27K, Q70A, S171N, S173P, G174R, S175P, F180Y, Q198E, N199K, T297P;
  S27K, Q70A, S114V, E127Q, I150L, S173P, S175P, F180Y, Q198E, T297P;
  S27K, Q70A, G107N, I121V, E127Q, S173P, S175P, F180Y, Q198E, T297P;
  S27K, Q70A, I121V, S171N, S173P, G174R, S175P, F180Y, Q198E, T297P;
  S27K, Q70A, G107N, I121V, E127O, S173P, S175P, F180Y, Q198E, T297P;
  S27K, Q70A, S114V, S173P, G174K, S175P, F180Y, Q198E, N199K, T297P;
  S27K, Q70V, S171N, S173P, G174R, S175P, F180Y, Q198E, N199K, T297P;
  S27K, Q70V, S114V, E127Q, I150L, S173P, S175P, F180Y, Q198E, T297P;
  S27K, Q70V, G107N, I121V, E127Q, S173P, S175P, F180Y, Q198E, T297P;
  S27K, Q70V, S171N, S173P, G174R, S175P, F180Y, Q198E, T297P;
  G107N, S173P, S175P, F180Y, Q198E, T297P;
  Q70N, G107N, I137Q, S173P, S175P, F180Y, T297P;
  Q70N, G107N, I137N, S173P, S175P, F180Y, T297P;
  S27K, G107N, E127Q, S173P, S175P, F180Y, Q198E, T297P;
  S27K, N59L, T67V, N87K, G107N, I121V, S171N, S173P, G174R, S175P, F180Y, Q198E, T297P;
  S27K, Y39R, G107N, I137E, S173P, S175P, F180Y, T297P;
  S27K, Q70N, N87K, G107N, I121V, E127Q, S171N, S173P, G174R, S175P, F180Y, Q198E, T297P;
  S27K, *108aA, N109S, S111R, S173P, S175P, F180Y, Q198E, T297P;
  S27K, N109T, S173P, S175P, F180Y, Q198E, T297P;
  S27K, N109S, *109aA, S111R, S173P, S175P, F180Y, Q198E, T297P;
  S27K, N109A, S173P, S175P, F180Y, Q198E, T297P;
  S27K, N109A, S173P, G174K, S175P, F180Y, Q197K, Q198E, T297P;
  S111I, S173P, S175P, F180Y;
  Q70N, Y113S, S173P, S175P;
  Y113S, A145S, S173P, S175P;
  S114V, A145S, S173P, S175P;

S114V, K146P, S173P, S175P;
S114V, M139L, S173P, S175P;
S27K, S114V, E127Q, I150L, S173P, S175P, F180Y, Q198E, T297P;
S27K, S114V, S171N, S173P, G174R, S175P, F180Y, Q198E, N199K, T297P;
S27K, S114V, S171N, S173P, G174R, S175P, F180Y, Q198E, N199R, T297P;
S27K, S114V, I150L, S171N, S173P, G174R, S175P, F180Y, Q198E, N199K, T297P;
S27K, Q70A, S114V, S173P, G174K, S175P, F180Y, Q198E, N199K, T297P;
S114A, S173P, S175P, F180Y;
S27K, Q70N, S114A, S171N, S173P, G174R, S175P, F180Y, Q198E, N199K, T297P;
S114F, S173P, S175P, F180Y;
S27K, S114F, E127Q, S173P, S175P, F180Y, Q198E, T297P;
S27K, S133H, S173P, S175P, F180Y, T297P;
I137N, S173P, S175P, F180Y, Q198E, T297P;
S27K, Q97K, I137N, S173P, S175P, F180Y, Q198E, T297P;
S27K, Q97K, I137N, S173P, S175P, F180Y, T297P;
S27K, I137N, S173P, S175P, F180Y, S270K, T297P;
S27K, S111R, I137N, S173P, S175P, F180Y, T297P;
S27K, E127Q, I137N, S173P, S175P, F180Y, Q198E, T297P;
Q70N, G107N, I137N, S173P, S175P, F180Y, T297P;
S27K, I137N, S171N, S173P, G174R, S175P, F180Y, Q198E, T297P;
S27K, N109S, S111R, I137N, S173P, S175P, F180Y, Q198E, T297P;
S114V, M139L, S173P, S175P;
S27K, S143R, S173P, S175P, F180Y, T297P;
S144P, S173P, S175P;
S144P, A145S, K146P, S148A, L149T, I150L, S173P, S175P I137E, S144P, S173P, S175P, F180Y, T297P S27K, S144P, D147N, S173P, S175P, F180Y, Q198E, T297P;
Q70N, I137Q, S144P, S173P, S175P, F180Y, T297P;
Q70N, I137N, S144P, S173P, S175P, F180Y, T297P;
S27K, E127Q, S144P, S173P, S175P, F180Y, Q198E, T297P;
S27K, Q70N, E127Q, S144P, S173P, S175P, F180Y, Q198E, T297P;
S27K, S144P, S171N, S173P, G174R, S175P, F180Y, Q198E, N199K, T297P;
S27K, S144P, K146T, A151R, S171N, S173P, G174R, S175P, F180Y, Q198E, N199K, T297P;
S27K, S144P, K146P, A151R, S171N, S173P, G174R, S175P, F180Y, Q198E, N199K, T297P;
S27K, S144P, K146T, I150L, A151R, S171N, S173P, G174R, S175P, F180Y, Q198E, N199K, T297P;
S27K, S144P, K146P, I150L, A151R, S171N, S173P, G174R, S175P, F180Y, Q198E, N199K, T297P;
A145S, K146P, D147S, S148A, L149T, S173P, S175P;
1137A, L149T, I150L, S173P, S175P;
K146P, L149T, S173P, S175P;
D116S, L149T, S173P, S175P;
S27K, S114V, E127Q, I150L, S173P, S175P, F180Y, Q198E, T297P;
S27K, Q70N, E127Q, I150L, S173P, S175P, F180Y, Q198E, T297P;
S27K, I150L, S171N, S173P, G174R, S175P, F180Y, Q198E, N199K, T297P;
S27K, I150L, S171N, S173P, G174R, S175P, F180Y, Q198E, N199R, T297P;
S27K, K146T, I150L, A151R, S171N, S173P, G174R, S175P, F180Y, Q198E, N199K, T297P;
S27K, K146P, I150L, A151R, S171N, S173P, G174R, S175P, F180Y, Q198E, N199K, T297P;
S27K, S144R, K146T, I150L, A151R, S171N, S173P, G174R, S175P, F180Y, Q198E, N199K, T297P;
I150T, S173P, S175P, F180Y;
N16H, S27K, E50H, G132H, I150S, S173P, S175P, F180Y, Q198E, T297P;
S27K, I150S, S171N, S173P, G174R, S175P, F180Y, Q198E, N199K, T297P;
S27K, I150S, S171N, S173P, G174R, S175P, F180Y, Q198E, N199R, T297P;
S27K, K146T, I150S, A151R, S171N, S173P, G174R, S175P, F180Y, Q198E, N199K, T297P;
S27K, K146P, I150S, A151R, S171N, S173P, G174R, S175P, F180Y, Q198E, N199K, T297P;
S27K, Q70N, I121V, I150S, S171N, S173P, G174R, S175P, F180Y, Q198E, T297P;
I150V, S173P, S175P, F180Y;
S27K, V162S, S173P, S175P, F180Y, Q198E, T297P;
S27K, E127Q, V162S, S173P, S175P, F180Y, Q198E, T297P;
N16H, S27K, E50H, G132H, V162S, S173P, S175P, F180Y, Q198E, T297P;
S27K, V162E, S173P, S175P, F180Y, Q198E, T297P;
S27K, E127Q, V162E, S173P, S175P, F180Y, Q198E, T297P;
S27K, V162Q, S173P, S175P, F180Y, Q198E, T297P;
S27K, E127Q, V162Q, S173P, S175P, F180Y, Q198E, T297P;
S27K, V162G, S173P, S175P, F180Y, Q198E, T297P;
S27K, E127Q, V162G, S173P, S175P, F180Y, Q198E, T297P;
S27K, V162F, S173P, S175P, F180Y, Q198E, T297P;
S27K, E127Q, V162F, S173P, S175P, F180Y, Q198E, T297P;
S27K, I121V, V162F, S171N, S173P, G174R, S175P, F180Y, Q198E, T297P;
S27K, V162F, S173P, G174K, S175P, F180Y, Q197K, Q198E, T297P;
S27K, V162T, S173P, S175P, F180Y, Q198E, T297P;
S27K, E127Q, V162T, S173P, S175P, F180Y, Q198E, T297P;
S27K, V162T, S173P, G174K, S175P, F180Y, Q198E, N199R, T297P;
S27K, V162Y, S173P, S175P, F180Y, Q198E, T297P;
S27K, E127Q, V162Y, S173P, S175P, F180Y, Q198E, T297P;
S27K, Q70N, G107N, I121V, E127Q, V162Y, S173P, S175P, F180Y, Q198E, T297P;
S27K, V162Y, S173P, G174K, S175P, F180Y, Q198E, N199K, T297P;
S27K, V162Y, S173P, G174K, S175P, F180Y, Q197K, Q198E, T297P;
S27K, V162Y, S171N, S173P, G174R, S175P, F180Y, G182A, L184Y, Q198E, N199K, T297P;
S27K, Q70N, G107N, I121V, E127Q, V162Y, S171N, S173P, G174R, S175P, F180Y, Q198E, T297P;
1164M, S173P, S175P, F180Y;
S27K, S171D, S173P, G174R, S175P, F180Y, Q198E, T297P;
S173P, S175P, F180Y, G182A;
S27K, K146E, S171N, S173P, G174R, S175P, F180Y, G182A, Q198E, N199K, E223K, T297P;
S27K, S114V, I150L, S171N, S173P, G174R, S175P, F180Y, G182A, Q198E, N199K, T297P;

S27K, S173P, G174K, S175P, G179S, F180Y, G182A, Q198E, N199K, T297P;
S27K, S173P, G174K, S175P, F180Y, G182A, L184F, V185P, Q198E, N199K, T297P;
S27K, S173P, G174K, S175P, F180Y, G182A, L184Y, V185P, Q198E, N199K, T297P;
S27K, Q70N, G107N, I121V, E127Q, S173P, S175P, F180Y, G182A, Q198E, T297P;
S27K, S173P, G174K, S175P, F180Y, G182A, Q198E, N199K, T297P;
S27K, S173P, G174K, S175P, F180Y, G182A, Q198E, N199K, T297P;
S27K, S173P, G174K, S175P, F180Y, G182A, Q197K, Q198E, T297P;
S27K, S173P, G174K, S175P, F180Y, G182A, Q198E, N199R, T297P;
I121V, S173P, S175P, F180Y, G182A, T297P;
I121V, S173P, S175P, F180Y, G182A, S274V, T297P;
S173P, S175P, F180Y, G182S;
S173P, S175P, Q198E;
S173P, S175P, Q198E;
I137E, S173P, S175P, F180Y, Q198E, T297P;
V162R, S173P, S175P, F180Y, Q198E, T297P;
D155N, S173P, S175P, Q198E;
D17N, S173P, S175P, Q198E;
D147N, S173P, S175P, Q198E;
Y156R, S173P, S175P, Q198E;
S27K, S173P, S175P, Q198E;
D147Q, S173P, S175P, Q198E;
Q97K, S173P, S175P, Q198E;
E50Q, S173P, S175P, Q198E;
S173P, S175P, F180Y, Q198E, V286Q, T297P;
G107N, S173P, S175P, F180Y, Q198E, T297P;
Y156R, S173P, S175P, F180Y, Q198E, T297P;
S27K, S173P, S175P, F180Y, Q198E, T297P;
N87K, S173P, S175P, F180Y, Q198E, T297P;
D147Q, S173P, S175P, F180Y, Q198E, T297P;
I137N, S173P, S175P, F180Y, Q198E, T297P;
I121V, S173P, S175P, F180Y, Q198E, T297P;
S27K, S173P, S175P, F180Y, Q198E, I293R, T297P;
S27K, S173P, S175P, F180Y, Q198E, S270K, T297P;
S27K, S173P, G174R, S175P, F180Y, Q198E, T297P;
S27K, D126G, S173P, S175P, F180Y, Q198E, T297P;
S27K, Q97K, S173P, S175P, F180Y, Q198E, T297P;
S27K, Q97K, I137N, S173P, S175P, F180Y, Q198E, T297P;
S27K, S173P, S175P, F180Y, Q197K, Q198E, T297P;
S27K, E127Q, I137E, S173P, S175P, F180Y, Q198E, T297P;
S27K, N59L, T67V, N87K, I121V, S171N, S173P, G174R, S175P, F180Y, Q198E, T297P;
S27K, S173P, S175P, F180Y, Q198D, T297P;
S173P, S175P, F180Y, E194I, V196I, Q197R, Q198E, N199I, G200C, T297P;
S173P, S175P, F180Y, E194I, V196I, Q197R, Q198E, N199I, G200S, T297P;
S27K, S171N, S173P, G174R, S175P, F180Y, Q198E, N199K, A233S, T297P;
S173P, S175P, T246M, I247K;
Y113T, E127Q, S173P, G174K, S175P, F180Y, A267S;
S27K, S173P, S175P, F180Y, Q198E, S274V, T297P;
S27K, S173P, G174K, S175P, F180Y, Q198E, N199R, S274V, T297P;
I121V, S173P, S175P, F180Y, S274V, T297P;
I121V, S173P, S175P, F180Y, G182A, S274V, T297P;
I121V, S173P, S175P, F180Y, Q198E, N199R, S274V, T297P;
S27K, Q70N, I121V, S171N, S173P, G174R, S175P, F180Y, Q198E, S274V, T297P;
S27K, Q70A, S114V, E127Q, I150L, S173P, S175P, F180Y, Q198E, S274V, T297P;
S173P, S175P, F180Y, Q275Y;
S173P, S175P, F180Y, L276I;
S27K, N59L, T67V, I121V, S173P, G174K, S175P, F180Y, G182A, L184Y, Q197K, Q198E, T297P;
S27K, I121V, S173P, G174R, S175A, F180Y, G182A, L184Y, Q197K, Q198E, S270V, T297P;
S27K, Q70A, I121V, E127Q, S173P, G174K, S175P, F180Y, G182A, L184F, Q197K, Q198E, T297P;
S27K, Q70A, S171D, S173P, G174R, S175P, F180Y, G182A, L184F, Q198E, N199K, S274V, T297P;
S27K, Q70N, I121V, S173P, G174K, S175P, G182A, L184F, Q198E, T297P;
S27K, S171E, S173P, G174K, S175P, F180Y, G182A, L184F, Q198E, N199K, T297P;
S27K, S173P, G174K, S175P, F180Y, G182A, L184F, Q198E, V286R, T297P;
S27K, V162T, S171D, S173P, G174R, S175A, F180Y, G182A, L184F, Q197K, Q198E, T297P;
S27K, S171D, S173P, G174R, S175A, F180Y, G182A, L184F, Q198E, N199K, T297P;
S27K, N87K, S171D, S173P, G174R, S175P, G182A, L184F, Q198E, N199R, T297P;
S27K, N109R, S111E, S171E, S173P, G174K, S175P, F180Y, G182A, L184F, Q198E, N199K, T297P;
527K, N109K, S111E, S171E, S173P, G174K, S175P, F180Y, G182A, L184F, Q198E, N199K, T297P;
S27K, *108aA, N109S, V162T, S173P, G174K, S175A, F180Y, G182A, L184F, Q197K, Q198E, T297P;
S27K, N109R, S111E, V162T, S173P, G174K, S175A, F180Y, G182A, L184F, Q197K, Q198E, T297P;
S27K, *108aA, N109S, S171D, S173P, G174R, S175A, F180Y, G182A, L184F, Q198E, N199K, T297P;
E50Q;
Q70N;
Q97K;
S111R;
S114A;
D126K;
D126G;
E127Q;
E127R;
S144P;
S144R;
A145E;
L149R;
G182A and
S274V The variants may further comprise one or more additional alterations at one or more (e.g., several) other positions. The amino acid changes may be of a minor nature, that is conservative amino acid substitutions or insertions that do not significantly affect the folding and/or activity of the protein; small deletions, typically of 1-5 amino acids; small amino- or carboxyl-terminal extensions, such as an amino-terminal methionine residue; a small linker peptide of up to 20-25 residues, located at the amino- or carboxyl terminal; or a small extension that facilitates purification by changing net charge or another function, such as a poly-histidine tract, an antigenic epitope or a binding domain.

Examples of conservative substitutions are within the groups of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, In, The Proteins, Academic Press, New York. Common substitutions are Ala/Ser, Val/Ile, Asp/Glu, Asn/Gln, Thr/Ser, Ala/Gly, Ala/Thr, Ser/Asn, AlaNal, Ser/Gly, Tyr/Phe, Ala/Pro, Lys/Arg, Asp/Asn, Glu/Gln, Leu/Ile, LeuNal, Ala/Glu, and Asp/Gly.

Alternatively, the amino acid changes are of such a nature that the physico-chemical properties of the polypeptides are altered. For example, amino acid changes may improve the thermal stability of the polypeptide, alter the substrate specificity, change the pH optimum, and the like.

Essential amino acids in a polypeptide can be identified according to procedures known in the art, such as site-directed mutagenesis or alanine-scanning mutagenesis (Cunningham and Wells, 1989, Science 244: 1081-1085). In the latter technique, single alanine mutations are introduced at every residue in the molecule, and the resultant variant molecules are tested for protease activity to identify amino acid residues that are critical to the activity of the molecule. See also, Hilton et al., 1996, J. Biol. Chem. 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, Science 255: 306-312; Smith et al., 1992, J. Mol. Biol. 224: 899-904; Wlodaver et al., 1992, FEBS Lett. 309: 59-64. The identity of essential amino acids can also be inferred from an alignment with a related polypeptide. For the TY-145 protease (SEQ ID NO: 3) the catalytic triad comprising the amino acids D35, H72 and S251 is essential for protease activity of the enzyme.

In an embodiment, the variant has improved catalytic activity compared to the parent enzyme.

The homology between two amino acid sequences is in this context described by the parameter "identity" for purposes of the present invention, the degree of identity between two amino acid sequences is determined using the Needleman-Wunsch algorithm as described above. The output from the routine is besides the amino acid alignment the calculation of the "Percent Identity" between the two sequences.

Based on this description it is routine for a person skilled in the art to identify suitable homologous proteases, which can be modified according to the invention.

Substantially homologous parent protease variants may have one or more (several) amino acid substitutions, deletions and/or insertions, in the present context the term "one or more" is used interchangeably with the term "several". These changes are preferably of a minor nature, that is conservative amino acid substitutions as described above and other substitutions that do not significantly affect the three-dimensional folding or activity of the protein or polypeptide; small deletions, typically of one to about 30 amino acids; and small amino- or carboxyl-terminal extensions, such as an amino-terminal methionine residue, a small linker peptide of up to about 20-25 residues, or a small extension that facilitates purification (an affinity tag), such as a poly-histidine tract, or protein A (Nilsson et al., 1985, EMBO J. 4: 1075; Nilsson et al., 1991, Methods Enzymol. 198: 3. See, also, in general, Ford et al., 1991, Protein Expression and Purification 2: 95-107.

Although the changes described above preferably are of a minor nature, such changes may also be of a substantive nature such as fusion of larger polypeptides of up to 300 amino acids or more both as amino- or carboxyl-terminal extensions.

The parent protease may comprise or consist of the amino acid sequence of SEQ ID NO: 3 or an allelic variant thereof; or a fragment thereof having protease activity. In one aspect, the parent protease comprises or consists of the amino acid sequence of SEQ ID NO: 3.

The parent protease may be (a) a polypeptide having at least 60% sequence identity to polypeptide of SEQ ID NO: 3; (b) a polypeptide encoded by a polynucleotide that hybridizes under medium or high stringency conditions with (i) the mature polypeptide coding sequence of SEQ ID NO: 1, (ii) a sequence encoding the mature polypeptide of SEQ ID NO: 2, or (iii) the full-length complement of (i) or (ii); or (c) a polypeptide encoded by a polynucleotide having at least 60% sequence identity to the mature polypeptide coding sequence of SEQ ID NO: 1.

In an aspect, the parent protease has a sequence identity to the polypeptide with SEQ ID NO: 3 of at least 60%, at least 61%, at least 62%, at least 63%, at least 64%,at least 65%, at least 66%, at least 67%, at least 68%, at least 69%, at least 70%, at least 71%, at least 72%, at least 73%, at least 74%,at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99%.

In one aspect, the amino acid sequence of the parent protease differs by no more than 10 amino acids, e.g., 1, 2, 3, 4, 5, 6, 7, 8, or 9, from the polypeptide with SEQ ID NO: 3.

In another aspect, the parent comprises or consists of the amino acid sequence of SEQ ID NO: 3. In another aspect, the parent comprises or consists of amino acids 1 to 311 of SEQ ID NO: 2.

In one aspect, the amino acid sequence of the parent protease differs by no more than 10 amino acids, e.g., 1, 2, 3, 4, 5, 6, 7, 8, or 9, from the polypeptide with SEQ ID NO: 4.

In another aspect, the parent comprises or consists of the amino acid sequence of SEQ ID NO: 4.

In one aspect, the amino acid sequence of the parent protease differs by no more than 10 amino acids, e.g., 1, 2, 3, 4, 5, 6, 7, 8, or 9, from the polypeptide with SEQ ID NO: 5.

In another aspect, the parent comprises or consists of the amino acid sequence of SEQ ID NO: 5.

In another aspect, the parent protease is encoded by a polynucleotide that hybridizes under very low stringency conditions, low stringency conditions, medium stringency conditions, or high stringency conditions, or very high stringency conditions with (i) the mature polypeptide coding sequence of SEQ ID NO: 1, (ii) a sequence encoding the mature polypeptide of SEQ ID NO: 2, or (iii) the full-length complement of (i) or (ii), (Sambrook et al., 1989, Molecular Cloning, A Laboratory Manual, 2d edition, Cold Spring Harbor, N.Y.).

The polynucleotide of SEQ ID NO: 1 or a subsequence thereof, as well as the polypeptide of SEQ ID NO: 3 or a fragment thereof may be used to design nucleic acid probes to identify and clone DNA encoding a parent from strains of different genera or species according to methods well known in the art. In particular, such probes can be used for hybridization with the genomic DNA or cDNA of a cell of interest, following standard Southern blotting procedures, in order to identify and isolate the corresponding gene therein. Such probes can be considerably shorter than the entire sequence, but should be at least 15, e.g., at least 25, at least 35, or at least 70 nucleotides in length. Preferably, the nucleic acid probe is at least 100 nucleotides in length, e.g., at least 200 nucleotides, at least 300 nucleotides, at least 400 nucleotides, at least 500 nucleotides, at least 600 nucleotides, at least 700 nucleotides, at least 800 nucleotides, or at least 900 nucleotides in length. Both DNA and RNA probes can be used. The probes are typically labeled for detecting the corresponding gene (for example, with $^{32}P$, $^{3}H$, $^{35}S$, biotin, or avidin). Such probes are encompassed by the present invention.

A genomic DNA or cDNA library prepared from such other strains may be screened for DNA that hybridizes with the probes described above and encodes a parent. Genomic or other DNA from such other strains may be separated by agarose or polyacrylamide gel electrophoresis, or other separation techniques. DNA from the libraries or the separated DNA may be transferred to and immobilized on nitrocellulose or other suitable carrier material. In order to identify a clone or DNA that hybridizes with SEQ ID NO: 1 or a subsequence thereof, the carrier material is used in a Southern blot.

For purposes of the present invention, hybridization indicates that the polynucleotide hybridizes to a labeled nucleic acid probe corresponding to (i) SEQ ID NO: 1; (ii) the mature polypeptide coding sequence of SEQ ID NO: 1; (iii) a sequence encoding the mature polypeptide of SEQ ID NO: 2; (iv) the full-length complement thereof; or (v) a subsequence thereof; under very low to very high stringency conditions. Molecules to which the nucleic acid probe hybridizes under these conditions can be detected using, for example, X-ray film or any other detection means known in the art.

In one aspect, the nucleic acid probe is the mature polypeptide coding sequence of SEQ ID NO: 1. In another aspect, the nucleotide acid probe is a 80 to 1140 nucleotides long fragment of SEQ ID NO: 1, e.g. 90, 100, 200, 300, 400, 500, 600, 700, 800, 900, 1000 or 1100 nucleotides long. In another aspect, the nucleic acid probe is a polynucleotide that encodes the polypeptide of SEQ ID NO: 2; the mature polypeptide thereof; or a fragment thereof. In another aspect, the nucleic acid probe is SEQ ID NO: 1.

In another embodiment, the parent is encoded by a polynucleotide having a sequence identity of at least 60%, such as at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% to the mature polypeptide coding sequence of SEQ ID NO: 1 or a sequence encoding the mature polypeptide of SEQ ID NO: 2.

The polypeptide may be a hybrid polypeptide in which a region of one polypeptide is fused at the N-terminus or the C-terminus of a region of another polypeptide.

The parent may be a fusion polypeptide or cleavable fusion polypeptide in which another polypeptide is fused at the N-terminus or the C-terminus of the polypeptide of the present invention. A fusion polypeptide is produced by fusing a polynucleotide encoding another polypeptide to a polynucleotide of the present invention. Techniques for producing fusion polypeptides are known in the art, and include ligating the coding sequences encoding the polypeptides so that they are in frame and that expression of the fusion polypeptide is under control of the same promoter(s) and terminator. Fusion polypeptides may also be constructed using intein technology in which fusion polypeptides are created post-translationally (Cooper et al., 1993, *EMBO J.* 12: 2575-2583; Dawson et al., 1994, *Science* 266: 776-779).

A fusion polypeptide can further comprise a cleavage site between the two polypeptides. Upon secretion of the fusion protein, the site is cleaved releasing the two polypeptides. Examples of cleavage sites include, but are not limited to, the sites disclosed in Martin et al., 2003, *J. Ind. Microbiol. Biotechnol.* 3: 568-576; Svetina et al., 2000, *J. Biotechnol.* 76: 245-251; Rasmussen-Wilson et al., 1997, *Appl. Environ. Microbiol.* 63: 3488-3493; Ward et al., 1995, *Biotechnology* 13: 498-503; and Contreras et al., 1991, *Biotechnology* 9: 378-381; Eaton et al., 1986, *Biochemistry* 25: 505-512; Collins-Racie et al., 1995, *Biotechnology* 13: 982-987; Carter et al., 1989, *Proteins: Structure, Function, and Genetics* 6: 240-248; and Stevens, 2003, *Drug Discovery World* 4: 35-48.

The parent may be obtained from organisms of any genus. For purposes of the present invention, the term "obtained from" as used herein in connection with a given source shall mean that the parent encoded by a polynucleotide is produced by the source or by a strain in which the polynucleotide from the source has been inserted. In one aspect, the parent is secreted extracellularly.

The parent may be a bacterial protease. For example, the parent may be a Gram-positive bacterial polypeptide such as a *Bacillus*, *Clostridium*, *Enterococcus*, *Geobacillus*, *Lactobacillus*, *Lactococcus*, *Oceanobacillus*, *Staphylococcus*, *Streptococcus*, or *Streptomyces* protease, or a Gram-negative bacterial polypeptide such as a *Campylobacter*, *E. coli*, *Flavobacterium*, *Fusobacterium*, *Helicobacter*, *Ilyobacter*, *Neisseria*, *Pseudomonas*, *Salmonella*, or *Ureaplasma* protease.

In one aspect, the parent is a *Bacillus alkalophilus*, *Bacillus amyloliquefaciens*, *Bacillus brevis*, *Bacillus circulans*, *Bacillus clausii*, *Bacillus coagulans*, *Bacillus firmus*, *Bacillus lautus*, *Bacillus lentus*, *Bacillus licheniformis*, *Bacillus megaterium*, *Bacillus pumilus*, *Bacillus stearothermophilus*, *Bacillus subtilis*, or *Bacillus thuringiensis* protease In one aspect, the parent is a *Bacillus* sp. protease, e.g., the protease with SEQ ID NO: 3 or the mature polypeptide of SEQ ID NO 2.

Strains of these species are readily accessible to the public in a number of culture collections, such as the American Type Culture Collection (ATCC), Deutsche Sammlung von Mikroorganismen and Zellkulturen GmbH (DSMZ), Centraalbureau Voor Schimmelcultures (CBS), and Agricultural Research Service Patent Culture Collection, Northern Regional Research Center (NRRL).

The parent may be identified and obtained from other sources including microorganisms isolated from nature (e.g., soil, composts, water, etc.) or DNA samples obtained directly from natural materials (e.g., soil, composts, water, etc.) using the above-mentioned probes. Techniques for isolating microorganisms and DNA directly from natural habitats are well known in the art. A polynucleotide encoding a parent may then be obtained by similarly screening a genomic DNA or cDNA library of another microorganism or mixed DNA sample. Once a polynucleotide encoding a parent has been detected with the probe(s), the polynucleotide can be isolated or cloned by utilizing techniques that are known to those of ordinary skill in the art (see, e.g., Sambrook et al., 1989, supra).

Preparation of Variants

The present invention also relates to a method for obtaining a protease variant having at least one improved property compared to SEQ ID NO 3, comprising a) introducing into a parent protease having at least 60% identity to of SEQ ID NO: 3 one or more of the following alterations A1L, A1*, V2I, P3*, S4*, S4C, Q6C, Q18A, L43I, E50Q, N59L, L61K, V62G, G64A, G64S, S65F, Q70T, Q70L, Q70N Q70Y, Q70F, Q70M, Q70A, Q70V, Q97K, G107N, *108aA, N109T, *109aA, N109A, S111I, S111R, Y113S, S114V, S114A, S114F, D126G, D126K, E127R, E127Q, S133H, I137N, M139L, S143R, S144P, S144R, A145E, L149R, L149T, I150L, I150T, I150S, I150V, V162S, V162E, V162Q, V162G, V162F, V162T, V162Y, I164M, S171D, G182A, G182S, Q198E, Q198D, G200C, G200S, A233S, T246M, A267S, S274V, Q275Y, L276I and T297P, wherein the variant has an amino acid sequence which is at least 70%, at least 75%, at least 80%, at least 85%, at least 90% or at least 95% identical to SEQ ID NO: 3; and b) recovering the variant.

The variants can be prepared using any mutagenesis procedure known in the art, such as site-directed mutagenesis, synthetic gene construction, semi-synthetic gene construction, random mutagenesis, shuffling, etc.

The present invention relates to a method for obtaining a protease variant having at least one improved property compared to SEQ ID NO 3, comprising introducing into a parent protease with at least 75% identity to SEQ ID NO: 3 a substitution at one or more positions: 1, 2, 3, 4, 6, 18, 43, 50, 59, 61, 62, 64, 65, 70, 107, 108, 109, 111, 113, 114, 126, 127, 133, 137, 139, 143, 144, 145, 149, 150, 162, 164, 171, 182, 198, 200, 233, 246, 267, 274, 275 or 276, wherein the variant has an amino acid sequence which is at least 75%, at least 80%, at least 85%, at least 90% or at least 95% identical to SEQ ID NO: 3; and recovering the variant.

The present invention relates to a method for obtaining a protease variant having at least one improved property compared to SEQ ID NO 3, comprising introducing into a parent protease with at least 75% identity to SEQ ID NO: 3 a substitution at two or more positions: 1, 2, 3, 4, 6, 18, 43, 50, 59, 61, 62, 64, 65, 70, 107, 108, 109, 111, 113, 114, 126, 127, 133, 137, 139, 143, 144, 145, 149, 150, 162, 164, 171, 182, 198, 200, 233, 246, 267, 274, 275 or 276, wherein the variant has an amino acid sequence which is at least 75%, at least 80%, at least 85%, at least 90% or at least 95% identical to SEQ ID NO: 3; and recovering the variant.

The variants of the invention may also be prepared by procedures such as those mentioned below.

Site-directed mutagenesis is a technique in which one or more (e.g., several) mutations are introduced at one or more defined sites in a polynucleotide encoding the parent.

Site-directed mutagenesis can be accomplished in vitro by PCR involving the use of oligonucleotide primers containing the desired mutation. Site-directed mutagenesis can also be performed in vitro by cassette mutagenesis involving the cleavage by a restriction enzyme at a site in the plasmid comprising a polynucleotide encoding the parent and subsequent ligation of an oligonucleotide containing the mutation in the polynucleotide. Usually the restriction enzyme that digests the plasmid and the oligonucleotide is the same, permitting sticky ends of the plasmid and the insert to ligate to one another. See, e.g., Scherer and Davis, 1979, *Proc. Natl. Acad. Sci. USA* 76: 4949-4955; and Barton et al., 1990, *Nucleic Acids Res.* 18: 7349-4966.

Site-directed mutagenesis can also be accomplished in vivo by methods known in the art. See, e.g., U.S. Patent Application Publication No. 2004/0171154; Storici et al., 2001, *Nature Biotechnol.* 19: 773-776; Kren et al., 1998, *Nat. Med.* 4: 285-290; and Calissano and Macino, 1996, *Fungal Genet. Newslett.* 43: 15-16.

Synthetic gene construction entails in vitro synthesis of a designed polynucleotide molecule to encode a polypeptide of interest. Gene synthesis can be performed utilizing a number of techniques, such as the multiplex microchip-based technology described by Tian et al. (2004, *Nature* 432: 1050-1054) and similar technologies wherein oligonucleotides are synthesized and assembled upon photo-programmable microfluidic chips.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, *Science* 241: 53-57; Bowie and Sauer, 1989, *Proc. Natl. Acad. Sci. USA* 86: 2152-2156; WO 95/17413; or WO 95/22625. Other methods that can be used include error-prone PCR, phage display (e.g., Lowman et al., 1991, *Biochemistry* 30: 10832-10837; U.S. Pat. No. 5,223,409; WO 92/06204) and region-directed mutagenesis (Derbyshire et al., 1986, *Gene* 46: 145; Ner et al., 1988, *DNA* 7: 127).

Mutagenesis/shuffling methods can be combined with high-throughput, automated screening methods to detect activity of cloned, mutagenized polypeptides expressed by host cells (Ness et al., 1999, *Nature Biotechnology* 17: 893-896). Mutagenized DNA molecules that encode active polypeptides can be recovered from the host cells and rapidly sequenced using standard methods in the art. These methods allow the rapid determination of the importance of individual amino acid residues in a polypeptide.

Semi-synthetic gene construction is accomplished by combining aspects of synthetic gene construction, and/or site-directed mutagenesis, and/or random mutagenesis, and/or shuffling. Semi-synthetic construction is typified by a process utilizing polynucleotide fragments that are synthesized, in combination with PCR techniques. Defined regions of genes may thus be synthesized de novo, while other regions may be amplified using site-specific mutagenic primers, while yet other regions may be subjected to error-prone PCR or non-error prone PCR amplification. Polynucleotide subsequences may then be shuffled.

Polynucleotides

The present invention also relates to isolated polynucleotides encoding a variant of the present invention.

Nucleic Acid Constructs

The present invention also relates to nucleic acid constructs comprising a polynucleotide encoding a variant of the present invention operably linked to one or more control sequences that direct the expression of the coding sequence in a suitable host cell under conditions compatible with the control sequences.

The polynucleotide may be manipulated in a variety of ways to provide for expression of a variant. Manipulation of the polynucleotide prior to its insertion into a vector may be desirable or necessary depending on the expression vector. The techniques for modifying polynucleotides utilizing recombinant DNA methods are well known in the art.

The control sequence may be a promoter, a polynucleotide which is recognized by a host cell for expression of the polynucleotide. The promoter contains transcriptional control sequences that mediate the expression of the variant. The promoter may be any polynucleotide that shows transcriptional activity in the host cell including variant, truncated, and hybrid promoters, and may be obtained from genes encoding extracellular or intracellular polypeptides either homologous or heterologous to the host cell.

Examples of suitable promoters for directing transcription of the nucleic acid constructs of the present invention in a bacterial host cell are the promoters obtained from the *Bacillus amyloliquefaciens* alpha-amylase gene (amyQ), *Bacillus licheniformis* alpha-amylase gene (amyL), *Bacillus licheniformis* penicillinase gene (penP), *Bacillus stearothermophilus* maltogenic amylase gene (amyM), *Bacillus subtilis* levansucrase gene (sacB), *Bacillus subtilis* xylA and xylB genes, *Bacillus thuringiensis* cryIIIA gene (Agaisse and Lereclus, 1994, *Molecular Microbiology* 13: 97-107), *E. coli* lac operon, *E. coli* trc promoter (Egon et al., 1988, *Gene* 69: 301-315), *Streptomyces coelicolor* agarase gene (dagA), and prokaryotic beta-lactamase gene (Villa-Kamaroff et al., 1978, *Proc. Natl. Acad. Sci. USA* 75: 3727-3731), as well as the tac promoter (DeBoer et al., 1983, *Proc. Natl. Acad. Sci. USA* 80: 21-25). Further promoters are described in "Useful proteins from recombinant bacteria" in Gilbert et al., 1980, *Scientific American* 242: 74-94; and in Sambrook et al., 1989, supra. Examples of tandem promoters are disclosed in WO 99/43835.

The control sequence may also be a transcription terminator, which is recognized by a host cell to terminate transcription. The terminator sequence is operably linked to the 3'-terminus of the polynucleotide encoding the variant. Any terminator that is functional in the host cell may be used.

Preferred terminators for bacterial host cells are obtained from the genes for *Bacillus clausii* alkaline protease (aprH), *Bacillus licheniformis* alpha-amylase (amyL), and *Escherichia coli* ribosomal RNA (rrnB).

The control sequence may also be an mRNA stabilizer region downstream of a promoter and upstream of the coding sequence of a gene which increases expression of the gene.

Examples of suitable mRNA stabilizer regions are obtained from a *Bacillus thuringiensis* cryIIIA gene (WO 94/25612) and a *Bacillus subtilis* SP82 gene (Hue et al., 1995, *Journal of Bacteriology* 177: 3465-3471).

The control sequence may also be a signal peptide coding region that encodes a signal peptide linked to the N-terminus of a variant and directs the variant into the cell's secretory pathway. The 5'-end of the coding sequence of the polynucleotide may inherently contain a signal peptide coding sequence naturally linked in translation reading frame with the segment of the coding sequence that encodes the variant. Alternatively, the 5'-end of the coding sequence may contain a signal peptide coding sequence that is foreign to the coding sequence. A foreign signal peptide coding sequence may be required where the coding sequence does not naturally contain a signal peptide coding sequence. Alternatively, a foreign signal peptide coding sequence may simply replace the natural signal peptide coding sequence in order to enhance secretion of the variant. However, any signal peptide coding sequence that directs the expressed variant into the secretory pathway of a host cell may be used.

Effective signal peptide coding sequences for bacterial host cells are the signal peptide coding sequences obtained from the genes for *Bacillus* NCIB 11837 maltogenic amylase, *Bacillus licheniformis* subtilisin, *Bacillus licheniformis* beta-lactamase, *Bacillus stearothermophilus* alpha-amylase, *Bacillus stearothermophilus* neutral proteases (nprT, nprS, nprM), and *Bacillus subtilis* prsA. Further signal peptides are described by Simonen and Palva, 1993, *Microbiological Reviews* 57: 109-137.

The control sequence may also be a propeptide coding sequence that encodes a propeptide positioned at the N-terminus of a variant. The resultant polypeptide is known as a proenzyme or propolypeptide (or a zymogen in some cases). A propolypeptide is generally inactive and can be converted to an active polypeptide by catalytic or autocatalytic cleavage of the propeptide from the propolypeptide. The propeptide coding sequence may be obtained from the genes for *Bacillus subtilis* alkaline protease (aprE), *Bacillus subtilis* neutral protease (nprT), *Myceliophthora thermophila* laccase (WO 95/33836), *Rhizomucor miehei* aspartic proteinase, and *Saccharomyces cerevisiae* alpha-factor.

Where both signal peptide and propeptide sequences are present, the propeptide sequence is positioned next to the N-terminus of the variant and the signal peptide sequence is positioned next to the N-terminus of the propeptide sequence.

It may also be desirable to add regulatory sequences that regulate expression of the variant relative to the growth of the host cell. Examples of regulatory systems are those that cause expression of the gene to be turned on or off in response to a chemical or physical stimulus, including the presence of a regulatory compound. Regulatory systems in prokaryotic systems include the lac, tac, and trp operator systems.

Expression Vectors

The present invention also relates to recombinant expression vectors comprising a polynucleotide encoding a variant of the present invention, a promoter, and transcriptional and translational stop signals. The various nucleotide and control sequences may be joined together to produce a recombinant expression vector that may include one or more convenient restriction sites to allow for insertion or substitution of the polynucleotide encoding the variant at such sites. Alternatively, the polynucleotide may be expressed by inserting the polynucleotide or a nucleic acid construct comprising the polynucleotide into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the polynucleotide. The choice of the vector will typically depend on the compatibility of the vector with the host cell into which the vector is to be introduced. The vector may be a linear or closed circular plasmid.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vector preferably contains one or more selectable markers that permit easy selection of transformed, transfected, transduced, or the like cells. A selectable marker is a gene the product of which provides for biocide or viral resistance, resistance to heavy metals, prototrophy to auxotrophs, and the like.

Examples of bacterial selectable markers are *Bacillus licheniformis* or *Bacillus subtilis* dal genes, or markers that confer antibiotic resistance such as ampicillin, chloramphenicol, kanamycin, neomycin, spectinomycin or tetracycline resistance.

The vector preferably contains an element(s) that permits integration of the vector into the host cell's genome or autonomous replication of the vector in the cell independent of the genome.

For integration into the host cell genome, the vector may rely on the polynucleotide's sequence encoding the variant or any other element of the vector for integration into the genome by homologous or non-homologous recombination. Alternatively, the vector may contain additional polynucleotides for directing integration by homologous recombination into the genome of the host cell at a precise location(s) in the chromosome(s). To increase the likelihood of integration at a precise location, the integrational elements should contain a sufficient number of nucleic acids, such as 100 to 10,000 base pairs, 400 to 10,000 base pairs, and 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding polynucleotides. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" means a polynucleotide that enables a plasmid or vector to replicate in vivo.

Examples of bacterial origins of replication are the origins of replication of plasmids pBR322, pUC19, pACYC177, and pACYC184 permitting replication in *E. coli*, and pUB110, pE194, pTA1060, and pAMβ1 permitting replication in *Bacillus*.

More than one copy of a polynucleotide of the present invention may be inserted into a host cell to increase production of a variant. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a polynucleotide encoding a variant of the present invention operably linked to one or more control sequences that direct the production of a variant of the present invention. A construct or vector comprising a polynucleotide is introduced into a host cell so that the construct or vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the variant and its source.

The host cell may be any cell useful in the recombinant production of a variant, e.g., a prokaryote or a eukaryote.

The prokaryotic host cell may be any Gram-positive or Gram-negative bacterium. Gram-positive bacteria include, but are not limited to, *Bacillus, Clostridium, Enterococcus, Geobacillus, Lactobacillus, Lactococcus, Oceanobacillus, Staphylococcus, Streptococcus*, and *Streptomyces*. Gram-negative bacteria include, but are not limited to, *Campylobacter, E. coli, Flavobacterium, Fusobacterium, Helicobacter, Ilyobacter, Neisseria, Pseudomonas, Salmonella*, and *Ureaplasma*.

The bacterial host cell may be any *Bacillus* cell including, but not limited to, *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis*, and *Bacillus thuringiensis* cells.

The bacterial host cell may also be any *Streptococcus* cell including, but not limited to, *Streptococcus equisimilis, Streptococcus pyogenes, Streptococcus uberis*, and *Streptococcus equi* subsp. *Zooepidemicus* cells.

The bacterial host cell may also be any *Streptomyces* cell, including, but not limited to, *Streptomyces achromogenes, Streptomyces avermitilis, Streptomyces coelicolor, Streptomyces griseus*, and *Streptomyces lividans* cells.

The introduction of DNA into a *Bacillus* cell may be effected by protoplast transformation (see, e.g., Chang and Cohen, 1979, *Mol. Gen. Genet.* 168: 111-115), competent cell transformation (see, e.g., Young and Spizizen, 1961, *J. Bacteriol.* 81: 823-829, or Dubnau and Davidoff-Abelson, 1971, *J. Mol. Biol.* 56: 209-221), electroporation (see, e.g., Shigekawa and Dower, 1988, *Biotechniques* 6: 742-751), or conjugation (see, e.g., Koehler and Thorne, 1987, *J. Bacteriol.* 169: 5271-5278). The introduction of DNA into an *E. coli* cell may be effected by protoplast transformation (see, e.g., Hanahan, 1983, *J. Mol. Biol.* 166: 557-580) or electroporation (see, e.g., Dower et al., 1988, *Nucleic Acids Res.* 16: 6127-6145). The introduction of DNA into a *Streptomyces* cell may be effected by protoplast transformation, electroporation (see, e.g., Gong et al., 2004, *Folia Microbiol. (Praha)* 49: 399-405), conjugation (see, e.g., Mazodier et al., 1989, *J. Bacteriol.* 171: 3583-3585), or transduction (see, e.g., Burke et al., 2001, *Proc. Natl. Acad. Sci. USA* 98: 6289-6294). The introduction of DNA into a *Pseudomonas* cell may be effected by electroporation (see, e.g., Choi et al., 2006, *J. Microbiol. Methods* 64: 391-397), or conjugation (see, e.g., Pinedo and Smets, 2005, *Appl. Environ. Microbiol.* 71: 51-57). The introduction of DNA into a *Streptococcus* cell may be effected by natural competence (see, e.g., Perry and Kuramitsu, 1981, *Infect. Immun.* 32: 1295-1297), protoplast transformation (see, e.g., Catt and Jollick, 1991, *Microbios* 68: 189-207), electroporation (see, e.g., Buckley et al., 1999, *Appl. Environ. Microbiol.* 65: 3800-3804) or conjugation (see, e.g., Clewell, 1981, *Microbiol. Rev.* 45: 409-436). However, any method known in the art for introducing DNA into a host cell can be used.

Methods of Production

The present invention also relates to methods of producing a variant, comprising: (a) cultivating a host cell of the present invention under conditions suitable for expression of the variant; and (b) recovering the variant.

The host cells are cultivated in a nutrient medium suitable for production of the variant using methods known in the art. For example, the cell may be cultivated by shake flask cultivation, or small-scale or large-scale fermentation (including continuous, batch, fed-batch, or solid state fermentations) in laboratory or industrial fermentors performed in a suitable medium and under conditions allowing the variant to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the variant is secreted into the nutrient medium, the variant can be recovered directly from the medium. If the variant is not secreted, it can be recovered from cell lysates.

The variant may be detected using methods known in the art that are specific for the variants with protease activity. These detection methods include, but are not limited to, use of specific antibodies, formation of an enzyme product, or disappearance of an enzyme substrate. For example, an enzyme assay may be used to determine the activity of the variant.

The variant may be recovered using methods known in the art. For example, the variant may be recovered from the nutrient medium by conventional procedures including, but not limited to, collection, centrifugation, filtration, extraction, spray-drying, evaporation, or precipitation.

The variant may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., Protein Purification, Janson and Ryden, editors, VCH Publishers, New York, 1989) to obtain substantially pure variants.

In an alternative aspect, the variant is not recovered, but rather a host cell of the present invention expressing the variant is used as a source of the variant.

Compositions

Besides enzymes the detergent compositions may comprise additional components. The choice of additional components is within the skill of the artisan and includes conventional ingredients, including the exemplary non-limiting components set forth below. The choice of components may include, for fabric care, the consideration of the type of fabric to be cleaned, the type and/or degree of soiling, the temperature at which cleaning is to take place, and the formulation of the detergent product. Although components mentioned below are categorized by general header according to a particular functionality, this is not to be construed as a limitation, as a component may comprise additional functionalities as will be appreciated by the skilled artisan.

Detergent Compositions of the Present Invention

The protease variants of the present invention may be added to a detergent composition in an amount corresponding to 0.001-100 mg of protein, such as 0.01-100 mg of protein, preferably 0.005-50 mg of protein, more preferably 0.01-25 mg of protein, even more preferably 0.05-10 mg of protein, most preferably 0.05-5 mg of protein, and even most preferably 0.01-1 mg of protein per liter of wash liquor.

The detergent composition may comprise one or more surfactants, which may be anionic and/or cationic and/or non-ionic and/or semi-polar and/or zwitterionic, or a mixture thereof. In a particular embodiment, the detergent composition includes a mixture of one or more nonionic surfactants and one or more anionic surfactants. The surfactant(s) is typically present at a level of from about 0.1% to 60% by weight, such as about 1% to about 40%, or about 3% to about 20%, or about 3% to about 10%. The surfactant(s) is chosen based on the desired cleaning application, and includes any conventional surfactant(s) known in the art. Any surfactant known in the art for use in detergents may be utilized.

When included therein, the detergent will usually contain from about 1% to about 40% by weight, such as from about 5% to about 30%, including from about 5% to about 15%, or from about 20% to about 25% of an anionic surfactant. Non-limiting examples of anionic surfactants include sulfates and sulfonates, in particular, linear alkylbenzenesulfonates (LAS), isomers of LAS, branched alkylbenzenesulfonates (BABS), phenylalkanesulfonates, alpha-olefinsulfonates (AOS), olefin sulfonates, alkene sulfonates, alkane-2,3-diylbis(sulfates), hydroxyalkanesulfonates and disulfonates, alkyl sulfates (AS) such as sodium dodecyl sulfate (SDS), fatty alcohol sulfates (FAS), primary alcohol sulfates (PAS), alcohol ethersulfates (AES or AEOS or FES, also known as alcohol ethoxysulfates or fatty alcohol ether sulfates), secondary alkanesulfonates (SAS), paraffin sulfonates (PS), ester sulfonates, sulfonated fatty acid glycerol esters, alpha-sulfo fatty acid methyl esters (alpha-SFMe or SES) including methyl ester sulfonate (MES), alkyl- or alkenylsuccinic acid, dodecenyl/tetradecenyl succinic acid (DTSA), fatty acid derivatives of amino acids, diesters and monoesters of sulfo-succinic acid or soap, and combinations thereof.

When included therein, the detergent will usually contain from about 1% to about 40% by weight of a cationic surfactant. Non-limiting examples of cationic surfactants include alklydimethylehanolamine quat (ADMEAQ), cetyltrimethylammonium bromide (CTAB), dimethyldistearylammonium chloride (DSDMAC), and alkylbenzyldimethylammonium, and combinations thereof, Alkyl quaternary ammonium compounds, Alkoxylated quaternary ammonium (AQA), When included therein, the detergent will usually contain from about 0.2% to about 40% by weight of a non-ionic surfactant, for example from about 0.5% to about 30%, in particular from about 1% to about 20%, from about 3% to about 10%, such as from about 3% to about 5%, or from about 8% to about 12%. Non-limiting examples of non-ionic surfactants include alcohol ethoxylates (AE or AEO), alcohol propoxylates, propoxylated fatty alcohols (PFA), alkoxylated fatty acid alkyl esters, such as ethoxylated and/or propoxylated fatty acid alkyl esters, alkylphenol ethoxylates (APE), nonylphenol ethoxylates (NPE), alkylpolyglycosides (APG), alkoxylated amines, fatty acid monoethanolamides (FAM), fatty acid diethanolamides (FADA), ethoxylated fatty acid monoethanolamides (EFAM), propoxylated fatty acid monoethanolamide (PFAM), polyhydroxy alkyl fatty acid amides, or N-acyl N-alkyl derivatives of glucosamine (glucamides, GA, or fatty acid glucamide, FAGA), as well as products available under the trade names SPAN and TWEEN, and combinations thereof.

When included therein, the detergent will usually contain from about 1% to about 40% by weight of a semipolar surfactant. Non-limiting examples of semipolar surfactants include amine oxides (AO) such as alkyldimethylamineoxide, N-(coco alkyl)-N,N-dimethylamine oxide and N-(tallow-alkyl)-N,N-bis(2-hydroxyethyl)amine oxide, fatty acid alkanolamides and ethoxylated fatty acid alkanolamides, and combinations thereof.

When included therein, the detergent will usually contain from about 1% to about 40% by weight of a zwitterionic surfactant. Non-limiting examples of zwitterionic surfactants include betaine, alkyldimethylbetaine, and sulfobetaine, and combinations thereof.

The compositions of the invention may also comprise a hydrotrope which is a compound that solubilises hydrophobic compounds in aqueous solutions (or oppositely, polar substances in a non-polar environment). Typically, hydrotropes have both hydrophilic and a hydrophobic character (so-called amphiphilic properties as known from surfactants); however the molecular structure of hydrotropes generally do not favor spontaneous self-aggregation, see e.g. review by Hodgdon and Kaler (2007), Current Opinion in Colloid & Interface Science 12: 121-128. Hydrotropes do not display a critical concentration above which self-aggregation occurs as found for surfactants and lipids forming miceller, lamellar or other well defined meso-phases. Instead, many hydrotropes show a continuous-type aggregation process where the sizes of aggregates grow as concentration increases. However, many hydrotropes alter the phase behavior, stability, and colloidal properties of systems containing substances of polar and non-polar character, including mixtures of water, oil, surfactants, and polymers. Hydrotropes are classically used across industries from pharma, personal care, food, to technical applications. Use of hydrotropes in detergent compositions allow for example more concentrated formulations of surfactants (as in the process of compacting liquid detergents by removing water) without inducing undesired phenomena such as phase separation or high viscosity.

The detergent may contain 0-5% by weight, such as about 0.5 to about 5%, or about 3% to about 5%, of a hydrotrope. Any hydrotrope known in the art for use in detergents may be utilized. Non-limiting examples of hydrotropes include sodium benzene sulfonate, sodium p-toluene sulfonates (STS), sodium xylene sulfonates (SXS), sodium cumene sulfonates (SCS), sodium cymene sulfonate, amine oxides, alcohols and polyglycolethers, sodium hydroxynaphthoate, sodium hydroxynaphthalene sulfonate, sodium ethylhexyl sulfate, and combinations thereof.

The detergent composition may contain about 0-65% by weight, such as about 5% to about 50% of a detergent builder or co-builder, or a mixture thereof. In a dish wash deteregent, the level of builder is typically 40-65%, particularly 50-65%. The builder and/or co-builder may particularly be a chelating agent that forms water-soluble complexes with Ca and Mg. Any builder and/or co-builder known in the art for use in laundry, ADW and hard surfaces cleaning detergents may be utilized. Non-limiting examples of builders include zeolites, diphosphates (pyrophosphates), triphosphates such as sodium triphosphate (STP or STPP), carbonates such as sodium carbonate, soluble silicates such as sodium metasilicate, layered silicates (e.g., SKS-6 from Hoechst), ethanolamines such as 2-aminoethan-1-ol (MEA), iminodiethanol (DEA) and 2,2',2"-nitrilotriethanol (TEA), and carboxymethylinulin (CMI), and combinations thereof.

The detergent composition may also contain 0-65% by weight, such as about 5% to about 40%, of a detergent co-builder, or a mixture thereof. The detergent composition may include a co-builder alone, or in combination with a builder, for example a zeolite builder. Non-limiting examples of co-builders include homopolymers of polyacrylates or copolymers thereof, such as poly(acrylic acid) (PAA) or copoly(acrylic acid/maleic acid) (PAA/PMA). Further non-limiting examples include citrate, chelators such as aminocarboxylates, aminopolycarboxylates and phosphonates, and alkyl- or alkenylsuccinic acid. Additional specific examples include 2,2',2"-nitrilotriacetic acid (NTA), etheylenediaminetetraacetic acid (EDTA), diethylenetriaminepentaacetic acid (DTPA), iminodisuccinic acid (IDS), ethylenediamine-N,N'-disuccinic acid (EDDS), methylglycinediacetic acid (MGDA), glutamic acid-N,N-diacetic acid (GLDA), 1-hydroxyethane-1,1-diylbis(phosphonic acid) (HEDP), ethylenediaminetetrakis(methylene)tetrakis(phosphonic acid) (EDTMPA), diethylenetriaminepentakis(methylene)pentakis(phosphonic acid) (DTPMPA), N-(2-hydroxyethyl)iminodiacetic acid (EDG), aspartic acid-N-monoacetic acid (ASMA), aspartic acid-N,N-diacetic acid (ASDA), aspartic acid-N-monopropionic acid (ASMP), iminodisuccinic acid (IDA), N-(2-sulfomethyl) aspartic acid (SMAS), N-(2-sulfoethyl) aspartic acid (SEAS), N-(2-sulfomethyl) glutamic acid (SMGL), N-(2-sulfoethyl) glutamic acid (SEGL), N-methyliminodiacetic acid (MIDA), α-alanine-N,N-diacetic acid (α-ALDA), serine-N,N-diacetic acid (SEDA), isoserine-N,N-diacetic acid (ISDA), phenylalanine-N,N-diacetic acid (PHDA), anthranilic acid-N,N-diacetic acid (ANDA), sulfanilic acid-N, N-diacetic acid (SLDA), taurine-N, N-diacetic acid (TUDA) and sulfomethyl-N,N-diacetic acid (SMDA), N-(hydroxyethyl)-ethylidenediaminetriacetate (HEDTA), diethanoiglycine (DEG), Diethylenetriamine Penta (Methylene Phosphonic acid) (DTPMP), aminotris(methylenephosphonic acid) (ATMP), and combinations and salts thereof. Further exemplary builders and/or co-builders are described in, e.g., WO 09/102854, U.S. Pat. No. 5,977,053.

The detergent may contain 0-10% by weight, such as about 1% to about 5%, of a bleaching system. Any bleaching system known in the art for use in laundry, ADW and hard surfaces cleaning detergents may be utilized. Suitable bleaching system components include bleaching catalysts, photobleaches, bleach activators, sources of hydrogen peroxide such as sodium percarbonate and sodium perborates, preformed peracids and mixtures thereof. Suitable preformed peracids include, but are not limited to, peroxycarboxylic acids and salts, percarbonic acids and salts, perimidic acids and salts, peroxymonosulfuric acids and salts, for example, Oxone (R), and mixtures thereof. Non-limiting examples of bleaching systems include peroxide-based bleaching systems, which may comprise, for example, an inorganic salt, including alkali metal salts such as sodium salts of perborate (usually mono- or tetra-hydrate), percarbonate, persulfate, perphosphate, persilicate salts, in combination with a peracid-forming bleach activator. By bleach activator is meant herin a compound which reacts with peroxygen bleach like hydrogen peroxide to form a peracid. The peracid thus formed constitutes the activated bleach. Suitable bleach activators to be used herein include those belonging to the class of esters amides, imides or anhydrides. Suitable examples are tetracetyl athylene diamine (TAED), sodium 3,5,5 trimethyl hexanoyloxybenzene suiphonat, diperoxy dodecanoic acid, 4-(dodecanoyloxy)benzenesulfonate (LOBS), 4-(decanoyloxy)benzenesulfonate, 4-(decanoyloxy)benzoate (DOBS), 4-(3,5,5-trimethylhexanoyloxy)benzenesulfonate (ISONOBS), tetraacetylethylenediamine (TAED) and 4-(nonanoyloxy)benzenesulfonate (NOBS), and/or those disclosed in WO98/17767. A particular family of bleach activators of interest was disclosed in EP624154 and particulary preferred in that family is acetyl triethyl citrate (ATC). ATC or a short chain triglyceride like Triacin has the advantage that it is environmental friendly as it eventually degrades into citric acid and alcohol. Furthermore acethyl triethyl citrate and triacetin has a good hydrolytical stability in the product upon storage and it is an efficient bleach activator. Finally ATC provides a good building capacity to the laundry additive. Alternatively, the bleaching system may comprise peroxyacids of, for example, the amide, imide, or sulfone type. The bleaching system may also comprise peracids such as 6-(phthaloylamino)percapronic acid (PAP). The bleaching system may also include a bleach catalyst. In some embodiments the bleach component may be an organic catalyst selected from the group consisting of organic catalysts having the following formulae:

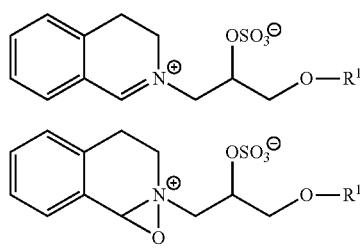

(iii) and mixtures thereof; wherein each $R^1$ is independently a branched alkyl group containing from 9 to 24 carbons or linear alkyl group containing from 11 to 24 carbons, preferably each $R^1$ is independently a branched alkyl group containing from 9 to 18 carbons or linear alkyl group containing from 11 to 18 carbons, more preferably each $R^1$ is independently selected from the group consisting of 2-propylheptyl, 2-butyloctyl, 2-pentylnonyl, 2-hexyldecyl, n-dodecyl, n-tetradecyl, n-hexadecyl, n-octadecyl, iso-nonyl, iso-decyl, iso-tridecyl and iso-pentadecyl. Other exemplary bleaching systems are described, e.g., in WO2007/087258, WO2007/087244, WO2007/087259, WO2007/087242. Suitable photobleaches may for example be sulfonated zinc phthalocyanine The cleaning composition may contain 0-10% by weight, such as 0.5-5%, 2-5%, 0.5-2% or 0.2-1% of a polymer. Any polymer known in the art for use in detergents may be utilized. The polymer may function as a co-builder as mentioned above, or may provide antiredeposition, fiber protection, soil release, dye transfer inhibition, grease cleaning and/or anti-foaming properties. Some polymers may have more than one of the above-mentioned properties and/or more than one of the below-mentioned motifs. Exemplary polymers include (carboxymethyl)cellulose (CMC), poly(vinyl alcohol) (PVA), poly(vinylpyrrolidone) (PVP), polyethyleneglycol) or poly(ethylene oxide) (PEG), ethoxylated poly(ethyleneimine), carboxymethyl inulin (CMI), and polycarboxylates such as PM, PAA/PMA, poly-aspartic acid, and lauryl methacrylate/acrylic acid copolymers, hydrophobically modified CMC (HM-CMC) and silicones, copolymers of terephthalic acid and oligomeric glycols, copolymers of polyethylene terephthalate and polyoxyethene terephthalate (PET-POET), PVP, poly(vinylimidazole) (PVI), poly(vinylpyridin-N-oxide) (PVPO or PVPNO) and polyvinylpyrrolidone-vinylimidazole (PVPVI). Further exemplary polymers include sulfonated polycarboxylates, polyethylene oxide and polypropylene oxide (PEO-PPO) and diquatemium ethoxy sulfate. Other exemplary polymers are disclosed in, e.g., WO 2006/130575. Salts of the above-mentioned polymers are also contemplated.

The cleaning compositions may also include fabric hueing agents such as dyes or pigments which when formulated in detergent compositions can deposit onto a fabric when said fabric is contacted with a wash liquor comprising said detergent compositions thus altering the tint of said fabric through absorption/reflection of visible light. Fluorescent whitening agents emit at least some visible light. In contrast, fabric hueing agents alter the tint of a surface as they absorb at least a portion of the visible light spectrum. Suitable fabric hueing agents include dyes and dye-clay conjugates, and may also include pigments. Suitable dyes include small molecule dyes and polymeric dyes. Suitable small molecule dyes include small molecule dyes selected from the group consisting of dyes falling into the Colour Index (C.I.) classifications of Direct Blue, Direct Red, Direct Violet, Acid Blue, Acid Red, Acid Violet, Basic Blue, Basic Violet and Basic Red, or mixtures thereof, for example as described in WO2005/03274, WO2005/03275, WO2005/03276 and EP1876226 (hereby incorporated by reference). A detergent composition preferably comprises from about 0.00003 wt % to about 0.2 wt %, from about 0.00008 wt % to about 0.05 wt %, or even from about 0.0001 wt % to about 0.04 wt % fabric hueing agent. The composition may comprise from 0.0001 wt % to 0.2 wt % fabric hueing agent, this may be especially preferred when the composition is in the form of a unit dose pouch. Suitable hueing agents are also disclosed in, e.g., WO 2007/087257, WO2007/087243.

In one embodiment, the variants according to the invention are combined with one or more enzymes, such as at least two enzymes, more preferred at least three, four or five enzymes. Preferably, the enzymes have different substrate specificity, e.g., proteolytic activity, amylolytic activity, lipolytic activity, hemicellulytic activity or pectolytic activity.

The detergent additive as well as the detergent composition may comprise one or more additional enzymes such as carbohydrate-active enzymes like carbohydrase, pectinase, mannanase, amylase, cellulase, arabinase, galactanase, xylanase, or protease, lipase, a, cutinase, oxidase, e.g., a laccase, and/or peroxidase.

In general, the properties of the selected enzyme(s) should be compatible with the selected detergent, (i.e., pH-optimum, compatibility with other enzymatic and non-enzymatic ingredients, etc.), and the enzyme(s) should be present in effective amounts.

Cellulases:

Suitable cellulases include those of bacterial or fungal origin. Chemically modified or protein engineered variants are included. Suitable cellulases include cellulases from the genera *Bacillus, Pseudomonas, Humicola, Fusarium, Thielavia, Acremonium*, e.g., the fungal cellulases produced from *Humicola insolens, Myceliophthora* thermophile and *Fusarium oxysporum* disclosed in U.S. Pat. Nos. 4,435,307, 5,648,263, 5,691,178, 5,776,757 and WO 89/09259.

Especially suitable cellulases are the alkaline or neutral cellulases having colour care benefits. Examples of such cellulases are cellulases described in EP 0 495 257, EP 0 531 372, WO 96/11262, WO 96/29397, WO 98/08940. Other examples are cellulase variants such as those described in WO 94/07998, EP 0 531 315, U.S. Pat. Nos. 5,457,046, 5,686,593, 5,763,254, WO 95/24471, WO 98/12307 and WO99/001544.

Other cellulases are endo-beta-1,4-glucanase enzyme having a sequence of at least 97% identity to the amino acid sequence of position 1 to position 773 of SEQ ID NO:2 of WO 2002/099091 or a family 44 xyloglucanase, which a xyloglucanase enzyme having a sequence of at least 60% identity to positions 40-559 of SEQ ID NO: 2 of WO 2001/062903.

Commercially available cellulases include Celluzyme™, and Carezyme™ (Novozymes A/S) Carezyme Premium™ (Novozymes A/S), Celluclean™ (Novozymes A/S), Celluclean Classic™ (Novozymes A/S), Cellusoft™ (Novozymes NS), Whitezyme™ (Novozymes A/S), Clazinase™, and Puradax HA™ (Genencor International Inc.), and KAC-500(B)™ (Kao Corporation).

Mannanases

Suitable mannanases include those of bacterial or fungal origin. Chemically or genetically modified variants are included. The mannanase may be an alkaline mannanase of Family 5 or 26. It may be a wild-type from *Bacillus* or *Humicola*, particularly *B. agaradhaerens*, *B. licheniformis*, *B. halodurans*, *B. clausii*, or *H. insolens*. Suitable mannanases are described in WO 1999/064619. A commercially available mannanase is Mannaway (Novozymes A/S).

Proteases:

Suitable additional proteases include those of bacterial, fungal, plant, viral or animal origin e.g. vegetable or microbial origin. Microbial origin is preferred. Chemically modified or protein engineered variants are included. It may be an alkaline protease, such as a serine protease or a metalloprotease. A serine protease may for example be of the S1 family, such as trypsin, or the S8 family such as subtilisin. A metalloproteases protease may for example be a thermolysin from e.g. family M4 or other metalloprotease such as those from M5, M7 or M8 families.

The term "subtilases" refers to a sub-group of serine protease according to Siezen et al., Protein Engng. 4 (1991) 719-737 and Siezen et al. Protein Science 6 (1997) 501-523. Serine proteases are a subgroup of proteases characterized by having a serine in the active site, which forms a covalent adduct with the substrate. The subtilases may be divided into 6 sub-divisions, i.e. the Subtilisin family, the Thermitase family, the Proteinase K family, the Lantibiotic peptidase family, the Kexin family and the Pyrolysin family.

Examples of subtilases are those derived from *Bacillus* such as *Bacillus lentus*, *B. alkalophilus*, *B. subtilis*, *B. amyloliquefaciens*, *Bacillus pumilus* and *Bacillus gibsonii* described in; U.S. Pat. No. 7,262,042 and WO09/021867, and subtilisin *lentus*, subtilisin Novo, subtilisin Carlsberg, *Bacillus licheniformis*, subtilisin BPN', subtilisin 309, subtilisin 147 and subtilisin 168 described in WO89/06279 and protease PD138 described in (WO93/18140). Other useful proteases may be those described in WO92/175177, WO01/016285, WO02/026024 and WO02/016547. Examples of trypsin-like proteases are trypsin (e.g. of porcine or bovine origin) and the *Fusarium* protease described in WO89/06270, WO94/25583 and WO05/040372, and the chymotrypsin proteases derived from *Cellulomonas* described in WO05/052161 and WO05/052146.

A further preferred protease is the alkaline protease from *Bacillus lentus* DSM 5483, as described for example in WO95/23221, and variants thereof which are described in WO92/21760, WO95/23221, EP1921147 and EP1921148.

Examples of metalloproteases are the neutral metalloprotease as described in WO07/044993 (Genencor Int.) such as those derived from *Bacillus amyloliquefaciens*.

Examples of useful proteases are the variants described in: WO92/19729, WO96/034946, WO98/20115, WO98/20116, WO99/011768, WO01/44452, WO03/006602, WO04/03186, WO04/041979, WO07/006305, WO11/036263, WO11/036264, especially the variants with substitutions in one or more of the following positions: 3, 4, 9, 15, 27, 36, 57, 68, 76, 87, 95, 96, 97, 98, 99, 100, 101, 102, 103, 104, 106, 118, 120, 123, 128, 129, 130, 160, 167, 170, 194, 195, 199, 205, 206, 217, 218, 222, 224, 232, 235, 236, 245, 248, 252 and 274 using the BPN' numbering. More preferred the protease variants may comprise the mutations: S3T, V4I, S9R, A15T, K27R, *36D, V68A, N76D, N87S, R, *97E, A98S, S99G, D, A, S99AD, S101G, M, R S103A, V104I, Y, N, S106A, G118V, R, H120D, N, N123S, S128L, P129Q, S130A, G160D, Y167A, R170S, A194P, G195E, V199M, V205I, L217D, N218D, M222S, A232V, K235L, Q236H, Q245R, N252K, T274A (using BPN' numbering).

Suitable commercially available protease enzymes include those sold under the trade names Alcalase®, Duralase™, Durazym™, Relase®, Relase® Ultra, Savinase®, Savinase® Ultra, Primase®, Polarzyme®, Kannase®, Liquanase®, Liquanase® Ultra, BLAZE®, Ovozyme®, Coronase®, Coronase® Ultra, Neutrase®, Everlase® and Esperase® (Novozymes NS), those sold under the tradename Maxatase®, Maxacal®, Maxapem®, Purafect®, Purafect Prime®, Purafect MA®, Purafect Ox®, Purafect OxP®, Puramax®, Properase®, FN2®, FN3®, FN4®, Excellase®, Eraser®, Ultimase®, Opticlean® and Optimase® (Danisco/DuPont), Axapem™ (Gist-Brocases N.V.), BLAP (sequence shown in FIG. 29 of U.S. Pat. No. 5,352,604) and variants hereof (Henkel AG) and KAP (*Bacillus alkalophilus* subtilisin) from Kao.

Lipases and Cutinases:

Suitable lipases and cutinases include those of bacterial or fungal origin. Chemically modified or protein engineered variant enzymes are included. Examples include lipase from *Thermomyces*, e.g. from *T. lanuginosus* (previously named *Humicola lanuginosa*) as described in EP258068 and EP305216, cutinase from *Humicola*, e.g. *H. insolens* (WO96/13580), lipase from strains of *Pseudomonas* (some of these now renamed to *Burkholderia*), e.g. *P. alcaligenes* or *P. pseudoalcaligenes* (EP218272), *P. cepacia* (EP331376), *P.* sp. strain SD705 (WO95/06720 & WO96/27002), *P. wisconsinensis* (WO96/12012), GDSL-type *Streptomyces* lipases (WO10/065455), cutinase from *Magnaporthe grisea* (WO10/107560), cutinase from *Pseudomonas mendocina* (U.S. Pat. No. 5,389,536), lipase from *Thermobifida fusca* (WO11/084412), *Geobacillus stearothermophilus* lipase (WO11/084417), lipase from *Bacillus subtilis* (WO11/084599), and lipase from *Streptomyces griseus* (WO11/150157) and *S. pristinaespiralis* (WO12/137147).

Other examples are lipase variants such as those described in EP407225, WO92/05249, WO94/01541, WO94/25578, WO95/14783, WO95/30744, WO95/35381, WO95/22615, WO96/00292, WO97/04079, WO97/07202, WO00/34450, WO00/60063, WO01/92502, WO07/87508 and WO09/109500.

Preferred commercial lipase products include include Lipolase™, Lipex™; Lipolex™ and Lipoclean™ (Novozymes A/S), Lumafast (originally from Genencor) and Lipomax (originally from Gist-Brocades).

Still other examples are lipases sometimes referred to as acyltransferases or perhydrolases, e.g. acyltransferases with homology to *Candida antarctica* lipase A (WO10/111143), acyltransferase from *Mycobacterium smegmatis* (WO05/56782), perhydrolases from the CE 7 family (WO09/67279), and variants of the *M. smegmatis* perhydrolase in particular the S54V variant used in the commercial product Gentle Power Bleach from Huntsman Textile Effects Pte Ltd (WO10/100028).

Amylases:

Suitable amylases which can be used together with the protease variants of the invention may be an alpha-amylase or a glucoamylase and may be of bacterial or fungal origin. Chemically modified or protein engineered variants are included. Amylases include, for example, alpha-amylases obtained from *Bacillus*, e.g., a special strain of *Bacillus licheniformis*, described in more detail in GB 1,296,839.

Suitable amylases include amylases having SEQ ID NO: 2 in WO 95/10603 or variants having 90% sequence identity to SEQ ID NO: 3 thereof. Preferred variants are described in WO 94/02597, WO 94/18314, WO 97/43424 and SEQ ID NO: 4 of WO 99/019467, such as variants with substitutions in one or more of the following positions: 15, 23, 105, 106, 124, 128, 133, 154, 156, 178, 179, 181, 188, 190, 197, 201, 202, 207, 208, 209, 211, 243, 264, 304, 305, 391, 408, and 444.

Different suitable amylases include amylases having SEQ ID NO: 6 in WO 02/010355 or variants thereof having 90% sequence identity to SEQ ID NO: 6. Preferred variants of SEQ ID NO: 6 are those having a deletion in positions 181 and 182 and a substitution in position 193.

Other amylases which are suitable are hybrid alpha-amylase comprising residues 1-33 of the alpha-amylase derived from *B. amyloliquefaciens* shown in SEQ ID NO: 6 of WO 2006/066594 and residues 36-483 of the *B. licheniformis* alpha-amylase shown in SEQ ID NO: 4 of WO 2006/066594 or variants having 90% sequence identity thereof. Preferred variants of this hybrid alpha-amylase are those having a substitution, a deletion or an insertion in one of more of the following positions: G48, T49, G107, H156, A181, N190, M197,1201, A209 and Q264. Most preferred variants of the hybrid alpha-amylase comprising residues 1-33 of the alpha-amylase derived from *B. amyloliquefaciens* shown in SEQ ID NO: 6 of WO 2006/066594 and residues 36-483 of SEQ ID NO: 4 are those having the substitutions:

M197T;

H156Y+A181T+N190F+A209V+Q264S; or

G48A+T491+G107A+H156Y+A181T+N190F+1201F+A209V+Q264S.

Further amylases which are suitable are amylases having SEQ ID NO: 6 in WO 99/019467 or variants thereof having 90% sequence identity to SEQ ID NO: 6. Preferred variants of SEQ ID NO: 6 are those having a substitution, a deletion or an insertion in one or more of the following positions: R181, G182, H183, G184, N195, 1206, E212, E216 and K269. Particularly preferred amylases are those having deletion in positions R181 and G182, or positions H183 and G184.

Additional amylases which can be used are those having SEQ ID NO: 1, SEQ ID NO: 3, SEQ ID NO: 2 or SEQ ID NO: 7 of WO 96/023873 or variants thereof having 90% sequence identity to SEQ ID NO: 1, SEQ ID NO: 2, SEQ ID NO: 3 or SEQ ID NO: 7. Preferred variants of SEQ ID NO: 1, SEQ ID NO: 2, SEQ ID NO: 3 or SEQ ID NO: 7 are those having a substitution, a deletion or an insertion in one or more of the following positions: 140, 181, 182, 183, 184, 195, 206, 212, 243, 260, 269, 304 and 476, using SEQ ID 2 of WO 96/023873 for numbering. More preferred variants are those having a deletion in two positions selected from 181, 182, 183 and 184, such as 181 and 182, 182 and 183, or positions 183 and 184. Most preferred amylase variants of SEQ ID NO: 1, SEQ ID NO: 2 or SEQ ID NO: 7 are those having a deletion in positions 183 and 184 and a substitution in one or more of positions 140, 195, 206, 243, 260, 304 and 476.

Other amylases which can be used are amylases having SEQ ID NO: 2 of WO 08/153815, SEQ ID NO: 10 in WO 01/66712 or variants thereof having 90% sequence identity to SEQ ID NO: 2 of WO 08/153815 or 90% sequence identity to SEQ ID NO: 10 in WO 01/66712. Preferred variants of SEQ ID NO: 10 in WO 01/66712 are those having a substitution, a deletion or an insertion in one of more of the following positions: 176, 177, 178, 179, 190, 201, 207, 211 and 264.

Further suitable amylases are amylases having SEQ ID NO: 2 of WO 09/061380 or variants having 90% sequence identity to SEQ ID NO: 2 thereof. Preferred variants of SEQ ID NO: 2 are those having a truncation of the C-terminus and/or a substitution, a deletion or an insertion in one of more of the following positions: Q87, Q98, S125, N128, T131, T165, K178, R180, S181, T182, G183, M201, F202, N225, S243, N272, N282, Y305, R309, D319, Q320, Q359, K444 and G475. More preferred variants of SEQ ID NO: 2 are those having the substitution in one of more of the following positions: Q87E, R, Q98R, S125A, N128C, T131I, T165I, K178L, T182G, M201L, F202Y, N225E, R, N272E, R, S243Q, A, E, D, Y305R, R309A, Q320R, Q359E, K444E and G475K and/or deletion in position R180 and/or S181 or of T182 and/or G183. Most preferred amylase variants of SEQ ID NO: 2 are those having the substitutions:

N128C+K178L+T182G+Y305R+G475K;

N128C+K178L+T182G+F202Y+Y305R+D319T+G475K;

S125A+N128C+K178L+T182G+Y305R+G475K; or

S125A+N128C+T1311+T1651+K178L+T182G+Y305R+G475K wherein the variants are C-terminally truncated and optionally further comprises a substitution at position 243 and/or a deletion at position 180 and/or position 181.

Further suitable amylases are amylases having SEQ ID NO: 1 of WO13184577 or variants having 90% sequence identity to SEQ ID NO: 1 thereof. Preferred variants of SEQ ID NO: 1 are those having a substitution, a deletion or an insertion in one of more of the following positions: K176, R178, G179, T180, G181, E187, N192, M199,1203, S241, R458, T459, D460, G476 and G477. More preferred variants of SEQ ID NO: 1 are those having the substitution in one of more of the following positions: K176L, E187P, N192FYH, M199L, 1203YF, S241QADN, R458N, T459S, D460T, G476K and G477K and/or deletion in position R178 and/or S179 or of T180 and/or G181. Most preferred amylase variants of SEQ ID NO: 1 are those having the substitutions:

E187P+1203Y+G476K

E187P+1203Y+R458N+T459S+D460T+G476K, wherein the variants optionally further comprises a substitution at position 241 and/or a deletion at position 178 and/or position 179.

Further suitable amylases are amylases having SEQ ID NO: 1 of WO10104675 or variants having 90% sequence identity to SEQ ID NO: 1 thereof. Preferred variants of SEQ ID NO: 1 are those having a substitution, a deletion or an insertion in one of more of the following positions: N21, D97, V128 K177, R179, S180, I181, G182, M200, L204, E242, G477 and G478. More preferred variants of SEQ ID NO: 1 are those having the substitution in one of more of the following positions: N21D, D97N, V1281 K177L, M200L, L204YF, E242QA, G477K and G478K and/or deletion in position R179 and/or S180 or of I181 and/or G182. Most preferred amylase variants of SEQ ID NO: 1 are those having the substitutions:

N21D+D97N+V128I, wherein the variants optionally further comprises a substitution at position 200 and/or a deletion at position 180 and/or position 181.

Other suitable amylases are the alpha-amylase having SEQ ID NO: 12 in WO01/66712 or a variant having at least 90% sequence identity to SEQ ID NO: 12. Preferred amylase variants are those having a substitution, a deletion or an insertion in one of more of the following positions of SEQ ID NO: 12 in WO01/66712: R28, R118, N174; R181, G182, D183, G184, G186, W189, N195, M202, Y298, N299, K302, S303, N306, R310, N314; R320, H324, E345, Y396, R400, W439, R444, N445, K446, Q449, R458, N471, N484. Particular preferred amylases include variants having a deletion of D183 and G184 and having the substitutions R118K, N195F, R320K and R458K, and a variant additionally having substitutions in one or more position selected from the group: M9, G149, G182, G186, M202, T257, Y295, N299, M323, E345 and A339, most preferred a variant that additionally has substitutions in all these positions.

Other examples are amylase variants such as those described in WO2011/098531, WO2013/001078 and WO2013/001087.

Commercially available amylases are Duramyl™, Termamyl™, Fungamyl™, Stainzyme™, Stainzyme Plus™, Natalase™, Liquozyme X and BAN™ (from Novozymes A/S), and Rapidase™, Purastar™/Effectenz™, Powerase, Preferenz S1000, Preferenz S100 and Preferenz S110 (from Genencor International Inc./DuPont).

Peroxidases/Oxidases:

Suitable peroxidases/oxidases include those of plant, bacterial or fungal origin. Chemically modified or protein engineered variants are included. Examples of useful peroxidases include peroxidases from *Coprinus*, e.g., from *C. cinereus*, and variants thereof as those described in WO 93/24618, WO 95/10602, and WO 98/15257.

Commercially available peroxidases include Guardzyme™ (Novozymes A/S).

Other Enzymes:

A protease variant according to the invention may also be combined with additional enzymes such as pectate lyases e.g. Pectawash™, chlorophyllases etc. The protease variant of the invention may be mixed with any additional enzyme.

The detergent enzyme(s) may be included in a detergent composition by adding separate additives containing one or more enzymes, or by adding a combined additive comprising all of these enzymes. A detergent additive, i.e., a separate additive or a combined additive, can be formulated, for example, as a granulate, liquid, slurry, etc. Preferred detergent additive formulations are granulates, in particular non-dusting granulates, liquids, in particular stabilized liquids, or slurries.

Non-dusting granulates may be produced, e.g., as disclosed in U.S. Pat. Nos. 4,106,991 and 4,661,452 and may optionally be coated by methods known in the art. Examples of waxy coating materials are poly(ethylene oxide) products (polyethyleneglycol, PEG) with mean molar weights of 1000 to 20000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in GB 1483591. Liquid enzyme preparations may, for instance, be stabilized by adding a polyol such as propylene glycol, a sugar or sugar alcohol, lactic acid or boric acid according to established methods. Protected enzymes may be prepared according to the method disclosed in EP 238,216.

Adjunct Materials

Any detergent components known in the art for use in laundry detergents may also be utilized. Other optional detergent components include anti-corrosion agents, anti-shrink agents, anti-soil redeposition agents, anti-wrinkling agents, bactericides, binders, corrosion inhibitors, disintegrants/disintegration agents, dyes, enzyme stabilizers (including boric acid, borates, CMC, and/or polyols such as propylene glycol), fabric conditioners including clays, fillers/processing aids, fluorescent whitening agents/optical brighteners, foam boosters, foam (suds) regulators, perfumes, soil-suspending agents, softeners, suds suppressors, tarnish inhibitors, and wicking agents, either alone or in combination. Any ingredient known in the art for use in laundry detergents may be utilized. The choice of such ingredients is well within the skill of the artisan.

Dispersants The detergent compositions can also contain dispersants. In particular powdered detergents may comprise dispersants. Suitable water-soluble organic materials include the homo- or co-polymeric acids or their salts, in which the polycarboxylic acid comprises at least two carboxyl radicals separated from each other by not more than two carbon atoms. Suitable dispersants are for example described in Powdered Detergents, Surfactant science series volume 71, Marcel Dekker, Inc.

Dye Transfer Inhibiting Agents—The detergent compositions may also include one or more dye transfer inhibiting agents. Suitable polymeric dye transfer inhibiting agents include, but are not limited to, polyvinylpyrrolidone polymers, polyamine N-oxide polymers, copolymers of N-vinylpyrrolidone and N-vinylimidazole, polyvinyloxazolidones and polyvinylimidazoles or mixtures thereof. When present in a subject composition, the dye transfer inhibiting agents may be present at levels from about 0.0001% to about 10%, from about 0.01% to about 5% or even from about 0.1% to about 3% by weight of the composition.

Fluorescent whitening agent—A detergent compositions will preferably also contain additional components that may tint articles being cleaned, such as fluorescent whitening agent or optical brighteners. Where present the brightener is preferably at a level of about 0,01% to about 0,5%. Any fluorescent whitening agent suitable for use in a laundry detergent composition may be used in the composition. The most commonly used fluorescent whitening agents are those belonging to the classes of diaminostilbene-sulphonic acid derivatives, diarylpyrazoline derivatives and bisphenyl-distyryl derivatives. Examples of the diaminostilbene-sulphonic acid derivative type of fluorescent whitening agents include the sodium salts of: 4,4'-bis-(2-diethanolamino-4-anilino-s-triazin-6-ylamino) stilbene-2,2'-disulphonate; 4,4'-bis-(2,4-dianilino-s-triazin-6-ylamino) stilbene-2.2'-disulphonate; 4,4'-bis-(2-anilino-4(N-methyl-N-2-hydroxy-ethylamino)-s-triazin-6-ylamino) stilbene-2,2'-disulphonate, 4,4'-bis-(4-phenyl-2,1,3-triazol-2-yl)stilbene-2,2'-disulphonate; 4,4'-bis-(2-anilino-4(1-methyl-2-hydroxy-ethylamino)-s-triazin-6-ylamino) stilbene-2,2'-disulphonate and 2-(stilbyl-4"-napto-1.,2':4,5)-1,2,3-trizole-2"-sulphonate. Preferred fluorescent whitening agents are Tinopal DMS and Tinopal CBS available from Ciba-Geigy AG, Basel, Switzerland. Tinopal DMS is the disodium salt of 4,4'-bis-(2-morpholino-4 anilino-s-triazin-6-ylamino) stilbene disulphonate. Tinopal CBS is the disodium salt of 2,2'-bis-(phenyl-styryl) disulphonate. Also preferred are fluorescent whitening agents is the commercially available Parawhite KX, supplied by Paramount Minerals and Chemicals, Mumbai, India. Other fluorescers suitable for use include the 1-3-diaryl pyrazolines and the 7-alkylaminocoumarins.

Suitable fluorescent brightener levels include lower levels of from about 0.01, from 0.05, from about 0.1 or even from about 0.2 wt % to upper levels of 0.5 or even 0.75 wt %.

Soil release polymers—The detergent composition may also include one or more soil release polymers which aid the removal of soils from fabrics such as cotton and polyester based fabrics, in particular the removal of hydrophobic soils from polyester based fabrics. The soil release polymers may for example be nonionic or anionic terephthalte based polymers, polyvinyl caprolactam and related copolymers, vinyl graft copolymers, polyester polyamides see for example Chapter 7 in Powdered Detergents, Surfactant science series volume 71, Marcel Dekker, Inc. Another type of soil release polymers are amphiphilic alkoxylated grease cleaning polymers comprising a core structure and a plurality of alkoxylate groups attached to that core structure. The core structure may comprise a polyalkylenimine structure or a polyalkanolamine structure as described in detail in WO 2009/087523 (hereby incorporated by reference). Furthermore random graft co-polymers are suitable soil release polymers Suitable graft co-polymers are described in more detail in WO 2007/138054, WO 2006/108856 and WO 2006/113314 (hereby incorporated by reference). Other soil release polymers are substituted polysaccharide structures especially substituted cellulosic structures such as modified cellulose deriviatives such as those described in EP 1867808 or WO 2003/040279 (both are hereby incorporated by reference). Suitable cellulosic polymers include cellulose, cellulose ethers, cellulose esters, cellulose amides and mixtures thereof. Suitable cellulosic polymers include anionically modified cellulose, nonionically modified cellulose, cationically modified cellulose, zwitterionically modified cellulose, and mixtures thereof. Suitable cellulosic polymers include methyl cellulose, carboxy methyl cellulose, ethyl cellulose, hydroxyl ethyl cellulose, hydroxyl propyl methyl cellulose, ester carboxy methyl cellulose, and mixtures thereof.

Anti-redeposition agents—The detergent compositions may also include one or more anti-redeposition agents such as carboxymethylcellulose (CMC), polyvinyl alcohol (PVA), polyvinylpyrrolidone (PVP), polyoxyethylene and/or polyethyleneglycol (PEG), homopolymers of acrylic acid, copolymers of acrylic acid and maleic acid, and ethoxylated polyethyleneimines. The cellulose based polymers described under soil release polymers above may also function as anti-redeposition agents.

Other suitable adjunct materials include, but are not limited to, anti-shrink agents, anti-wrinkling agents, bactericides, binders, carriers, dyes, enzyme stabilizers, fabric softeners, fillers, foam regulators, hydrotropes, perfumes, pigments, sod suppressors, solvents, structurants for liquid detergents and/or structure elasticizing agents.

Formulation of Detergent Products

The detergent composition may be in any convenient form, e.g., a bar, a homogenous tablet, a tablet having two or more layers, a regular or compact powder, a granule, a paste, a gel, or a regular, compact or concentrated liquid.

Detergent formulation forms: Layers (same or different phases), Pouches, versus forms for Machine dosing unit.

Pouches can be configured as single or multi compartments. It can be of any form, shape and material which is suitable for hold the composition, e.g. without allowing the release of the composition to release of the composition from the pouch prior to water contact. The pouch is made from water soluble film which encloses an inner volume. Said inner volume can be divided into compartments of the pouch. Preferred films are polymeric materials preferably polymers which are formed into a film or sheet. Preferred polymers, copolymers or derivates thereof are selected polyacrylates, and water soluble acrylate copolymers, methyl cellulose, carboxy methyl cellulose, sodium dextrin, ethyl cellulose, hydroxyethyl cellulose, hydroxypropyl methyl cellulose, malto dextrin, poly methacrylates, most preferably polyvinyl alcohol copolymers and, hydroxyprpyl methyl cellulose (HPMC). Preferably the level of polymer in the film for example PVA is at least about 60%. Preferred average molecular weight will typically be about 20,000 to about 150,000. Films can also be of blend compositions comprising hydrolytically degradable and water soluble polymer blends such as polyactide and polyvinyl alcohol (known under the Trade reference M8630 as sold by Chris Craft In. Prod. Of Gary, Ind., US) plus plasticisers like glycerol, ethylene glycerol, Propylene glycol, sorbitol and mixtures thereof. The pouches can comprise a solid laundry cleaning composition or part components and/or a liquid cleaning composition or part components separated by the water soluble film. The compartment for liquid components can be different in composition than compartments containing solids. Ref: (US2009/0011970 A1)

Detergent ingredients can be separated physically from each other by compartments in water dissolvable pouches or in different layers of tablets. Thereby negative storage interaction between components can be avoided. Different dissolution profiles of each of the compartments can also give rise to delayed dissolution of selected components in the wash solution.

Definition/Characteristics of the Forms:

A liquid or gel detergent, which is not unit dosed, may be aqueous, typically containing at least 20% by weight and up to 95% water, such as up to about 70% water, up to about 65% water, up to about 55% water, up to about 45% water, up to about 35% water. Other types of liquids, including without limitation, alkanols, amines, diols, ethers and polyols may be included in an aqueous liquid or gel. An aqueous liquid or gel detergent may contain from 0-30% organic solvent.

A liquid or gel detergent may be non-aqueous.

Granular Detergent Formulations

A granular detergent may be formulated as described in WO09/092699, EP1705241, EP1382668, WO07/001262, U.S. Pat. No. 6,472,364, WO04/074419 or WO09/102854. Other useful detergent formulations are described in WO09/124162, WO09/124163, WO09/117340, WO09/117341, WO09/117342, WO09/072069, WO09/063355, WO09/132870, WO09/121757, WO09/112296, WO09/112298, WO09/103822, WO09/087033, WO09/050026, WO09/047125, WO09/047126, WO09/047127, WO09/047128, WO09/021784, WO09/010375, WO09/000605, WO09/122125, WO09/095645, WO09/040544, WO09/040545, WO09/024780, WO09/004295, WO09/004294, WO09/121725, WO09/115391, WO09/115392, WO09/074398, WO09/074403, WO09/068501, WO09/065770, WO09/021813, WO09/030632, and WO09/015951. WO2011025615, WO2011016958, WO2011005803, WO2011005623, WO2011005730, WO2011005844, WO2011005904, WO2011005630, WO2011005830, WO2011005912, WO2011005905, WO2011005910, WO2011005813, WO2010135238, WO2010120863, WO2010108002, WO2010111365, WO2010108000, WO2010107635, WO2010090915, WO2010033976, WO2010033746, WO2010033747, WO2010033897, WO2010033979, WO2010030540, WO2010030541, WO2010030539, WO2010024467, WO2010024469, WO2010024470, WO2010025161, WO2010014395, WO2010044905, WO2010145887, WO2010142503, WO2010122051, WO2010102861, WO2010099997, WO2010084039, WO2010076292, WO2010069742, WO2010069718, WO2010069957,
WO2010057784, WO2010054986, WO2010018043, WO2010003783, WO2010003792, WO2011023716, WO2010142539, WO2010118959, WO2010115813, WO2010105942, WO2010105961, WO2010105962, WO2010094356, WO2010084203, WO2010078979, WO2010072456, WO2010069905, WO2010076165, WO2010072603, WO2010066486, WO2010066631, WO2010066632, WO2010063689, WO2010060821, WO2010049187, WO2010031607, WO2010000636, Methods and Uses The protease variants of the present invention may be added to and thus become a component of a detergent composition, wherein said variant comprises one or more of the following alterations: A1L, A1*, V2I, P3*, S4*, S4C, Q6C, Q18A, L43I, E50Q, N59L, L61K, V62G, G64A, G64S, S65F, Q70T, Q70L, Q70N Q70Y, Q70F, Q70M, Q70A, Q70V, Q97K, G107N, *108aA, N109T, *109aA, N109A, S111I, S111R, Y113S, S114V, S114A, S114F, D126G, D126K, E127R, E127Q, S133H, I137N, M139L, S143R, S144P, S144R, A145E, L149R, L149T, I150L, I150T, I150S, I150V, V162S, V162E, V162Q, V162G, V162F, V162T, V162Y, I164M, S171D, G182A, G182S, Q198E, Q198D, G200C, G200S, A233S, T246M, A267S, S274V, Q275Y, and L276I of SEQ ID NO: 3 and wherein the variant has at least 60%, such as at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% sequence identity to SEQ ID NO: 3. Detergent compositions is generally used in cleaning processes such as laundry and/or hard surface cleaning e.g. dish wash.

One embodiment of the invention relates to a detergent composition, such as a laundry or dish wash compositions comprising a protease variant of a protease parent having at least 60% identity to SEQ ID NO 3 wherein said variant comprises at least one alteration selected from the group consisting of A1L, A1*, V2I, P3*, S4*, S4C, Q6C, Q18A, L43I, E50Q, N59L, L61K, V62G, G64A, G64S, S65F, Q70T, Q70L, Q70N Q70Y, Q70F, Q70M, Q70A, Q70V, Q97K, G107N, *108aA, N109T, *109aA, N109A, S111I, S111R, Y113S, S114V, S114A, S114F, D126G, D126K, E127R, E127Q, S133H, I137N, M139L, S143R, S144P, S144R, A145E, L149R, L149T, I150L, I150T, I150S, I150V, V162S, V162E, V162Q, V162G, V162F, V162T, V162Y, I164M, S171D, G182A, G182S, Q198E, Q198D, G200C, G200S, A233S, T246M, A267S, S274V, Q275Y, L276I and T297P.

A detergent composition may comprise at least one a protease variant wherein said variant comprises one or more of the following substitutions A1L, A1*, V2I, P3*, 84*, S4C, Q6C, Q18A, L43I, E50Q, N59L, L61K, V62G, G64A, G64S, S65F, Q70T, Q70L, Q70N Q70Y, Q70F, Q70M, Q70A, Q70V, Q97K, G107N, *108aA, N109T, *109aA, N109A, S111I, S111R, Y113S, S114V, S114A, S114F, D126G, D126K, E127R, E127Q, S133H, I137N, M139L, S143R, S144P, S144R, A145E, L149R, L149T, I150L, I150T, I150S, I150V, V162S, V162E, V162Q, V162G, V162F, V162T, V162Y, I164M, S171D, G182A, G182S, Q198E, Q198D, G200C, G200S, A233S, T246M, A267S, S274V, Q275Y, and L276I of SEQ ID NO: 3, wherein the protease variant has a sequence identity to SEQ ID NO: 3 of at least 60% such as at least at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% sequence identity to SEQ ID NO: 3 and the variant has protease activity. The at least one protease variant has improved detergent stability compared to the parent protease when measured as described under "Material and Methods".

A detergent composition may be formulated, for example, as a hand or machine laundry detergent composition including a laundry additive composition suitable for pre-treatment of stained fabrics and a rinse added fabric softener composition, or be formulated as a detergent composition for use in general household hard surface cleaning operations, or be formulated for hand or machine dishwashing operations.

A cleaning process or the textile care process may for example be a laundry process, a dishwashing process or cleaning of hard surfaces such as bathroom tiles, floors, table tops, drains, sinks and washbasins. Laundry processes can for example be household laundering, but it may also be industrial laundering. A process for laundering of fabrics and/or garments may be a process comprises treating fabrics with a washing solution containing a detergent composition, and at least one protease variant. A cleaning process or a textile care process can for example be carried out in a machine washing process or in a manual washing process. The washing solution can for example be an aqueous washing solution containing a detergent composition.

The fabrics and/or garments subjected to a washing, cleaning or textile care process may be conventional washable laundry, for example household laundry. Preferably, the major part of the laundry is garments and fabrics, including knits, woven, denims, non-woven, felts, yarns, and towelling. The fabrics may be cellulose based such as natural cellulosics, including cotton, flax, linen, jute, ramie, sisal or coir or manmade cellulosics (e.g., originating from wood pulp) including viscose/rayon, ramie, cellulose acetate fibers (tricell), lyocell or blends thereof. The fabrics may also be non-cellulose based such as natural polyamides including wool, camel, cashmere, mohair, rabit and silk or synthetic polymer such as nylon, aramid, polyester, acrylic, polypropylen and spandex/elastane, or blends thereof as well as blend of cellulose based and non-cellulose based fibers. Examples of blends are blends of cotton and/or rayon/viscose with one or more companion material such as wool, synthetic fibers (e.g., polyamide fibers, acrylic fibers, polyester fibers, polyvinyl alcohol fibers, polyvinyl chloride fibers, polyurethane fibers, polyurea fibers, aramid fibers), and cellulose-containing fibers (e.g., rayon/viscose, ramie, flax, linen, jute, cellulose acetate fibers, lyocell).

The last few years there has been an increasing interest in replacing components in detergents, which is derived from petrochemicals with renewable biological components such as enzymes and polypeptides without compromising the wash performance. When the components of detergent compositions change new enzyme activities or new enzymes having alternative and/or improved properties compared to the common used detergent enzymes such as proteases, lipases and amylases is needed to achieve a similar or improved wash performance when compared to the traditional detergent compositions.

Proteases and variants hereof are usable in proteinaceous stain removing processes. The proteinaceous stains may be stains such as food stains, e.g., baby food, sebum, cocoa, egg, blood, milk, ink, grass, or a combination hereof.

Typical detergent compositions include various components in addition to the enzymes, these components have different effects, some components like the surfactants lower the surface tension in the detergent, which allows the stain being cleaned to be lifted and dispersed and then washed away, other components like bleach systems remove discolor often by oxidation and many bleaches also have strong bactericidal properties, and are used for disinfecting and sterilizing. Yet other components like builder and chelator softens, e.g., the wash water by removing the metal ions form the liquid.

The enzyme compositions may further comprise at least one or more of the following: a surfactant, a builder, a chelator or chelating agent, bleach system or bleach component in laundry or dish wash.

The amount of a surfactant, a builder, a chelator or chelating agent, bleach system and/or bleach component may be reduced compared to amount of surfactant, builder, chelator or chelating agent, bleach system and/or bleach component used without the added protease variant of the invention. Preferably the at least one component which is a surfactant, a builder, a chelator or chelating agent, bleach system and/or bleach component is present in an amount that is 1% less, such as 2% less, such as 3% less, such as 4% less, such as 5% less, such as 6% less, such as 7% less, such as 8% less, such as 9% less, such as 10% less, such as 15% less, such as 20% less, such as 25% less, such as 30% less, such as 35% less, such as 40% less, such as 45% less, such as 50% less than the amount of the component in the system without the addition of protease variants of the invention, such as a conventional amount of such component. Detergent compositions may also be composition which is free of at least one component which is a surfactant, a builder, a chelator or chelating agent, bleach system or bleach component and/or polymer.

Washing Methods

Detergent compositions are ideally suited for use in laundry applications. These methods include a method for laundering a fabric. The method comprises the steps of contacting a fabric to be laundered with a cleaning laundry solution comprising a detergent composition. The fabric may comprise any fabric capable of being laundered in normal consumer use conditions. The solution preferably has a pH from about 5.5 to about 11.5. The compositions may be employed at concentrations from about 100 ppm, preferably 500 ppm to about 15,000 ppm in solution. The water temperatures typically range from about 5° C. to about 95° C., including about 10° C., about 15° C., about 20° C., about 25° C., about 30° C., about 35° C., about 40° C., about 45° C., about 50° C., about 55° C., about 60° C., about 65° C., about 70° C., about 75° C., about 80° C., about 85° C. and about 90° C. The water to fabric ratio is typically from about 1:1 to about 30:1.

In particular embodiments, the washing method is conducted at a pH from about 5.0 to about 11.5, or from about 6 to about 10.5, about 5 to about 11, about 5 to about 10, about 5 to about 9, about 5 to about 8, about 5 to about 7, about 5.5 to about 11, about 5.5 to about 10, about 5.5 to about 9, about 5.5 to about 8, about 5.5. to about 7, about 6 to about 11, about 6 to about 10, about 6 to about 9, about 6 to about 8, about 6 to about 7, about 6.5 to about 11, about 6.5 to about 10, about 6.5 to about 9, about 6.5 to about 8, about 6.5 to about 7, about 7 to about 11, about 7 to about 10, about 7 to about 9, or about 7 to about 8, about 8 to about 11, about 8 to about 10, about 8 to about 9, about 9 to about 11, about 9 to about 10, about 10 to about 11, preferably about 5.5 to about 11.5.

In particular embodiments, the washing method is conducted at a degree of hardness of from about 0° dH to about 30° dH, such as about 1° dH, about 2° dH, about 3° dH, about 4° dH, about 5° dH, about 6° dH, about 7° dH, about 8° dH, about 9° dH, about 10° dH, about 11° dH, about 12° dH, about 13° dH, about 14° dH, about 15° dH, about 16° dH, about 17° dH, about 18° dH, about 19° dH, about 20° dH, about 21° dH, about 22° dH, about 23° dH, about 24° dH, about 25° dH, about 26° dH, about 27° dH, about 28° dH, about 29° dH, about 30° dH. Under typical European wash conditions, the degree of hardness is about 16° dH, under typical US wash conditions about 6° dH, and under typical Asian wash conditions, about 3° dH.

The compositions for use in the methods described above may further comprises at least one additional enzyme as set forth in the "other enzymes" section above, such as an enzyme selected from the group of hydrolases such as proteases, lipases and cutinases, carbohydrases such as amylases, cellulases, hemicellulases, xylanases, and pectinase or a combination hereof.

The present invention is further described by the following examples that should not be construed as limiting the scope of the invention.

EXAMPLES

Example 1: Construction of TY145 Variants by Site-Directed Mutagenesis

Site-directed variants were constructed of the TY145 protease (SEQ ID NO: 3) comprising specific substitutions according to the invention. The variants were made by traditional cloning of DNA fragments (Sambrook et al., Molecular Cloning: A Laboratory Manual, 2nd Ed., Cold Spring Harbor, 1989) using PCR together with properly designed mutagenic oligonucleotides that introduced the desired mutations in the resulting sequence.

Mutagenic oligos were designed corresponding to the DNA sequence flanking the desired site(s) of mutation, separated by the DNA base pairs defining the insertions/deletions/substitutions, and purchased from an oligo vendor such as Life Technologies. In this manner, the variants listed in Table 1a and 1b below were constructed and produced.

In order to test TY145 protease variants of the invention, the mutated DNA comprising a variant of the invention were transformed into a competent B. subtilis strain and fermented using standard protocols (liquid media, 3-4 days, 30° C.). The culture broth was centrifuged (26000×g, 20 min) and the supernatant was carefully decanted from the precipitate. The supernatant was filtered through a Nalgene 0.2 µm filtration unit in order to remove the rest of the Bacillus host cells. The 0.2 µm filtrate was mixed 1:1 with 3.0M (NH4)2SO4 and the mixture was applied to a Phenylsepharose FF (high sub) column (from GE Healthcare) equilibrated in 100 mM H3BO3, 10 mM MES/NaOH, 2 mM CaCl2), 1.5M (NH4)2SO4, pH 6.0. After washing the column with the equilibration buffer, the protease was step-eluted with 100 mM H3BO3, 10 mM MES, 2 mM CaCl2), pH 6.0. The eluted peak (containing the protease activity) was collected and applied to a Bacitracin agarose column (from Upfront chromatography) equilibrated in 100 mM H3BO3, 10 mM MES, 2 mM CaCl2), pH 6.0. After washing the column extensively with the equilibration buffer, the protease was eluted with 100 mM H3BO3, 10 mM MES, 2 mM CaCl2), 1M NaCl, pH 6.0 with 25% (v/v) 2-propanol. The elution peak (containing the protease activity) was transferred to 20 mM MES, 2 mM CaCl2), pH 6.0 on a G25 sephadex column (from GE Healthcare). The G25 transferred peak was the purified preparation and was used for further experiments.

TABLE 1a

| Variants of SEQ ID NO 3 |
| --- |
| A1L, S173P, S175P, F180Y |
| A1*, S27K, S173P, S175P, F180Y, Q198E, T297P |
| V2I, S173P, S175P, F180Y |
| A1*, P3*, Q6C, S27K, S171N, S173P, G174R, S175P, F180Y, Q198E, T297P |
| A1*, P3*, S4C, S27K, S171N, S173P, G174R, S175P, F180Y, Q198E, T297P |
| A1*, P3*, S4C, S27K, S171N, S173P, G174R, S175P, F180Y, Q198E, E236C, T297P |
| A1*, V2*, P3*, S4*, S27K, S173P, S175P, F180Y, Q198E, T297P |
| S4C, S27K, S171N, S173P, G174R, S175P, F180Y, Q198E, E236C, T297P |
| Q6C, S27K, S171N, S173P, G174R, S175P, F180Y, Q198E, E236C, T297P |
| Q18A, S173P, S175P, F180Y |
| L43I, G47K, R130K, G132R, S173P, S175P |
| S27K, N59L, T67V, Q70N, S171N, S173P, G174R, S175P, F180Y, Q198E, N199K, T297P |
| L61K, S173P, S175P |
| V62G, R69D, S173P, S175P |
| G64A, R69D, S173P, S175P |
| G64S, R69D, S173P, S175P |
| S65F, S173P, S175P, F180Y |
| Q70T, L149T, I150L, S173P, S175P |
| Q70T, I121L, S173P, S175P |
| Q70L, S173P, S175P, F180Y |
| Q70Y, S173P, S175P, F180Y |
| S27K, Q70Y, E127Q, S173P, S175P, F180Y, Q198E, T297P |
| Q70F, S173P, S175P, F180Y |
| S27K, Q70F, E127Q, S173P, S175P, F180Y, Q198E, T297P |
| S27K, Q70F, G107N, I121V, E127Q, S173P, S175P, F180Y, Q198E, T297P |
| Q70M, S173P, S175P, F180Y |
| Q70A, S173P, S175P, F180Y |
| S27K, Q70A, S171N, S173P, G174R, S175P, F180Y, Q198E, N199K, T297P |
| S27K, Q70A, S114V, E127Q, I150L, S173P, S175P, F180Y, Q198E, T297P |
| S27K, Q70A, G107N, I121V, E127Q, S173P, S175P, F180Y, Q198E, T297P |
| S27K, Q70A, I121V, S171N, S173P, G174R, S175P, F180Y, Q198E, T297P |
| S27K, Q70A, G107N, I121V, E127Q, S173P, S175P, F180Y, Q198E, T297P |
| S27K, Q70A, S114V, S173P, G174K, S175P, F180Y, Q198E, N199K, T297P |
| S27K, Q70V, S171N, S173P, G174R, S175P, F180Y, Q198E, N199K, T297P |
| S27K, Q70V, S114V, E127Q, I150L, S173P, S175P, F180Y, Q198E, T297P |
| S27K, Q70V, G107N, I121V, E127Q, S173P, S175P, F180Y, Q198E, T297P |
| S27K, Q70V, S171N, S173P, G174R, S175P, F180Y, Q198E, T297P |
| G107N, S173P, S175P, F180Y, Q198E, T297P |
| Q70N, G107N, I137Q, S173P, S175P, F180Y, T297P |
| Q70N, G107N, I137N, S173P, S175P, F180Y, T297P |
| S27K, G107N, E127Q, S173P, S175P, F180Y, Q198E, T297P |
| S27K, N59L, T67V, N87K, G107N, I121V, S171N, S173P, G174R, S175P, F180Y, Q198E, T297P |
| S27K, Y39R, G107N, I137E, S173P, S175P, F180Y, T297P |
| S27K, Q70N, N87K, G107N, I121V, E127Q, S171N, S173P, G174R, S175P, F180Y, Q198E, T297P |
| S27K, *108aA, N109S, S111R, S173P, S175P, F180Y, Q198E, T297P |
| S27K, N109T, S173P, S175P, F180Y, Q198E, T297P |
| S27K, N109S, *109aA, S111R, S173P, S175P, F180Y, Q198E, T297P |
| S27K, N109A, S173P, S175P, F180Y, Q198E, T297P |
| S27K, N109A, S173P, G174K, S175P, F180Y, Q197K, Q198E, T297P |
| S111I, S173P, S175P, F180Y |
| Q70N, Y113S, S173P, S175P |
| Y113S, A145S, S173P, S175P |
| S114V, A145S, S173P, S175P |
| S114V, K146P, S173P, S175P |
| S114V, M139L, S173P, S175P |
| S27K, S114V, E127Q, I150L, S173P, S175P, F180Y, Q198E, T297P |
| S27K, S114V, S171N, S173P, G174R, S175P, F180Y, Q198E, N199K, T297P |
| S27K, S114V, S171N, S173P, G174R, S175P, F180Y, Q198E, N199R, T297P |
| S27K, S114V, I150L, S171N, S173P, G174R, S175P, F180Y, Q198E, N199K, T297P |
| S27K, Q70A, S114V, S173P, G174K, S175P, F180Y, Q198E, N199K, T297P |
| S114A, S173P, S175P, F180Y |
| S27K, Q70N, S114A, S171N, S173P, G174R, S175P, F180Y, Q198E, N199K, T297P |
| S114F, S173P, S175P, F180Y |
| S27K, S114F, E127Q, S173P, S175P, F180Y, Q198E, T297P |
| S27K, S133H, S173P, S175P, F180Y, T297P |
| I137N, S173P, S175P, F180Y, Q198E, T297P |
| S27K, Q97K, I137N, S173P, S175P, F180Y, Q198E, T297P |
| S27K, Q97K, I137N, S173P, S175P, F180Y, T297P |
| S27K, I137N, S173P, S175P, F180Y, S270K, T297P |
| S27K, S111R, I137N, S173P, S175P, F180Y, T297P |

TABLE 1a-continued

Variants of SEQ ID NO 3

S27K, E127Q, I137N, S173P, S175P, F180Y, Q198E, T297P
Q70N, G107N, I137N, S173P, S175P, F180Y, T297P
S27K, I137N, S171N, S173P, G174R, S175P, F180Y, Q198E, T297P
S27K, N109S, S111R, I137N, S173P, S175P, F180Y, Q198E, T297P
S114V, M139L, S173P, S175P
S27K, S143R, S173P, S175P, F180Y, T297P
S144P, S173P, S175P
S144P, A145S, K146P, S148A, L149T, I150L, S173P, S175P
I137E, S144P, S173P, S175P, F180Y, T297P
S27K, S144P, D147N, S173P, S175P, F180Y, Q198E, T297P
Q70N, I137Q, S144P, S173P, S175P, F180Y, T297P
Q70N, I137N, S144P, S173P, S175P, F180Y, T297P
S27K, E127Q, S144P, S173P, S175P, F180Y, Q198E, T297P
S27K, Q70N, E127Q, S144P, S173P, S175P, F180Y, Q198E, T297P
S27K, S144P, S171N, S173P, G174R, S175P, F180Y, Q198E, N199K, T297P
S27K, S144P, K146T, A151R, S171N, S173P, G174R, S175P, F180Y, Q198E, N199K, T297P
S27K, S144P, K146P, A151R, S171N, S173P, G174R, S175P, F180Y, Q198E, N199K, T297P
S27K, S144P, K146T, I150L, A151R, S171N, S173P, G174R, S175P, F180Y, Q198E, N199K, T297P
S27K, S144P, K146P, I150L, A151R, S171N, S173P, G174R, S175P, F180Y, Q198E, N199K, T297P
A145S, K146P, D147S, S148A, L149T, S173P, S175P
I137A, L149T, I150L, S173P, S175P
K146P, L149T, S173P, S175P
D116S, L149T, S173P, S175P
S27K, S114V, E127Q, I150L, S173P, S175P, F180Y, Q198E, T297P
S27K, Q70N, E127Q, I150L, S173P, S175P, F180Y, Q198E, T297P
S27K, I150L, S171N, S173P, G174R, S175P, F180Y, Q198E, N199K, T297P
S27K, I150L, S171N, S173P, G174R, S175P, F180Y, Q198E, N199R, T297P
S27K, K146T, I150L, A151R, S171N, S173P, G174R, S175P, F180Y, Q198E, N199K, T297P
S27K, K146P, I150L, A151R, S171N, S173P, G174R, S175P, F180Y, Q198E, N199K, T297P
S27K, S144R, K146T, I150L, A151R, S171N, S173P, G174R, S175P, F180Y, Q198E, N199K, T297P
I150T, S173P, S175P, F180Y
N16H, S27K, E50H, G132H, I150S, S173P, S175P, F180Y, Q198E, T297P
S27K, I150S, S171N, S173P, G174R, S175P, F180Y, Q198E, N199K, T297P
S27K, I150S, S171N, S173P, G174R, S175P, F180Y, Q198E, N199R, T297P
S27K, K146T, I150S, A151R, S171N, S173P, G174R, S175P, F180Y, Q198E, N199K, T297P
S27K, K146P, I150S, A151R, S171N, S173P, G174R, S175P, F180Y, Q198E, N199K, T297P
S27K, Q70N, I121V, I150S, S171N, S173P, G174R, S175P, F180Y, Q198E, T297P
I150V, S173P, S175P, F180Y
S27K, V162S, S173P, S175P, F180Y, Q198E, T297P
S27K, E127Q, V162S, S173P, S175P, F180Y, Q198E, T297P
N16H, S27K, E50H, G132H, V162S, S173P, S175P, F180Y, Q198E, T297P
S27K, V162E, S173P, S175P, F180Y, Q198E, T297P
S27K, E127Q, V162E, S173P, S175P, F180Y, Q198E, T297P
S27K, V162Q, S173P, S175P, F180Y, Q198E, T297P
S27K, E127Q, V162Q, S173P, S175P, F180Y, Q198E, T297P
S27K, V162G, S173P, S175P, F180Y, Q198E, T297P
S27K, E127Q, V162G, S173P, S175P, F180Y, Q198E, T297P
S27K, V162F, S173P, S175P, F180Y, Q198E, T297P
S27K, E127Q, V162F, S173P, S175P, F180Y, Q198E, T297P
S27K, I121V, V162F, S171N, S173P, G174R, S175P, F180Y, Q198E, T297P
S27K, V162F, S173P, G174K, S175P, F180Y, Q197K, Q198E, T297P
S27K, V162T, S173P, S175P, F180Y, Q198E, T297P
S27K, E127Q, V162T, S173P, S175P, F180Y, Q198E, T297P
S27K, V162T, S173P, G174K, S175P, F180Y, Q198E, N199R, T297P
S27K, V162Y, S173P, S175P, F180Y, Q198E, T297P
S27K, E127Q, V162Y, S173P, S175P, F180Y, Q198E, T297P
S27K, Q70N, G107N, I121V, E127Q, V162Y, S173P, S175P, F180Y, Q198E, T297P
S27K, V162Y, S173P, G174K, S175P, F180Y, Q198E, N199K, T297P
S27K, V162Y, S173P, G174K, S175P, F180Y, Q197K, Q198E, T297P
S27K, V162Y, S171N, S173P, G174R, S175P, F180Y, G182A, L184Y, Q198E, N199K, T297P
S27K, Q70N, G107N, I121V, E127Q, V162Y, S171N, S173P, G174R, S175P, F180Y, Q198E, T297P
I164M, S173P, S175P, F180Y
S27K, S171D, S173P, G174R, S175P, F180Y, Q198E, T297P
S173P, S175P, F180Y, G182A
S27K, K146E, S171N, S173P, G174R, S175P, F180Y, G182A, Q198E, N199K, E223K, T297P
S27K, S114V, I150L, S171N, S173P, G174R, S175P, F180Y, G182A, Q198E, N199K, T297P
S27K, S173P, G174K, S175P, G179S, F180Y, G182A, Q198E, N199K, T297P
S27K, S173P, G174K, S175P, F180Y, G182A, L184F, V185P, Q198E, N199K, T297P
S27K, S173P, G174K, S175P, F180Y, G182A, L184Y, V185P, Q198E, N199K, T297P
S27K, Q70N, G107N, I121V, E127Q, S173P, S175P, F180Y, G182A, Q198E, T297P
S27K, S173P, G174K, S175P, F180Y, G182A, Q198E, N199K, T297P
S27K, S173P, G174K, S175P, F180Y, G182A, Q198E, N199K, T297P
S27K, S173P, G174K, S175P, F180Y, G182A, Q197K, Q198E, T297P
S27K, S173P, G174K, S175P, F180Y, G182A, Q198E, N199R, T297P
I121V, S173P, S175P, F180Y, G182A, T297P
I121V, S173P, S175P, F180Y, G182A, S274V, T297P
S173P, S175P, F180Y, G182S
S173P, S175P, Q198E

TABLE 1a-continued

| Variants of SEQ ID NO 3 |
|---|

S173P, S175P, Q198E
I137E, S173P, S175P, F180Y, Q198E, T297P
V162R, S173P, S175P, F180Y, Q198E, T297P
D155N, S173P, S175P, Q198E
D17N, S173P, S175P, Q198E
D147N, S173P, S175P, Q198E
Y156R, S173P, S175P, Q198E
S27K, S173P, S175P, Q198E
D147Q, S173P, S175P, Q198E
Q97K, S173P, S175P, Q198E
E50Q, S173P, S175P, Q198E
S173P, S175P, F180Y, Q198E, V286Q, T297P
G107N, S173P, S175P, F180Y, Q198E, T297P
Y156R, S173P, S175P, F180Y, Q198E, T297P
S27K, S173P, S175P, F180Y, Q198E, T297P
N87K, S173P, S175P, F180Y, Q198E, T297P
D147Q, S173P, S175P, F180Y, Q198E, T297P
I137N, S173P, S175P, F180Y, Q198E, T297P
I121V, S173P, S175P, F180Y, Q198E, T297P
S27K, S173P, S175P, F180Y, Q198E, I293R, T297P
S27K, S173P, S175P, F180Y, Q198E, S270K, T297P
S27K, S173P, G174R, S175P, F180Y, Q198E, T297P
S27K, D126G, S173P, S175P, F180Y, Q198E, T297P
S27K, Q97K, S173P, S175P, F180Y, Q198E, T297P
S27K, Q97K, I137N, S173P, S175P, F180Y, Q198E, T297P
S27K, S173P, S175P, F180Y, Q197K, Q198E, T297P
S27K, E127Q, I137E, S173P, S175P, F180Y, Q198E, T297P
S27K, N59L, T67V, N87K, I121V, S171N, S173P, G174R, S175P, F180Y, Q198E, T297P
S27K, S173P, S175P, F180Y, Q198D, T297P
S173P, S175P, F180Y, E194I, V196I, Q197R, Q198E, N199I, G200C, T297P
S173P, S175P, F180Y, E194I, V196I, Q197R, Q198E, N199I, G200S, T297P
S27K, S171N, S173P, G174R, S175P, F180Y, Q198E, N199K, A233S, T297P
S173P, S175P, T246M, I247K
Y113T, E127Q, S173P, G174K, S175P, F180Y, A267S
S27K, S173P, S175P, F180Y, Q198E, S274V, T297P
S27K, S173P, G174K, S175P, F180Y, Q198E, N199R, S274V, T297P
I121V, S173P, S175P, F180Y, S274V, T297P
I121V, S173P, S175P, F180Y, G182A, S274V, T297P
I121V, S173P, S175P, F180Y, Q198E, N199R, S274V, T297P
S27K, Q70N, I121V, S171N, S173P, G174R, S175P, F180Y, Q198E, S274V, T297P
S27K, Q70A, S114V, E127Q, I150L, S173P, S175P, F180Y, Q198E, S274V, T297P
S173P, S175P, F180Y, Q275Y
S173P, S175P, F180Y, L276I

TABLE 1b

| Variants of SEQ ID NO 3 |
|---|

S27K, N59L, T67V, I121V, S173P, G174K, S175P, F180Y, G182A, L184Y, Q197K, Q198E, T297P
S27K, I121V, S173P, G174R, S175A, F180Y, G182A, L184Y, Q197K, Q198E, S270V, T297P
S27K, Q70A, I121V, E127Q, S173P, G174K, S175P, F180Y, G182A, L184F, Q197K, Q198E, T297P
S27K, Q70A, S171D, S173P, G174R, S175P, F180Y, G182A, L184F, Q198E, N199K, S274V, T297P
S27K, Q70N, I121V, S173P, G174K, S175P, G182A, L184F, Q198E, T297P
S27K, S171E, S173P, G174K, S175P, F180Y, G182A, L184F, Q198E, N199K, T297P
S27K, S173P, G174K, S175P, F180Y, G182A, L184F, Q198E, V286R, T297P
S27K, V162T, S171D, S173P, G174R, S175A, F180Y, G182A, L184F, Q197K, Q198E, T297P
S27K, S171D, S173P, G174R, S175A, F180Y, G182A, L184F, Q198E, N199K, T297P
S27K, N87K, S171D, S173P, G174R, S175P, G182A, L184F, Q198E, N199R, T297P
S27K, N109R, S111E, S171E, S173P, G174K, S175P, F180Y, G182A, L184F, Q198E, N199K, T297P
S27K, N109K, S111E, S171E, S173P, G174K, S175P, F180Y, G182A, L184F, Q198E, N199K, T297P
S27K, *108aA, N109S, V162T, S173P, G174K, S175A, F180Y, G182A, L184F, Q197K, Q198E, T297P
S27K, N109R, S111E, V162T, S173P, G174K, S175A, F180Y, G182A, L184F, Q197K, Q198E, T297P
S27K, *108aA, N109S, S171D, S173P, G174R, S175A, F180Y, G182A, L184F, Q198E, N199K, T297P
E50Q
Q70N
Q97K
S111R
S114A
D126K

TABLE 1b-continued

Variants of SEQ ID NO 3

D126G
E127Q
E127R
S144P
S144R
A145E
L149R
G182A
S274V

Example 2: Protease Activity Assays

1) Suc-AAPF-pNA Activity Assay:

The proteolytic activity can be determined by a method employing the Suc-AAPF-pNA substrate. Suc-AAPF-pNA is an abbreviation for N-Succinyl-Alanine-Alanine-Proline-Phenylalanine-p-Nitroanilide, and it is a blocked peptide which can be cleaved by endo-proteases. Following cleavage a free pNA molecule is liberated and it has a yellow colour and thus can be measured by visible spectrophotometry at wavelength 405 nm. The Suc-AAPF-PNA substrate is manufactured by Bachem (cat. no. L1400, dissolved in DMSO).

The protease sample to be analyzed was diluted in residual activity buffer (100 mM Tris pH 8.6). The assay was performed by transferring 30 μl of diluted enzyme samples to 96 well microtiter plate and adding 70 μl substrate working solution (0.72 mg/ml in 100 mM Tris pH8.6). The solution was mixed at room temperature and absorption is measured every 20 sec. over 5 minutes at OD 405 nm.

The slope (absorbance per minute) of the time dependent absorption-curve is directly proportional to the activity of the protease in question under the given set of conditions. The protease sample should be diluted to a level where the slope is linear.

Example 3: Accelerated Storage Stability Assay

Storage stability of protease variants in liquid detergent was evaluated using an accelerated assay with incubation at elevated temperatures for up to 72 hours.

All purified protease samples were diluted to concentrations of 0.2 and 0.1 mg/ml based on absorbance at 280 nm and theoretical extinction coefficient using 0.01% Triton X-100. For each variant 2 wells with high protease concentration and 2 wells with low concentration were included. As reference SEQ ID NO 4 and SEQ ID NO 5 were included on each microtiter plate. 30 μl protease sample was mixed with 270 μl detergent (Model detergent B) in the well of a microtiter plate (Nunc U96 PP 0.5 ml) using a magnetic bar (on Zephyr pipetting station (Caliper LifeSciences) for 30 min). 20 μl of this mixture was then transferred to another microtiter plate (Nunc U96 PP 0.5 ml with added magnetic bars) and mixed with 150 μl 100 mM Tris pH 8.6 (at least 5 min on Zephyr). 30 μl of this dilution was transferred to a Nunc F 96-MTP, and after addition of 70 μl substrate solution initial activity of unstressed sample was determined by measuring absorbance at 405 nm every 20 sec for 5 min (on a SpectraMax Plus). After sealing, the detergent plate was incubated at appropriate temperature (50° C.) in an Eppendorf Thermomixer (no shaking). After 0, 1-4, 20-25, 40-50 and/or 60-80 hours incubation, 20 μl samples were withdrawn and residual activity of stressed sample was measured as with the initial, unstressed activity.

Decrease in activity during incubation with detergent was assumed to be exponential. Half lifes (t½) were found from linear regression of Log (Activity) versus incubation time, and half-life improvement factors (t½ IF) were calculated as half-life of protease variant relative to half-life of the parent protease.

$$\text{Improvement } factor_{variant} = \frac{t1/2_{variant}}{t1/2_{parent}}$$

Having the improvement factor for each variant, it is possible to calculate the effect of a single mutation, if data are available for at least two variants, that differ only by that mutation. In this case, the improvement factor for the mutation is calculated:

$$\text{Improvement } factor_{mutation} = \frac{\text{Improvement } factor_{variant\ with\ mutation}}{\text{Improvement } factor_{variant\ without\ mutation}}$$

TABLE 2

Composition of liquid laundry model detergent B

| Ingredient | wt % |
| --- | --- |
| (C10-C13)alkylbenzene sulfonic acid | 7.2 |
| sodium lauryl ether sulfate | 10.6 |
| cocoa fatty acid | 2.75 |
| soy fatty acid | 2.75 |
| alcohol ethoxylate with 8 mol EO | 6.6 |
| sodium hydroxide | 1.1 |
| ethanol | 3 |
| propane-1,2-diol | 6 |
| glycerol | 1.7 |
| triethanolamine | 3.3 |
| sodium formiate | 1 |
| sodium citrate | 2 |
| diethylenetriaminepentakis(methylene)pentakis(phosphonic acid), heptasodium salt | 0.5 |
| copoly(acrylic acid/maleic acid), sodium salt | 0.5 |
| deionized water | 51 |

The following Table 3 show: Improvement factor$_{mutation}$ data. Each row show:
- a mutation (column 1: "Mutation")
- a protease variant (relative to SEQ ID NO: 2) that comprise the mutation from column 1 (column 2: "Variant with the mutation")
- another protease variant (relative to SEQ ID NO: 2), that differs from the one in column 2 only by not having the mutation in column 1 (column 3: "Variant without the mutation")
- Improvement factor$_{mutation}$ for the mutation in column 1, in the context of the variant in column 3, in an accelerated storage stability assay as described above (column 4: "IF")

TABLE 3

Stability Improvement factor$_{mutation}$

| Mutation | Variant with the mutation | Variant without the mutation | IF |
|---|---|---|---|
| A1L | A1L, S173P, S175P, F180Y | S173P, S175P, F180Y | 1.10 |
| A1* | A1*, S27K, S173P, S175P, F180Y, Q198E, T297P | S27K, S173P, S175P, F180Y, Q198E, T297P | 2.20 |
| V2I | V2I, S173P, S175P, F180Y | S173P, S175P, F180Y | 1.09 |
| P3* | A1*, P3*, Q6C, S27K, S171N, S173P, G174R, S175P, F180Y, Q198E, T297P | A1*, Q6C, S27K, S171N, S173P, G174R, S175P, F180Y, Q198E, T297P | 13.89 |
| P3* | A1*, P3*, S4C, S27K, S171N, S173P, G174R, S175P, F180Y, Q198E, T297P | A1*, S4C, S27K, S171N, S173P, G174R, S175P, F180Y, Q198E, T297P | 5.25 |
| P3* | A1*, P3*, S4C, S27K, S171N, S173P, G174R, S175P, F180Y, Q198E, E236C, T297P | A1*, S4C, S27K, S171N, S173P, G174R, S175P, F180Y, Q198E, E236C, T297P | 1.07 |
| S4* | A1*, V2*, P3*, S4*, S27K, S173P, S175P, F180Y, Q198E, T297P | A1*, V2*, P3*, S27K, S173P, S175P, F180Y, Q198E, T297P | 1.09 |
| S4C | S4C, S27K, S171N, S173P, G174R, S175P, F180Y, Q198E, E236C, T297P | S27K, S171N, S173P, G174R, S175P, F180Y, Q198E, E236C, T297P | 3.54 |
| Q6C | Q6C, S27K, S171N, S173P, G174R, S175P, F180Y, Q198E, E236C, T297P | S27K, S171N, S173P, G174R, S175P, F180Y, Q198E, E236C, T297P | 2.72 |
| Q18A | Q18A, S173P, S175P, F180Y | S173P, S175P, F180Y | 1.19 |
| L43I | L43I, G47K, R130K, G132R, S173P, S175P | G47K, R130K, G132R, S173P, S175P | 1.12 |
| N59L | S27K, N59L, T67V, Q70N, S171N, S173P, G174R, S175P, F180Y, Q198E, N199K, T297P | S27K, T67V, Q70N, S171N, S173P, G174R, S175P, F180Y, Q198E, N199K, T297P | 1.11 |
| L61K | L61K, S173P, S175P | S173P, S175P | 1.10 |
| V62G | V62G, R69D, S173P, S175P | R69D, S173P, S175P | 1.11 |
| G64A | G64A, R69D, S173P, S175P | R69D, S173P, S175P | 1.08 |
| G64S | G64S, R69D, S173P, S175P | R69D, S173P, S175P | 1.06 |
| S65F | S65F, S173P, S175P, F180Y | S173P, S175P, F180Y | 1.28 |
| Q70T | Q70T, L149T, I150L, S173P, S175P | L149T, I150L, S173P, S175P | 1.09 |
| Q70T | Q70T, I121L, S173P, S175P | I121L, S173P, S175P | 1.15 |
| Q70L | Q70L, S173P, S175P, F180Y | S173P, S175P, F180Y | 1.60 |
| Q70Y | Q70Y, S173P, S175P, F180Y | S173P, S175P, F180Y | 1.44 |
| Q70Y | S27K, Q70Y, E127Q, S173P, S175P, F180Y, Q198E, T297P | S27K, E127Q, S173P, S175P, F180Y, Q198E, T297P | 2.55 |
| Q70F | Q70F, S173P, S175P, F180Y | S173P, S175P, F180Y | 1.38 |
| Q70F | S27K, Q70F, E127Q, S173P, S175P, F180Y, Q198E, T297P | S27K, E127Q, S173P, S175P, F180Y, Q198E, T297P | 2.54 |
| Q70F | S27K, Q70F, G107N, I121V, E127Q, S173P, S175P, F180Y, Q198E, T297P | S27K, G107N, I121V, E127Q, S173P, S175P, F180Y, Q198E, T297P | 2.26 |
| Q70M | Q70M, S173P, S175P, F180Y | S173P, S175P, F180Y | 1.74 |
| Q70A | Q70A, S173P, S175P, F180Y | S173P, S175P, F180Y | 1.43 |
| Q70A | S27K, Q70A, S171N, S173P, G174R, S175P, F180Y, Q198E, N199K, T297P | S27K, S171N, S173P, G174R, S175P, F180Y, Q198E, N199K, T297P | 1.06 |
| Q70A | S27K, Q70A, S114V, E127Q, I150L, S173P, S175P, F180Y, Q198E, T297P | S27K, S114V, E127Q, I150L, S173P, S175P, F180Y, Q198E, T297P | 1.21 |
|

TABLE 3-continued

Stability Improvement factor$_{mutation}$

| Mutation | Variant with the mutation | Variant without the mutation | IF |
|---|---|---|---|
| *108aA | S27K, *108aA, N109S, S111R, S173P, S175P, F180Y, Q198E, T297P | S27K, N109S, S111R, S173P, S175P, F180Y, Q198E, T297P | 1.19 |
| N109T | S27K, N109T, S173P, S175P, F180Y, Q198E, T297P | S27K, S173P, S175P, F180Y, Q198E, T297P | 5.34 |
| *109aA | S27K, N109S, *109aA, S111R, S173P, S175P, F180Y, Q198E, T297P | S27K, N109S, S111R, S173P, S175P, F180Y, Q198E, T297P | 1.10 |
| N109A | S27K, N109A, S173P, S175P, F180Y, Q198E, T297P | S27K, S173P, S175P, F180Y, Q198E, T297P | 4.66 |
| N109A | S27K, N109A, S173P, G174K, S175P, F180Y, Q197K, Q198E, T297P | S27K, S173P, G174K, S175P, F180Y, Q197K, Q198E, T297P | 1.09 |
| S111I | S111I, S173P, S175P, F180Y | S173P, S175P, F180Y | 1.25 |
| Y113S | Q70N, Y113S, S173P, S175P | Q70N, S173P, S175P | 1.15 |
| Y113S | Y113S, A145S, S173P, S175P | A145S, S173P, S175P | 1.36 |
| S114V | S114V, A145S, S173P, S175P | A145S, S173P, S175P | 1.48 |
| S114V | S114V, K146P, S173P, S175P | K146P, S173P, S175P | 1.52 |
| S114V | S114V, M139L, S173P, S175P | M139L, S173P, S175P | 1.08 |
| S114V | S27K, S114V, E127Q, I150L, S173P, S175P, F180Y, Q198E, T297P | S27K, E127Q, I150L, S173P, S175P, F180Y, Q198E, T297P | 1.26 |
| S114V | S27K, S114V, S171N, S173P, G174R, S175P, F180Y, Q198E, N199K, T297P | S27K, S171N, S173P, G174R, S175P, F180Y, Q198E, N199K, T297P | 1.66 |
| S114V | S27K, S114V, S171N, S173P, G174R, S175P, F180Y, Q198E, N199R, T297P | S27K, S171N, S173P, G174R, S175P, F180Y, Q198E, N199R, T297P | 2.94 |
| S114V | S27K, S114V, I150L, S171N, S173P, G174R, S175P, F180Y, Q198E, N199K, T297P | S27K, I150L, S171N, S173P, G174R, S175P, F180Y, Q198E, N199K, T297P | 1.18 |
| S114V | S27K, Q70A, S114V, S173P, G174K, S175P, F180Y, Q198E, N199K, T297P | S27K, Q70A, S173P, G174K, S175P, F180Y, Q198E, N199K, T297P | 1.05 |
| S114A | S114A, S173P, S175P, F180Y | S173P, S175P, F180Y | 1.27 |
| S114A | S27K, Q70N, S114A, S171N, S173P, G174R, S175P, F180Y, Q198E, N199K, T297P | S27K, Q70N, S171N, S173P, G174R, S175P, F180Y, Q198E, N199K, T297P | 1.16 |
| S114F | S114F, S173P, S175P, F180Y | S173P, S175P, F180Y | 1.22 |
| S114F | S27K, S114F, E127Q, S173P, S175P, F180Y, Q198E, T297P | S27K, E127Q, S173P, S175P, F180Y, Q198E, T297P | 2.54 |
| S133H | S27K, S133H, S173P, S175P, F180Y, T297P | S27K, S173P, S175P, F180Y, T297P | 2.22 |
| I137N | I137N, S173P, S175P, F180Y, Q198E, T297P | S173P, S175P, F180Y, Q198E, T297P | 1.53 |
| I137N | S27K, Q97K, I137N, S173P, S175P, F180Y, Q198E, T297P | S27K, Q97K, S173P, S175P, F180Y, Q198E, T297P | 4.30 |
| I137N | S27K, Q97K, I137N, S173P, S175P, F180Y, T297P | S27K, Q97K, S173P, S175P, F180Y, T297P | 2.00 |
| I137N | S27K, I137N, S173P, S175P, F180Y, S270K, T297P | S27K, S173P, S175P, F180Y, S270K, T297P | 1.21 |
| I137N | S27K, S111R, I137N, S173P, S175P, F180Y, T297P | S27K, S111R, S173P, S175P, F180Y, T297P | 1.36 |
| I137N | S27K, E127Q, I137N, S173P, S175P, F180Y, Q198E, T297P | S27K, E127Q, S173P, S175P, F180Y, Q198E, T297P | 4.94 |
| I137N | Q70N, G107N, I137N, S173P, S175P, F180Y, T297P | Q70N, G107N, S173P, S175P, F180Y, T297P | 1.38 |
| I137N | S27K, I137N, S171N, S173P, G174R, S175P, F180Y, Q198E, T297P | S27K, S171N, S173P, G174R, S175P, F180Y, Q198E, T297P | 1.58 |
| I137N | S27K, N109S, S111R, I137N, S173P, S175P, F180Y, Q198E, T297P | S27K, N109S, S111R, S173P, S175P, F180Y, Q198E, T297P | 1.90 |
| M139L | S114V, M139L, S173P, S175P | S114V, S173P, S175P | 1.08 |
| S143R | S27K, S143R, S173P, S175P, F180Y, T297P | S27K, S173P, S175P, F180Y, T297P | 1.46 |
| S144P | S144P, S173P, S175P | S173P, S175P | 1.26 |
| S144P | S144P, A145S, K146P, S148A, L149T, I150L, S173P, S175P | A145S, K146P, S148A, L149T, I150L, S173P, S175P | 2.91 |
| S144P | I137E, S144P, S173P, S175P, F180Y, T297P | I137E, S173P, S175P, F180Y, T297P | 1.08 |
| S144P | S27K, S144P, D147N, S173P, S175P, F180Y, Q198E, T297P | S27K, D147N, S173P, S175P, F180Y, Q198E, T297P | 1.88 |
| S144P | Q70N, I137Q, S144P, S173P, S175P, F180Y, T297P | Q70N, I137Q, S173P, S175P, F180Y, T297P | 1.27 |
| S144P | Q70N, I137N, S144P, S173P, S175P, F180Y, T297P | Q70N, I137N, S173P, S175P, F180Y, T297P | 3.43 |
| S144P | S27K, E127Q, S144P, S173P, S175P, F180Y, Q198E, T297P | S27K, E127Q, S173P, S175P, F180Y, Q198E, T297P | 2.87 |
| S144P | S27K, Q70N, E127Q, S144P, S173P, S175P, F180Y, Q198E, T297P | S27K, Q70N, E127Q, S173P, S175P, F180Y, Q198E, T297P | 1.05 |
| S144P | S27K, S144P, S171N, S173P, G174R, S175P, F180Y, Q198E, N199K, T297P | S27K, S171N, S173P, G174R, S175P, F180Y, Q198E, N199K, T297P | 2.17 |
| S144P | S27K, S144P, K146T, A151R, S171N, S173P, G174R, S175P, F180Y, Q198E, N199K, T297P | S27K, K146T, A151R, S171N, S173P, G174R, S175P, F180Y, Q198E, N199K, T297P | 3.04 |
| S144P | S27K, S144P, K146P, A151R, S171N, S173P, G174R, S175P, F180Y, Q198E, N199K, T297P | S27K, K146P, A151R, S171N, S173P, G174R, S175P, F180Y, Q198E, N199K, T297P | 4.49 |

TABLE 3-continued

Stability Improvement factor$_{mutation}$

| Mutation | Variant with the mutation | Variant without the mutation | IF |
|---|---|---|---|
| S144P | S27K, S144P, K146T, I150L, A151R, S171N, S173P, G174R, S175P, F180Y, Q198E, N199K, T297P | S27K, K146T, I150L, A151R, S171N, S173P, G174R, S175P, F180Y, Q198E, N199K, T297P | 1.73 |
| S144P | S27K, S144P, K146P, I150L, A151R, S171N, S173P, G174R, S175P, F180Y, Q198E, N199K, T297P | S27K, K146P, I150L, A151R, S171N, S173P, G174R, S175P, F180Y, Q198E, N199K, T297P | 2.01 |
| L149T | A145S, K146P, D147S, S148A, L149T, S173P, S175P | A145S, K146P, D147S, S148A, S173P, S175P | 1.64 |
| L149T | I137A, L149T, I150L, S173P, S175P | I137A, I150L, S173P, S175P | 1.12 |
| L149T | K146P, L149T, S173P, S175P | K146P, S173P, S175P | 1.68 |
| L149T | D116S, L149T, S173P, S175P | D116S, S173P, S175P | 2.16

TABLE 3-continued

Stability Improvement factor$_{mutation}$

| Mutation | Variant with the mutation | Variant without the mutation | IF |
|---|---|---|---|
| V162Y | S27K, V162Y, S173P, S175P, F180Y, Q198E, T297P | S27K, S173P, S175P, F180Y, Q198E, T297P | 4.76 |
| V162Y | S27K, E127Q, V162Y, S173P, S175P, F180Y, Q198E, T297P | S27K, E127Q, S173P, S175P, F180Y, Q198E, T297P | 3.87 |
| V162Y | S27K, Q70N, G107N, I121V, E127Q, V162Y, S173P, S175P, F180Y, Q198E, T297P | S27K, Q70N, G107N, I121V, E127Q, S173P, S175P, F180Y, Q198E, T297P | 1.16 |
| V162Y | S27K, V162Y, S173P, G174K, S175P, F180Y, Q198E, N199K, T297P | S27K, S173P, G174K, S175P, F180Y, Q198E, N199K, T297P | 1.26 |
| V162Y | S27K, V162Y, S173P, G174K, S175P, F180Y, Q197K, Q198E, T297P | S27K, S173P, G174K, S175P, F180Y, Q197K, Q198E, T297P | 1.37 |
| V162Y | S27K, V162Y, S171N, S173P, G174R, S175P, F180Y, G182A, L184Y, Q198E, N199K, T297P | S27K, S171N, S173P, G174R, S175P, F180Y, G182A, L184Y, Q198E, N199K, T297P | 1.24 |
| V162Y | S27K, Q70N, G107N, I121V, E127Q, V162Y, S171N, S173P, G174R, S175P, F180Y, Q198E, T297P | S27K, Q70N, G107N, I121V, E127Q, S171N, S173P, G174R, S175P, F180Y, Q198E, T297P | 1.36 |
| I164M | I164M, S173P, S175P, F180Y | S173P, S175P, F180Y | 1.27 |
| S171D | S27K, S171D, S173P, G174R, S175P, F180Y, Q198E, T297P | S27K, S173P, G174R, S175P, F180Y, Q198E, T297P | 2.48 |
| G182A | S173P, S175P, F180Y, G182A | S173P, S175P, F180Y | 4.13 |
| G182A | S27K, K146E, S171N, S173P, G174R, S175P, F180Y, G182A, Q198E, N199K, E223K, T297P | S27K, K146E, S171N, S173P, G174R, S175P, F180Y, Q198E, N199K, E223K, T297P | 2.76 |
| G182A | S27K, S114V, I150L, S171N, S173P, G174R, S175P, F180Y, G182A, Q198E, N199K, T297P | S27K, S114V, I150L, S171N, S173P, G174R, S175P, F180Y, Q198E, N199K, T297P | 1.53 |
| G182A | S27K, S173P, G174K, S175P, G179S, F180Y, G182A, Q198E, N199K, T297P | S27K, S173P, G174K, S175P, G179S, F180Y, Q198E, N199K, T297P | 1.56 |
| G182A | S27K, S173P, G174K, S175P, F180Y, G182A, L184F, V185P, Q198E, N199K, T297P | S27K, S173P, G174K, S175P, F180Y, L184F, V185P, Q198E, N199K, T297P | 3.07 |
| G182A | S27K, S173P, G174K, S175P, F180Y, G182A, L184Y, V185P, Q198E, N199K, T297P | S27K, S173P, G174K, S175P, F180Y, L184Y, V185P, Q198E, N199K, T297P | 3.23 |
| G182A | S27K, Q70N, G107N, I121V, E127Q, S173P, S175P, F180Y, G182A, Q198E, T297P | S27K, Q70N, G107N, I121V, E127Q, S173P, S175P, F180Y, Q198E, T297P | 1.54 |
| G182A | S27K, S173P, G174K, S175P, F180Y, G182A, Q198E, N199K, T297P | S27K, S173P, G174K, S175P, F180Y, Q198E, N199K, T297P | 1.31 |
| G182A | S27K, S173P, G174K, S175P, F180Y, G182A, Q198E, N199K, T297P | S27K, S173P, G174K, S175P, F180Y, Q198E, N199K, T297P | 1.86 |
| G182A | S27K, S173P, G174K, S175P, F180Y, G182A, Q197K, Q198E, T297P | S27K, S173P, G174K, S175P, F180Y, Q197K, Q198E, T297P | 1.32 |
| G182A | S27K, S173P, G174K, S175P, F180Y, G182A, Q198E, N199R, T297P | S27K, S173P, G174K, S175P, F180Y, Q198E, N199R, T297P | 2.09 |
| G182A | I121V, S173P, S175P, F180Y, G182A, T297P | I121V, S173P, S175P, F180Y, T297P | 3.22 |
| G182A | I121V, S173P, S175P, F180Y, G182A, S274V, T297P | I121V, S173P, S175P, F180Y, S274V, T297P | 2.17 |
| G182S | S173P, S175P, F180Y, G182S | S173P, S175P, F180Y | 1.83 |
| Q198E | S173P, S175P, Q198E | S173P, S175P | 2.76 |
| Q198E | S173P, S175P, Q198E | S173P, S175P | 1.51 |
| Q198E | I137E, S173P, S175P, F180Y, Q198E, T297P | I137E, S173P, S175P, F180Y, T297P | 1.39 |
| Q198E | V162R, S173P, S175P, F180Y, Q198E, T297P | V162R, S173P, S175P, F180Y, T297P | 1.85 |
| Q198E | D155N, S173P, S175P, Q198E | D155N, S173P, S175P | 2.11 |
| Q198E | D17N, S173P, S175P, Q198E | D17N, S173P, S175P | 1.74 |
| Q198E | D147N, S173P, S175P, Q198E | D147N, S173P, S175P | 2.13 |
| Q198E | Y156R, S173P, S175P, Q198E | Y156R, S173P, S175P | 2.19 |
| Q198E | S27K, S173P, S175P, Q198E | S27K, S173P, S175P | 3.04 |
| Q198E | D147Q, S173P, S175P, Q198E | D147Q, S173P, S175P | 2.06 |
| Q198E | Q97K, S173P, S175P, Q198E | Q97K, S173P, S175P | 1.98 |
| Q198E | E50Q, S173P, S175P, Q198E | E50Q, S173P, S175P | 2.20 |
| Q198E | S173P, S175P, F180Y, Q198E, V286Q, T297P | S173P, S175P, F180Y, V286Q, T297P | 1.32 |
| Q198E | G107N, S173P, S175P, F180Y, Q198E, T297P | G107N, S173P, S175P, F180Y, T297P | 1.43 |
| Q198E | Y156R, S173P, S175P, F180Y, Q198E, T297P | Y156R, S173P, S175P, F180Y, T297P | 2.10 |
| Q198E | S27K, S173P, S175P, F180Y, Q198E, T297P | S27K, S173P, S175P, F180Y, T297P | 2.10 |
| Q198E | N87K, S173P, S175P, F180Y, Q198E, T297P | N87K, S173P, S175P, F180Y, T297P | 2.00 |
| Q198E | D147Q, S173P, S175P, F180Y, Q198E, T297P | D147Q, S173P, S175P, F180Y, T297P | 1.29 |
| Q198E | I137N, S173P, S175P, F180Y, Q198E, T297P | I137N, S173P, S175P, F180Y, T297P | 1.29 |
| Q198E | I121V, S173P, S175P, F180Y, Q198E, T297P | I121V, S173P, S175P, F180Y, T297P | 1.54 |
| Q198E | S27K, S173P, S175P, F180Y, Q198E, I293R, T297P | S27K, S173P, S175P, F180Y, I293R, T297P | 2.09 |
| Q198E | S27K, S173P, S175P, F180Y, Q198E, S270K, T297P | S27K, S173P, S175P, F180Y, S270K, T297P | 1.60 |
| Q198E | S27K, S173P, G174R, S175P, F180Y, Q198E, T297P | S27K, S173P, G174R, S175P, F180Y, T297P | 1.21 |
| Q198E | S27K, D126G, S173P, S175P, F180Y, Q198E, T297P | S27K, D126G, S173P, S175P, F180Y, T297P | 1.70 |
| Q198E | S27K, Q97K, S173P, S175P, F180Y, Q198E, T297P | S27K, Q97K, S173P, S175P, F180Y, T297P | 1.07 |

TABLE 3-continued

Stability Improvement factor_mutation

| Mutation | Variant with the mutation | Variant without the mutation | IF |
|---|---|---|---|
| Q198E | S27K, Q97K, I137N, S173P, S175P, F180Y, Q198E, T297P | S27K, Q97K, I137N, S173P, S175P, F180Y, T297P | 2.31 |
| Q198E | S27K, S173P, S175P, F180Y, Q197K, Q198E, T297P | S27K, S173P, S175P, F180Y, Q197K, T297P | 2.33 |
| Q198E | S27K, E127Q, I137E, S173P, S175P, F180Y, Q198E, T297P | S27K, E127Q, I137E, S173P, S175P, F180Y, T297P | 13.77 |
| Q198E | S27K, N59L, T67V, N87K, I121V, S171N, S173P, G174R, S175P, F180Y, Q198E, T297P | S27K, N59L, T67V, N87K, I121V, S171N, S173P, G174R, S175P, F180Y, T297P | 1.20 |
| Q198D | S27K, S173P, S175P, F180Y, Q198D, T297P | S27K, S173P, S175P, F180Y, T297P | 2.10 |
| G200C | S173P, S175P, F180Y, E194I, V196I, Q197R, Q198E, N199I, G200C, T297P | S173P, S175P, F180Y, E194I, V196I, Q197R, Q198E, N199I, T297P | 1.15 |
| G200S | S173P, S175P, F180Y, E194I, V196I, Q197R, Q198E, N199I, G200S, T297P | S173P, S175P, F180Y, E194I, V196I, Q197R, Q198E, N199I, T297P | 1.09 |
| A233S | S27K, S171N, S173P, G174R, S175P, F180Y, Q198E, N199K, A233S, T297P | S27K, S171N, S173P, G174R, S175P, F180Y, Q198E, N199K, T297P | 1.70 |
| T246M | S173P, S175P, T246M, I247K | S173P, S175P, I247K | 1.24 |
| A267S | Y113T, E127Q, S173P, G174K, S175P, F180Y, A267S | Y113T, E127Q, S173P, G174K, S175P, F180Y | 3.14 |
| S274V | S27K, S173P, S175P, F180Y, Q198E, S274V, T297P | S27K, S173P, S175P, F180Y, Q198E, T297P | 6.77 |
| S274V | S27K, S173P, G174K, S175P, F180Y, Q198E, N199R, S274V, T297P | S27K, S173P, G174K, S175P, F180Y, Q198E, N199R, T297P | 1.10 |
| S274V | I121V, S173P, S175P, F180Y, S274V, T297P | I121V, S173P, S175P, F180Y, T297P | 1.67 |
| S274V | I121V, S173P, S175P, F180Y, G182A, S274V, T297P | I121V, S173P, S175P, F180Y, G182A, T297P | 1.12 |
| S274V | I121V, S173P, S175P, F180Y, Q198E, N199R, S274V, T297P | I121V, S173P, S175P, F180Y, Q198E, N199R, T297P | 1.23 |
| S274V | S27K, Q70N, I121V, S171N, S173P, G174R, S175P, F180Y, Q198E, S274V, T297P | S27K, Q70N, I121V, S171N, S173P, G174R, S175P, F180Y, Q198E, T297P | 1.06 |
| S274V | S27K, Q70A, S114V, E127Q, I150L, S173P, S175P, F180Y, Q198E, S274V, T297P | S27K, Q70A, S114V, E127Q, I150L, S173P, S175P, F180Y, Q198E, T297P | 2.14 |
| Q275Y | S173P, S175P, F180Y, Q275Y | S173P, S175P, F180Y | 1.16 |
| L276I | S173P, S175P, F180Y, L276I | S173P, S175P, F180Y | 1.11 |

Example 4: Accelerated Storage Stability Assay of SEQ ID NO 4 Variants

Storage stability of protease variants in liquid detergent was evaluated using an accelerated assay with incubation at elevated temperatures for up to 72 hours.

All purified protease samples were diluted to concentrations of 0.2 and 0.1 mg/ml based on absorbance at 280 nm and theoretical extinction coefficient using 0.01% Triton X-100. For each variant 2 wells with high protease concentration and 2 wells with low concentration were included. As reference SEQ ID NO 4 and SEQ ID NO 5 were included on each microtiter plate. 30 µl protease sample was mixed with 270 µl detergent (Model detergent B, described in Example 3) in the well of a microtiter plate (Nunc U96 PP 0.5 ml) using a magnetic bar (on Zephyr pipetting station (Caliper LifeSciences) for 30 min). 20 µl of this mixture was then transferred to another microtiter plate (Nunc U96 PP 0.5 ml with added magnetic bars) and mixed with 150 µl 100 mM Tris pH 8.6 (at least 5 min on Zephyr). 30 µl of this dilution was transferred to a Nunc F 96-MTP, and after addition of 70 µl substrate solution initial activity of unstressed sample was determined by measuring absorbance at 405 nm every 20 sec for 5 min (on a SpectraMax Plus). After sealing, the detergent plate was incubated at appropriate temperature (50° C.) in an Eppendorf Thermomixer (no shaking). After 0, 1-4, 20-25, 40-50 and/or 60-80 hours incubation, 20 µl samples were withdrawn and residual activity of stressed sample was measured as with the initial, unstressed activity. Decrease in activity during incubation with detergent was assumed to be exponential. Half lifes (t %) were found from linear regression of Log (Activity) versus incubation time, and half-life improvement factors (t½ IF) were calculated as half-life of protease variant relative to half-life of the parent protease. The parent protease is, in this case, SEQ ID NO 4.

$$\text{Improvement } factor_{variant} \ (t1/2 \ IF) = \frac{t1/2_{variant}}{t1/2_{parent}}$$

TABLE 4

Stability Half-life Improvement factor

| Variant | t½ IF |
|---|---|
| S173P, S175P (SEQ ID NO 4) | 1.0 |
| S27K, N59L, T67V, I121V, S173P, G174K, S175P, F180Y, G182A, L184Y, Q197K, Q198E, T297P | 25 |
| S27K, I121V, S173P, G174R, S175A, F180Y, G182A, L184Y, Q197K, Q198E, S270V, T297P | 17.6 |
| S27K, Q70A, I121V, E127Q, S173P, G174K, S175P, F180Y, G182A, L184F, Q197K, Q198E, T297P | 19 |
| S27K, Q70A, S171D, S173P, G174R, S175P, F180Y, G182A, L184F, Q198E, N199K, S274V, T297P | 27.5 |
| S27K, Q70N, I121V, S173P, G174K, S175P, G182A, L184F, Q198E, T297P | 37.2 |
| S27K, S171E, S173P, G174K, S175P, F180Y, G182A, L184F, Q198E, N199K, T297P | 26.9 |

TABLE 4-continued

Stability Half-life Improvement factor

| Variant | t½ IF |
|---|---|
| S27K, S173P, G174K, S175P, F180Y, G182A, L184F, Q198E, V286R, T297P | 27.8 |
| S27K, V162T, S171D, S173P, G174R, S175A, F180Y, G182A, L184F, Q197K, Q198E, T297P | 61.3 |
| S27K, S171D, S173P, G174R, S175A, F180Y, G182A, L184F, Q198E, N199K, T297P | 69.2 |
| S27K, N87K, S171D, S173P, G174R, S175P, G182A, L184F, Q198E, N199R, T297P | 23.7 |
| S27K, N109R, S111E, S171E, S173P, G174K, S175P, F180Y, G182A, L184F, Q198E, N199K, T297P | 36.1 |
| S27K, N109K, S111E, S171E, S173P, G174K, S175P, F180Y, G182A, L184F, Q198E, N199K, T297P | 37.5 |
| S27K, *108aA, N109S, V162T, S173P, G174K, S175A, F180Y, G182A, L184F, Q197K, Q198E, T297P | 18.2 |
| S27K, N109R, S111E, V162T, S173P, G174K, S175A, F180Y, G182A, L184F, Q197K, Q198E, T297P | 21.5 |
| S27K, *108aA, N109S, S171D, S173P, G174R, S175A, F180Y, G182A, L184F, Q198E, N199K, T297P | 31.2 |

Example 5: Accelerated Storage Stability Assay of SEQ ID NO 3 Variants

Storage stability of protease variants in liquid detergent was evaluated using an accelerated assay with incubation at elevated temperatures for up to 24 hours. All purified protease samples were diluted to concentrations of 0.2 and 0.1 mg/ml based on absorbance at 280 nm and theoretical extinction coefficient using 0.01% Triton X-100. For each variant 2 wells with high protease concentration and 2 wells with low concentration were included. As reference SEQ ID NO 3 and SEQ ID NO 5 were included on each microtiter plate. 30 µl protease sample was mixed with 270 µl detergent (Model detergent B, described in Example 3) in the well of a microtiter plate (Nunc U96 PP 0.5 ml) using a magnetic bar (on Zephyr pipetting station (Caliper LifeSciences) for 30 min). 20 µl of this mixture was then transferred to another microtiter plate (Nunc U96 PP 0.5 ml with added magnetic bars) and mixed with 150 µl 100 mM Tris pH 8.6 (at least 5 min on Zephyr). 30 µl of this dilution was transferred to a Nunc F 96-MTP, and after addition of 70 µl substrate solution initial activity of unstressed sample was determined by measuring absorbance at 405 nm every 20 sec for 5 min (on a SpectraMax Plus). After sealing, the detergent plate was incubated at appropriate temperature (32° C.) in an Eppendorf Thermomixer (no shaking). After 0, 2, 6, and/or 24 hours incubation, 30 µl samples were withdrawn and residual activity of stressed sample was measured as with the initial, unstressed activity. Decrease in activity during incubation with detergent was assumed to be exponential. Half lifes (t½) were found from linear regression of Log (Activity) versus incubation time, and half-life improvement factors (VA IF) were calculated as half-life of protease variant relative to half-life of the parent protease. The parent protease is, in this case, SEQ ID NO 3.

$$\text{Improvement } factor_{variant} \ (t1/2 \ IF) = \frac{t1/2_{variant}}{t1/2_{parent}}$$

TABLE 5

Stability Half-life Improvement factor

| Variant | IF |
|---|---|
| SEQ ID NO 3 | 1.0 |
| L149R | 1.5 |
| E127R | 1.1 |
| D126K | 1.1 |
| D126G | 1.3 |
| E127Q | 1.1 |
| E50Q | 1.1 |
| S274V | 1.2 |
| Q97K | 1.1 |
| S144P | 1.2 |
| S111R | 1.4 |
| A145E | 1.2 |
| S144R | 1.3 |
| Q70N | 1.1 |
| S114A | 1.1 |
| G182A | 1.8 |

The invention claimed is:

1. A protease variant comprising one or more alterations selected from the group consisting of A1L, A1*, V2I, P3*, S4*, S4C, Q6C, Q18A, L43I, E50Q, N59L, L61K, V62G, G64A, G64S, S65F, Q70T, Q70L, Q70N Q70Y, Q70F, Q70M, Q70A, Q70V, Q97K, G107N, *108aA, N109T, *109aA, N109A, S111I, S111R, Y113S, S114V, S114A, S114F, D126G, D126K, E127R, E127Q, S133H, I137N, M139L, S143R, S144P, S144R, A145E, L149R, L149T, I150L, I150T, I150S, I150V, V162S, V162E, V162Q, V162G, V162F, V162T, V162Y, I164M, S171D, G182A, G182S, Q198E, Q198D, G200C, G200S, A233S, T246M, A267S, S274V, Q275Y, L276I and T297P, wherein positions correspond to the positions of SEQ ID NO: 3, and wherein the protease variant has protease activity and a sequence identity to SEQ ID NO: 3 of at least 75%;

and wherein the variant comprises a set of alterations compared to SEQ ID NO: 3 selected from the group consisting of:
A1L, S173P, S175P, F180Y;
A1*, S27K, S173P, S175P, F180Y, Q198E, T297P;
V2I, S173P, S175P, F180Y;
A1*, P3*, Q6C, S27K, S171N, S173P, G174R, S175P, F180Y, Q198E, T297P;
A1*, P3*, S4C, S27K, S171N, S173P, G174R, S175P, F180Y, Q198E, T297P;
A1*, P3*, S4C, S27K, S171N, S173P, G174R, S175P, F180Y, Q198E, E236C, T297P;
A1*, V2*, P3*, S4*, S27K, S173P, S175P, F180Y, Q198E, T297P;
S4C, S27K, S171N, S173P, G174R, S175P, F180Y, Q198E, E236C, T297P;
Q6C, S27K, S171N, S173P, G174R, S175P, F180Y, Q198E, E236C, T297P;
Q18A, S173P, S175P, F180Y;
L43I, G47K, R130K, G132R, S173P, S175P;
S27K, N59L, T67V, Q70N, S171N, S173P, G174R, S175P, F180Y, Q198E, N199K, T297P;
L61K, S173P, S175P;
V62G, R69D, S173P, S175P;
G64A, R69D, S173P, S175P;
G64S, R69D, S173P, S175P;
S65F, S173P, S175P, F180Y;
Q70T, L149T, I150L, S173P, S175P;
Q70T, I121L, S173P, S175P;
Q70L, S173P, S175P, F180Y;
Q70Y, S173P, S175P, F180Y;
S27K, Q70Y, E127Q, S173P, S175P, F180Y, Q198E, T297P;
Q70F, S173P, S175P, F180Y;
S27K, Q70F, E127Q, S173P, S175P, F180Y, Q198E, T297P;
S27K, Q70F, G107N, I121V, E127Q, S173P, S175P, F180Y, Q198E, T297P;
Q70M, S173P, S175P, F180Y;
Q70A, S173P, S175P, F180Y;
S27K, Q70A, S171N, S173P, G174R, S175P, F180Y, Q198E, N199K, T297P;
S27K, Q70A, S114V, E127Q, I150L, S173P, S175P, F180Y, Q198E, T297P;
S27K, Q70A, G107N, I121V, E127Q, S173P, S175P, F180Y, Q198E, T297P;
S27K, Q70A, I121V, S171N, S173P, G174R, S175P, F180Y, Q198E, T297P;
S27K, Q70A, G107N, I121V, E127Q, S173P, S175P, F180Y, Q198E, T297P;
S27K, Q70A, S114V, S173P, G174K, S175P, F180Y, Q198E, N199K, T297P;
S27K, Q70V, S171N, S173P, G174R, S175P, F180Y, Q198E, N199K, T297P;
S27K, Q70V, S114V, E127Q, I150L, S173P, S175P, F180Y, Q198E, T297P;
S27K, Q70V, G107N, I121V, E127Q, S173P, S175P, F180Y, Q198E, T297P;
S27K, Q70V, S171N, S173P, G174R, S175P, F180Y, Q198E, T297P;
G107N, S173P, S175P, F180Y, Q198E, T297P;
Q70N, G107N, I137Q, S173P, S175P, F180Y, T297P;
Q70N, G107N, I137N, S173P, S175P, F180Y, T297P;
S27K, G107N, E127Q, S173P, S175P, F180Y, Q198E, T297P;
S27K, N59L, T67V, N87K, G107N, I121V, S171N, S173P, G174R, S175P, F180Y, Q198E, T297P;
S27K, Y39R, G107N, I137E, S173P, S175P, F180Y, T297P;
S27K, Q70N, N87K, G107N, I121V, E127Q, S171N, S173P, G174R, S175P, F180Y, Q198E, T297P;
S27K, *108aA, N109S, S111R, S173P, S175P, F180Y, Q198E, T297P;
S27K, N109T, S173P, S175P, F180Y, Q198E, T297P;
S27K, N109S, *109aA, S111R, S173P, S175P, F180Y, Q198E, T297P;
S27K, N109A, S173P, S175P, F180Y, Q198E, T297P;
S27K, N109A, S173P, G174K, S175P, F180Y, Q197K, Q198E, T297P;
S111I, S173P, S175P, F180Y;
Q70N, Y113S, S173P, S175P;
Y113S, A145S, S173P, S175P;
S114V, A145S, S173P, S175P;
S114V, K146P, S173P, S175P;
S114V, M139L, S173P, S175P;
S27K, S114V, E127Q, I150L, S173P, S175P, F180Y, Q198E, T297P;
S27K, S114V, S171N, S173P, G174R, S175P, F180Y, Q198E, N199K, T297P;
S27K, S114V, S171N, S173P, G174R, S175P, F180Y, Q198E, N199R, T297P;
S27K, S114V, I150L, S171N, S173P, G174R, S175P, F180Y, Q198E, N199K, T297P;
S27K, Q70A, S114V, S173P, G174K, S175P, F180Y, Q198E, N199K, T297P;
S114A, S173P, S175P, F180Y;
S27K, Q70N, S114A, S171N, S173P, G174R, S175P, F180Y, Q198E, N199K, T297P;
S114F, S173P, S175P, F180Y;

S27K, S114F, E127Q, S173P, S175P, F180Y, Q198E, T297P;
S27K, S133H, S173P, S175P, F180Y, T297P;
I137N, S173P, S175P, F180Y, Q198E, T297P;
S27K, Q97K, I137N, S173P, S175P, F180Y, Q198E, T297P;
S27K, Q97K, I137N, S173P, S175P, F180Y, T297P;
S27K, I137N, S173P, S175P, F180Y, S270K, T297P;
S27K, S111R, I137N, S173P, S175P, F180Y, T297P;
S27K, E127Q, I137N, S173P, S175P, F180Y, Q198E, T297P;
Q70N, G107N, I137N, S173P, S175P, F180Y, T297P;
S27K, I137N, S171N, S173P, G174R, S175P, F180Y, Q198E, T297P;
S27K, N109S, S111R, I137N, S173P, S175P, F180Y, Q198E, T297P;
S114V, M139L, S173P, S175P;
S27K, S143R, S173P, S175P, F180Y, T297P;
S144P, S173P, S175P;
S144P, A145S, K146P, S148A, L149T, I150L, S173P, S175PI137E, S144P, S173P, S175P, F180Y, T297P;
S27K, S144P, D147N, S173P, S175P, F180Y, Q198E, T297P;
Q70N, I137Q, S144P, S173P, S175P, F180Y, T297P;
Q70N, I137N, S144P, S173P, S175P, F180Y, T297P;
S27K, E127Q, S144P, S173P, S175P, F180Y, Q198E, T297P;
S27K, Q70N, E127Q, S144P, S173P, S175P, F180Y, Q198E, T297P;
S27K, S144P, S171N, S173P, G174R, S175P, F180Y, Q198E, N199K, T297P;
S27K, S144P, K146T, A151R, S171N, S173P, G174R, S175P, F180Y, Q198E, N199K, T297P;
S27K, S144P, K146P, A151R, S171N, S173P, G174R, S175P, F180Y, Q198E, N199K, T297P;
S27K, S144P, K146T, I150L, A151R, S171N, S173P, G174R, S175P, F180Y, Q198E, N199K, T297P;
S27K, S144P, K146P, I150L, A151R, S171N, S173P, G174R, S175P, F180Y, Q198E, N199K, T297P;
A145S, K146P, D147S, S148A, L149T, S173P, S175P;
I137A, L149T, I150L, S173P, S175P;
K146P, L149T, S173P, S175P;
D116S, L149T, S173P, S175P;
S27K, S114V, E127Q, I150L, S173P, S175P, F180Y, Q198E, T297P;
S27K, Q70N, E127Q, I150L, S173P, S175P, F180Y, Q198E, T297P;
S27K, I150L, S171N, S173P, G174R, S175P, F180Y, Q198E, N199K, T297P;
S27K, I150L, S171N, S173P, G174R, S175P, F180Y, Q198E, N199R, T297P;
S27K, K146T, I150L, A151R, S171N, S173P, G174R, S175P, F180Y, Q198E, N199K, T297P;
S27K, K146P, I150L, A151R, S171N, S173P, G174R, S175P, F180Y, Q198E, N199K, T297P;
S27K, S144R, K146T, I150L, A151R, S171N, S173P, G174R, S175P, F180Y, Q198E, N199K, T297P;
I150T, S173P, S175P, F180Y;
N16H, S27K, E50H, G132H, I150S, S173P, S175P, F180Y, Q198E, T297P;
S27K, I150S, S171N, S173P, G174R, S175P, F180Y, Q198E, N199K, T297P;
S27K, I150S, S171N, S173P, G174R, S175P, F180Y, Q198E, N199R, T297P;
S27K, K146T, I150S, A151R, S171N, S173P, G174R, S175P, F180Y, Q198E, N199K, T297P;
S27K, K146P, I150S, A151R, S171N, S173P, G174R, S175P, F180Y, Q198E, N199K, T297P;
S27K, Q70N, I121V, I150S, S171N, S173P, G174R, S175P, F180Y, Q198E, T297P;
I150V, S173P, S175P, F180Y;
S27K, V162S, S173P, S175P, F180Y, Q198E, T297P;
S27K, E127Q, V162S, S173P, S175P, F180Y, Q198E, T297P;
N16H, S27K, E50H, G132H, V162S, S173P, S175P, F180Y, Q198E, T297P;
S27K, V162E, S173P, S175P, F180Y, Q198E, T297P;
S27K, E127Q, V162E, S173P, S175P, F180Y, Q198E, T297P;
S27K, V162Q, S173P, S175P, F180Y, Q198E, T297P;
S27K, E127Q, V162Q, S173P, S175P, F180Y, Q198E, T297P;
S27K, V162G, S173P, S175P, F180Y, Q198E, T297P;
S27K, E127Q, V162G, S173P, S175P, F180Y, Q198E, T297P;
S27K, V162F, S173P, S175P, F180Y, Q198E, T297P;
S27K, E127Q, V162F, S173P, S175P, F180Y, Q198E, T297P;
S27K, I121V, V162F, S171N, S173P, G174R, S175P, F180Y, Q198E, T297P;
S27K, V162F, S173P, G174K, S175P, F180Y, Q197K, Q198E, T297P;
S27K, V162T, S173P, S175P, F180Y, Q198E, T297P;
S27K, E127Q, V162T, S173P, S175P, F180Y, Q198E, T297P;
S27K, V162T, S173P, G174K, S175P, F180Y, Q198E, N199R, T297P;
S27K, V162Y, S173P, S175P, F180Y, Q198E, T297P;
S27K, E127Q, V162Y, S173P, S175P, F180Y, Q198E, T297P;
S27K, Q70N, G107N, I121V, E127Q, V162Y, S173P, S175P, F180Y, Q198E, T297P;
S27K, V162Y, S173P, G174K, S175P, F180Y, Q198E, N199K, T297P;
S27K, V162Y, S173P, G174K, S175P, F180Y, Q197K, Q198E, T297P;
S27K, V162Y, S171N, S173P, G174R, S175P, F180Y, G182A, L184Y, Q198E, N199K, T297P;
S27K, Q70N, G107N, I121V, E127Q, V162Y, S171N, S173P, G174R, S175P, F180Y, Q198E, T297P;
I164M, S173P, S175P, F180Y;
S27K, S171D, S173P, G174R, S175P, F180Y, Q198E, T297P;
S173P, S175P, F180Y, G182A;
S27K, K146E, S171N, S173P, G174R, S175P, F180Y, G182A, Q198E, N199K, E223K, T297P;
S27K, S114V, I150L, S171N, S173P, G174R, S175P, F180Y, G182A, Q198E, N199K, T297P;
S27K, S173P, G174K, S175P, G179S, F180Y, G182A, Q198E, N199K, T297P;
S27K, S173P, G174K, S175P, F180Y, G182A, L184F, V185P, Q198E, N199K, T297P;
S27K, S173P, G174K, S175P, F180Y, G182A, L184Y, V185P, Q198E, N199K, T297P;
S27K, Q70N, G107N, I121V, E127Q, S173P, S175P, F180Y, G182A, Q198E, T297P;
S27K, S173P, G174K, S175P, F180Y, G182A, Q198E, N199K, T297P;
S27K, S173P, G174K, S175P, F180Y, G182A, Q198E, N199K, T297P;
S27K, S173P, G174K, S175P, F180Y, G182A, Q197K, Q198E, T297P;

S27K, S173P, G174K, S175P, F180Y, G182A, Q198E, N199R, T297P;
I121V, S173P, S175P, F180Y, G182A, T297P;
I121V, S173P, S175P, F180Y, G182A, S274V, T297P;
S173P, S175P, F180Y, G182S;
S173P, S175P, Q198E;
S173P, S175P, Q198E;
I137E, S173P, S175P, F180Y, Q198E, T297P;
V162R, S173P, S175P, F180Y, Q198E, T297P;
D155N, S173P, S175P, Q198E;
D17N, S173P, S175P, Q198E;
D147N, S173P, S175P, Q198E;
Y156R, S173P, S175P, Q198E;
S27K, S173P, S175P, Q198E;
D147Q, S173P, S175P, Q198E;
Q97K, S173P, S175P, Q198E;
E50Q, S173P, S175P, Q198E;
S173P, S175P, F180Y, Q198E, V286Q, T297P;
G107N, S173P, S175P, F180Y, Q198E, T297P;
Y156R, S173P, S175P, F180Y, Q198E, T297P;
S27K, S173P, S175P, F180Y, Q198E, T297P;
N87K, S173P, S175P, F180Y, Q198E, T297P;
D147Q, S173P, S175P, F180Y, Q198E, T297P;
I137N, S173P, S175P, F180Y, Q198E, T297P;
I121V, S173P, S175P, F180Y, Q198E, T297P;
S27K, S173P, S175P, F180Y, Q198E, I293R, T297P;
S27K, S173P, S175P, F180Y, Q198E, S270K, T297P;
S27K, S173P, G174R, S175P, F180Y, Q198E, T297P;
S27K, D126G, S173P, S175P, F180Y, Q198E, T297P;
S27K, Q97K, S173P, S175P, F180Y, Q198E, T297P;
S27K, Q97K, I137N, S173P, S175P, F180Y, Q198E, T297P;
S27K, S173P, S175P, F180Y, Q197K, Q198E, T297P;
S27K, E127Q, I137E, S173P, S175P, F180Y, Q198E, T297P;
S27K, N59L, T67V, N87K, I121V, S171N, S173P, G174R, S175P, F180Y, Q198E, T297P;
S27K, S173P, S175P, F180Y, Q198D, T297P;
S173P, S175P, F180Y, E194I, V196I, Q197R, Q198E, N199I, G200C, T297P;
S173P, S175P, F180Y, E194I, V196I, Q197R, Q198E, N199I, G200S, T297P;
S27K, S171N, S173P, G174R, S175P, F180Y, Q198E, N199K, A233S, T297P;
S173P, S175P, T246M, I247K;
Y113T, E127Q, S173P, G174K, S175P, F180Y, A267S;
S27K, S173P, S175P, F180Y, Q198E, S274V, T297P;
S27K, S173P, G174K, S175P, F180Y, Q198E, N199R, S274V, T297P;
I121V, S173P, S175P, F180Y, S274V, T297P;
I121V, S173P, S175P, F180Y, G182A, S274V, T297P;
I121V, S173P, S175P, F180Y, Q198E, N199R, S274V, T297P;
S27K, Q70N, I121V, S171N, S173P, G174R, S175P, F180Y, Q198E, S274V, T297P;
S27K, Q70A, S114V, E127Q, I150L, S173P, S175P, F180Y, Q198E, S274V, T297P;
S173P, S175P, F180Y, Q275Y;
S173P, S175P, F180Y, L276I;
S27K, N59L, T67V, I121V, S173P, G174K, S175P, F180Y, G182A, L184Y, Q197K, Q198E, T297P;
S27K, I121V, S173P, G174R, S175A, F180Y, G182A, L184Y, Q197K, Q198E, S270V, T297P;
S27K, Q70A, I121V, E127Q, S173P, G174K, S175P, F180Y, G182A, L184F, Q197K, Q198E, T297P;
S27K, Q70A, S171D, S173P, G174R, S175P, F180Y, G182A, L184F, Q198E, N199K, S274V, T297P;

S27K, Q70N, I121V, S173P, G174K, S175P, G182A, L184F, Q198E, T297P;
S27K, S171E, S173P, G174K, S175P, F180Y, G182A, L184F, Q198E, N199K, T297P;
S27K, S173P, G174K, S175P, F180Y, G182A, L184F, Q198E, V286R, T297P;
S27K, V162T, S171D, S173P, G174R, S175A, F180Y, G182A, L184F, Q197K, Q198E, T297P;
S27K, S171D, S173P, G174R, S175A, F180Y, G182A, L184F, Q198E, N199K, T297P;
S27K, N87K, S171D, S173P, G174R, S175P, G182A, L184F, Q198E, N199R, T297P;
S27K, N109R, S111E, S171E, S173P, G174K, S175P, F180Y, G182A, L184F, Q198E, N199K, T297P;
S27K, N109K, S111E, S171E, S173P, G174K, S175P, F180Y, G182A, L184F, Q198E, N199K, T297P;
S27K, *108aA, N109S, V162T, S173P, G174K, S175A, F180Y, G182A, L184F, Q197K, Q198E, T297P;
S27K, N109R, S111E, V162T, S173P, G174K, S175A, F180Y, G182A, L184F, Q197K, Q198E, T297P; and
S27K, *108aA, N109S, S171D, S173P, G174R, S175A, F180Y, G182A, L184F, Q198E, N199K, T297P.

2. The protease variant of claim 1, wherein the variant comprises a set of alterations compared to SEQ ID NO. 3 selected from the group consisting of:
S27K, Q70A, I121V, E127Q, S173P, G174K, S175P, F180Y, G182A, L184F, Q197K, Q198E, T297P;
S27K, *108aA, N109S, V162T, S173P, G174K, S175A, F180Y, G182A, L184F, Q197K, Q198E, T297P;
S27K, I121V, S173P, G174R, S175A, F180Y, G182A, L184Y, Q197K, Q198E, S270V, T297;
S27K, N59L, T67V, I121V, S173P, G174K, S175P, F180Y, G182A, L184Y, Q197K, Q198E, T297P;
S27K, N109R, S111E, V162T, S173P, G174K, S175A, F180Y, G182A, L184F, Q197K, Q198E, T297P;
S27K, N87K, S171D, S173P, G174R, S175P, G182A, L184F, Q198E, N199R, T297P;
S27K, Q70A, S171D, S173P, G174R, S175P, F180Y, G182A, L184F, Q198E, N199K, S274V, T297P;
S27K, *108aA, N109S, S171D, S173P, G174R, S175A, F180Y, G182A, L184F, Q198E, N199K, T297P;
S27K, S171E, S173P, G174K, S175P, F180Y, G182A, L184F, Q198E, N199K, T297P;
S27K, S173P, G174K, S175P, F180Y, G182A, L184F, Q198E, V286R, T297P;
S27K, N109R, S111E, S171E, S173P, G174K, S175P, F180Y, G182A, L184F, Q198E, N199K, T297P;
S27K, Q70N, I121V, S173P, G174K, S175P, G182A, L184F, Q198E, T297P;
S27K, N109K, S111E, S171E, S173P, G174K, S175P, F180Y, G182A, L184F, Q198E, N199K, T297P;
S27K, V162T, S171D, S173P, G174R, S175A, F180Y, G182A, L184F, Q197K, Q198E, T297P; and
S27K, S171D, S173P, G174R, S175A, F180Y, G182A, L184F, Q198E, N199K, T297P.

3. The protease variant of claim 1, wherein the variant has at least 80% sequence identity to SEQ ID NO: 3.

4. The protease variant of claim 1, wherein the variant has at least 85% sequence identity to SEQ ID NO: 3.

5. The protease variant of claim 1, wherein the variant has at least 90% sequence identity to SEQ ID NO: 3.

6. The protease variant of claim 1, wherein the variant has at least 95% sequence identity to SEQ ID NO: 3.

7. A detergent composition comprising a variant according to claim 1 and one or more detergent components.

* * * * *

SEQUENCE LISTING

<160> NUMBER OF SEQ ID NOS: 5

<210> SEQ ID NO 1
<211> LENGTH: 1263
<212> TYPE: DNA
<213> ORGANISM: bacillius sp.
<220> FEATURE:
<221> NAME/KEY: CDS
<222> LOCATION: (1)..(1263)
<220> FEATURE:
<221> NAME/KEY: sig_peptide
<222> LOCATION: (1)..(80)
<220> FEATURE:
<221> NAME/KEY: mat_peptide
<222> LOCATION: (331)..(1263)

<400> SEQUENCE: 1

```
atg aag aaa ccg ttg ggg aaa att gtc gca agc acc gca cta ctc        45
Met Lys Lys Pro Leu Gly Lys Ile Val Ala Ser Thr Ala Leu Leu
-110              -105                -100 att tct gtt gct ttt agt tca tcg atc gca tcg gct gca ctt gca aaa    93
Ile Ser Val Ala Phe Ser Ser Ser Ile Ala Ser Ala Ala Leu Ala Lys
 -95              -90                 -85                -80 gac aaa gtt gag gta aag gaa caa gat tca tat cgt gtg cta atc aaa    141
Asp Lys Val Glu Val Lys Glu Gln Asp Ser Tyr Arg Val Leu Ile Lys
                 -75                 -70                -65 gca cca act aca tca atc agt act ttt caa tca caa tac gat gtc cgt    189
Ala Pro Thr Thr Ser Ile Ser Thr Phe Gln Ser Gln Tyr Asp Val Arg
             -60                 -55                -50 tgg gat ttt ggc aaa gag gga ttt aca aca gat gtt gat gcc aaa cag    237
Trp Asp Phe Gly Lys Glu Gly Phe Thr Thr Asp Val Asp Ala Lys Gln
         -45                 -40                -35 ctc caa acg ctt caa agc aac aaa gac att caa att cag aag gta aat    285
Leu Gln Thr Leu Gln Ser Asn Lys Asp Ile Gln Ile Gln Lys Val Asn
     -30                 -25                -20 gaa atg aca gta gaa act gtt aca aca gaa aag gcg gaa gtg acg gcg    333
Glu Met Thr Val Glu Thr Val Thr Thr Glu Lys Ala Glu Val Thr Ala
-15                 -10                 -5              -1  1 gta cca agt aca caa acc cct tgg ggc ata aag tca att tat aat gat    381
Val Pro Ser Thr Gln Thr Pro Trp Gly Ile Lys Ser Ile Tyr Asn Asp
             5                   10                  15 caa tca att aca aaa aca act gga ggc agc gga att aag gta gct gtt    429
Gln Ser Ile Thr Lys Thr Thr Gly Gly Ser Gly Ile Lys Val Ala Val
         20                  25                  30 tta gat aca ggg gtt tat aca agc cat tta gat tta gct ggt tct gcc    477
Leu Asp Thr Gly Val Tyr Thr Ser His Leu Asp Leu Ala Gly Ser Ala
     35                  40                  45 gag caa tgc aag gat ttt acc caa tct aat cct tta gta gat ggt tca    525
Glu Gln Cys Lys Asp Phe Thr Gln Ser Asn Pro Leu Val Asp Gly Ser
 50                  55                  60                  65 tgc acc gat cgc caa ggg cat ggt aca cat gtt gcc gga act gta ttg    573
Cys Thr Asp Arg Gln Gly His Gly Thr His Val Ala Gly Thr Val Leu
             70                  75                  80 gcg cat gga ggc agt aat gga caa ggc gtt tac ggg gtg gct ccg caa    621
Ala His Gly Gly Ser Asn Gly Gln Gly Val Tyr Gly Val Ala Pro Gln
         85                  90                  95 gcg aaa cta tgg gca tat aaa gta tta gga gat aac ggc agc gga tac    669
Ala Lys Leu Trp Ala Tyr Lys Val Leu Gly Asp Asn Gly Ser Gly Tyr
     100                 105                 110 tct gat gat att gca gca gct atc aga cat gta gct gat gaa gct tca    717
Ser Asp Asp Ile Ala Ala Ala Ile Arg His Val Ala Asp Glu Ala Ser
 115                 120                 125 cgt aca ggt tcc aaa gta gta att aat atg tcg cta ggt tca tct gcc    765
Arg Thr Gly Ser Lys Val Val Ile Asn Met Ser Leu Gly Ser Ser Ala
130                 135                 140                 145 aag gat tca ttg att gct agt gca gta gat tat gca tat gga aaa ggt    813
Lys Asp Ser Leu Ile Ala Ser Ala Val Asp Tyr Ala Tyr Gly Lys Gly
             150                 155                 160 gta tta atc gtt gct gcg gct ggt aat agt ggg tca ggc agc aat aca    861
Val Leu Ile Val Ala Ala Ala Gly Asn Ser Gly Ser Gly Ser Asn Thr
         165                 170                 175 atc ggc ttt cct ggc ggg ctt gta aat gca gtg gca gta gcg gca ttg    909
Ile Gly Phe Pro Gly Gly Leu Val Asn Ala Val Ala Val Ala Ala Leu
     180                 185                 190
```

| | | | | | | | | | | | | | | | |
|---|---|---|---|---|---|---|---|---|---|---|---|---|---|---|---|
| gag | aat | gtt | cag | caa | aat | gga | act | tat | cga | gta | gct | gat | ttc | tca | tct | 957 |
| Glu | Asn | Val | Gln | Gln | Asn | Gly | Thr | Tyr | Arg | Val | Ala | Asp | Phe | Ser | Ser | |
| 195 | | | | 200 | | | | | 205 | | | | | | | |
| aga | ggg | aat | ccg | gca | act | gct | gga | gat | tat | atc | att | caa | gag | cgt | gat | 1005 |
| Arg | Gly | Asn | Pro | Ala | Thr | Ala | Gly | Asp | Tyr | Ile | Ile | Gln | Glu | Arg | Asp | |
| 210 | | | | 215 | | | | | 220 | | | | | 225 | | |
| att | gaa | gtt | tca | gct | ccg | gga | gca | agt | gta | gag | tct | aca | tgg | tac | act | 1053 |
| Ile | Glu | Val | Ser | Ala | Pro | Gly | Ala | Ser | Val | Glu | Ser | Thr | Trp | Tyr | Thr | |
| | | | | 230 | | | | | 235 | | | | | 240 | | |
| ggc | ggt | tat | aat | acg | atc | agc | ggt | aca | tca | atg | gct | aca | cct | cat | gta | 1101 |
| Gly | Gly | Tyr | Asn | Thr | Ile | Ser | Gly | Thr | Ser | Met | Ala | Thr | Pro | His | Val | |
| | | | 245 | | | | | 250 | | | | | 255 | | | |
| gct | ggg | tta | gct | gct | aaa | atc | tgg | tca | gcg | aat | act | tca | tta | agt | cat | 1149 |
| Ala | Gly | Leu | Ala | Ala | Lys | Ile | Trp | Ser | Ala | Asn | Thr | Ser | Leu | Ser | His | |
| | 260 | | | | | 265 | | | | | 270 | | | | | |
| agc | caa | ctg | cgc | aca | gaa | ttg | caa | aat | cgc | gct | aaa | gta | tat | gat | att | 1197 |
| Ser | Gln | Leu | Arg | Thr | Glu | Leu | Gln | Asn | Arg | Ala | Lys | Val | Tyr | Asp | Ile | |
| 275 | | | | | 280 | | | | | 285 | | | | | | |
| aaa | ggt | ggt | atc | gga | gcc | gga | aca | ggt | gac | gat | tat | gca | tca | ggg | ttc | 1245 |
| Lys | Gly | Gly | Ile | Gly | Ala | Gly | Thr | Gly | Asp | Asp | Tyr | Ala | Ser | Gly | Phe | |
| 290 | | | | 295 | | | | | 300 | | | | | 305 | | |
| gga | tat | cca | aga | gta | aaa | | | | | | | | | | | 1263 |
| Gly | Tyr | Pro | Arg | Val | Lys | | | | | | | | | | | |
| | | 310 | | | | | | | | | | | | | | |

```
<210> SEQ ID NO 2
<211> LENGTH: 421
<212> TYPE: PRT
<213> ORGANISM: bacillius sp.

<400> SEQUENCE: 2
```

Met Lys Lys Pro Leu Gly Lys Ile Val Ala Ser Thr Ala Leu Leu
-110                -105                  -100

Ile Ser Val Ala Phe Ser Ser Ile Ala Ser Ala Ala Leu Ala Lys
-95                 -90                   -85              -80

Asp Lys Val Glu Val Lys Glu Gln Asp Ser Tyr Arg Val Leu Ile Lys
           -75                 -70                      -65

Ala Pro Thr Thr Ser Ile Ser Thr Phe Gln Ser Gln Tyr Asp Val Arg
               -60                  -55                     -50

Trp Asp Phe Gly Lys Glu Gly Phe Thr Thr Asp Val Asp Ala Lys Gln
        -45                 -40                     -35

Leu Gln Thr Leu Gln Ser Asn Lys Asp Ile Gln Ile Gln Lys Val Asn
        -30                 -25                 -20

Glu Met Thr Val Glu Thr Val Thr Thr Glu Lys Ala Glu Val Thr Ala
-15                 -10                  -5                -1   1

Val Pro Ser Thr Gln Thr Pro Trp Gly Ile Lys Ser Ile Tyr Asn Asp
            5                   10                  15

Gln Ser Ile Thr Lys Thr Thr Gly Gly Ser Gly Ile Lys Val Ala Val
            20                  25                  30

Leu Asp Thr Gly Val Tyr Thr Ser His Leu Asp Leu Ala Gly Ser Ala
        35                  40                  45

Glu Gln Cys Lys Asp Phe Thr Gln Ser Asn Pro Leu Val Asp Gly Ser
50                  55                  60                  65

Cys Thr Asp Arg Gln Gly His Gly Thr His Val Ala Gly Thr Val Leu
                70                  75                  80

Ala His Gly Gly Ser Asn Gly Gln Gly Val Tyr Gly Val Ala Pro Gln
            85                  90                  95

```
Ala Lys Leu Trp Ala Tyr Lys Val Leu Gly Asp Asn Gly Ser Gly Tyr
            100                 105                 110

Ser Asp Asp Ile Ala Ala Ala Ile Arg His Val Ala Asp Glu Ala Ser
    115                 120                 125

Arg Thr Gly Ser Lys Val Val Ile Asn Met Ser Leu Gly Ser Ser Ala
130                 135                 140                 145

Lys Asp Ser Leu Ile Ala Ser Ala Val Asp Tyr Ala Tyr Gly Lys Gly
                150                 155                 160

Val Leu Ile Val Ala Ala Ala Gly Asn Ser Gly Ser Gly Ser Asn Thr
            165                 170                 175

Ile Gly Phe Pro Gly Gly Leu Val Asn Ala Val Ala Val Ala Ala Leu
            180                 185                 190

Glu Asn Val Gln Gln Asn Gly Thr Tyr Arg Val Ala Asp Phe Ser Ser
    195                 200                 205

Arg Gly Asn Pro Ala Thr Ala Gly Asp Tyr Ile Ile Gln Glu Arg Asp
210                 215                 220                 225

Ile Glu Val Ser Ala Pro Gly Ala Ser Val Glu Ser Thr Trp Tyr Thr
                230                 235                 240

Gly Gly Tyr Asn Thr Ile Ser Gly Thr Ser Met Ala Thr Pro His Val
            245                 250                 255

Ala Gly Leu Ala Ala Lys Ile Trp Ser Ala Asn Thr Ser Leu Ser His
            260                 265                 270

Ser Gln Leu Arg Thr Glu Leu Gln Asn Arg Ala Lys Val Tyr Asp Ile
    275                 280                 285

Lys Gly Gly Ile Gly Ala Gly Thr Gly Asp Asp Tyr Ala Ser Gly Phe
290                 295                 300                 305

Gly Tyr Pro Arg Val Lys
                310

<210> SEQ ID NO 3
<211> LENGTH: 311
<212> TYPE: PRT
<213> ORGANISM: Bacillus sp.

<400> SEQUENCE: 3

Ala Val Pro Ser Thr Gln Thr Pro Trp Gly Ile Lys Ser Ile Tyr Asn
1               5                   10                  15

Asp Gln Ser Ile Thr Lys Thr Thr Gly Gly Ser Gly Ile Lys Val Ala
            20                  25                  30

Val Leu Asp Thr Gly Val Tyr Thr Ser His Leu Asp Leu Ala Gly Ser
            35                  40                  45

Ala Glu Gln Cys Lys Asp Phe Thr Gln Ser Asn Pro Leu Val Asp Gly
    50                  55                  60

Ser Cys Thr Asp Arg Gln Gly His Gly Thr His Val Ala Gly Thr Val
65                  70                  75                  80

Leu Ala His Gly Gly Ser Asn Gly Gln Gly Val Tyr Gly Val Ala Pro
                85                  90                  95

Gln Ala Lys Leu Trp Ala Tyr Lys Val Leu Gly Asp Asn Gly Ser Gly
            100                 105                 110

Tyr Ser Asp Asp Ile Ala Ala Ala Ile Arg His Val Ala Asp Glu Ala
            115                 120                 125

Ser Arg Thr Gly Ser Lys Val Val Ile Asn Met Ser Leu Gly Ser Ser
    130                 135                 140

Ala Lys Asp Ser Leu Ile Ala Ser Ala Val Asp Tyr Ala Tyr Gly Lys
145                 150                 155                 160
```

Gly Val Leu Ile Val Ala Ala Ala Gly Asn Ser Gly Ser Gly Ser Asn
            165                 170                 175

Thr Ile Gly Phe Pro Gly Gly Leu Val Asn Ala Val Ala Val Ala Ala
        180                 185                 190

Leu Glu Asn Val Gln Gln Asn Gly Thr Tyr Arg Val Ala Asp Phe Ser
            195                 200                 205

Ser Arg Gly Asn Pro Ala Thr Ala Gly Asp Tyr Ile Ile Gln Glu Arg
210                 215                 220

Asp Ile Glu Val Ser Ala Pro Gly Ala Ser Val Glu Ser Thr Trp Tyr
225                 230                 235                 240

Thr Gly Gly Tyr Asn Thr Ile Ser Gly Thr Ser Met Ala Thr Pro His
            245                 250                 255

Val Ala Gly Leu Ala Ala Lys Ile Trp Ser Ala Asn Thr Ser Leu Ser
            260                 265                 270

His Ser Gln Leu Arg Thr Glu Leu Gln Asn Arg Ala Lys Val Tyr Asp
            275                 280                 285

Ile Lys Gly Gly Ile Gly Ala Gly Thr Gly Asp Asp Tyr Ala Ser Gly
            290                 295                 300

Phe Gly Tyr Pro Arg Val Lys
305                 310

<210> SEQ ID NO 4
<211> LENGTH: 311
<212> TYPE: PRT
<213> ORGANISM: Bacillus sp.

<400> SEQUENCE: 4

Ala Val Pro Ser Thr Gln Thr Pro Trp Gly Ile Lys Ser Ile Tyr Asn
1               5                   10                  15

Asp Gln Ser Ile Thr Lys Thr Thr Gly Gly Ser Gly Ile Lys Val Ala
            20                  25                  30

Val Leu Asp Thr Gly Val Tyr Thr Ser His Leu Asp Leu Ala Gly Ser
        35                  40                  45

Ala Glu Gln Cys Lys Asp Phe Thr Gln Ser Asn Pro Leu Val Asp Gly
    50                  55                  60

Ser Cys Thr Asp Arg Gln Gly His Gly Thr His Val Ala Gly Thr Val
65                  70                  75                  80

Leu Ala His Gly Gly Ser Asn Gly Gln Gly Val Tyr Gly Val Ala Pro
                85                  90                  95

Gln Ala Lys Leu Trp Ala Tyr Lys Val Leu Gly Asp Asn Gly Ser Gly
            100                 105                 110

Tyr Ser Asp Asp Ile Ala Ala Ile Arg His Val Ala Asp Glu Ala
            115                 120                 125

Ser Arg Thr Gly Ser Lys Val Val Ile Asn Met Ser Leu Gly Ser Ser
130                 135                 140

Ala Lys Asp Ser Leu Ile Ala Ser Ala Val Asp Tyr Ala Tyr Gly Lys
145                 150                 155                 160

Gly Val Leu Ile Val Ala Ala Ala Gly Asn Ser Gly Pro Gly Pro Asn
            165                 170                 175

Thr Ile Gly Phe Pro Gly Gly Leu Val Asn Ala Val Ala Val Ala Ala
        180                 185                 190

Leu Glu Asn Val Gln Gln Asn Gly Thr Tyr Arg Val Ala Asp Phe Ser
            195                 200                 205

Ser Arg Gly Asn Pro Ala Thr Ala Gly Asp Tyr Ile Ile Gln Glu Arg
210                 215                 220

-continued

Asp Ile Glu Val Ser Ala Pro Gly Ala Ser Val Glu Ser Thr Trp Tyr
225                 230                 235                 240

Thr Gly Gly Tyr Asn Thr Ile Ser Gly Thr Ser Met Ala Thr Pro His
            245                 250                 255

Val Ala Gly Leu Ala Ala Lys Ile Trp Ser Ala Asn Thr Ser Leu Ser
        260                 265                 270

His Ser Gln Leu Arg Thr Glu Leu Gln Asn Arg Ala Lys Val Tyr Asp
    275                 280                 285

Ile Lys Gly Gly Ile Gly Ala Gly Thr Gly Asp Asp Tyr Ala Ser Gly
290                 295                 300

Phe Gly Tyr Pro Arg Val Lys
305                 310

<210> SEQ ID NO 5
<211> LENGTH: 311
<212> TYPE: PRT
<213> ORGANISM: Bacillus sp.

<400> SEQUENCE: 5

Ala Val Pro Ser Thr Gln Thr Pro Trp Gly Ile Lys Ser Ile Tyr Asn
1               5                   10                  15

Asp Gln Ser Ile Thr Lys Thr Gly Gly Ser Gly Ile Lys Val Ala
            20                  25                  30

Val Leu Asp Thr Gly Val Tyr Thr Ser His Leu Asp Leu Ala Gly Ser
        35                  40                  45

Ala Glu Gln Cys Lys Asp Phe Thr Gln Ser Asn Pro Leu Val Asp Gly
    50                  55                  60

Ser Cys Thr Asp Arg Gln Gly His Gly Thr His Val Ala Gly Thr Val
65                  70                  75                  80

Leu Ala His Gly Gly Ser Asn Gly Gln Gly Val Tyr Gly Val Ala Pro
                85                  90                  95

Gln Ala Lys Leu Trp Ala Tyr Lys Val Leu Gly Asp Asn Gly Ser Gly
            100                 105                 110

Tyr Ser Asp Asp Ile Ala Ala Ile Arg His Val Ala Asp Glu Ala
        115                 120                 125

Ser Arg Thr Gly Ser Lys Val Val Ile Asn Met Ser Leu Gly Ser Ser
130                 135                 140

Ala Lys Asp Ser Leu Ile Ala Ser Ala Val Asp Tyr Ala Tyr Gly Lys
145                 150                 155                 160

Gly Val Leu Ile Val Ala Ala Gly Asn Ser Gly Pro Gly Pro Asn
            165                 170                 175

Thr Ile Gly Tyr Pro Gly Gly Leu Val Asn Ala Val Ala Val Ala Ala
        180                 185                 190

Leu Glu Asn Val Gln Gln Asn Gly Thr Tyr Arg Val Ala Asp Phe Ser
    195                 200                 205

Ser Arg Gly Asn Pro Ala Thr Ala Gly Asp Tyr Ile Ile Gln Glu Arg
210                 215                 220

Asp Ile Glu Val Ser Ala Pro Gly Ala Ser Val Glu Ser Thr Trp Tyr
225                 230                 235                 240

Thr Gly Gly Tyr Asn Thr Ile Ser Gly Thr Ser Met Ala Thr Pro His
            245                 250                 255

Val Ala Gly Leu Ala Ala Lys Ile Trp Ser Ala Asn Thr Ser Leu Ser
        260                 265                 270

His Ser Gln Leu Arg Thr Glu Leu Gln Asn Arg Ala Lys Val Tyr Asp
    275                 280                 285

```
Ile Lys Gly Gly Ile Gly Ala Gly Thr Gly Asp Asp Tyr Ala Ser Gly
    290             295             300

Phe Gly Tyr Pro Arg Val Lys
305             310
```